(12) United States Patent
Wallace et al.

(10) Patent No.: US 10,052,116 B2
(45) Date of Patent: Aug. 21, 2018

(54) DEVICES AND METHODS FOR TREATING TISSUE

(71) Applicant: Amendia, Inc., Marietta, GA (US)

(72) Inventors: Michael P. Wallace, Pleasanton, CA (US); Robert Garabedian, Mountain View, CA (US); Gregory B. Arcenio, Redwood City, CA (US); Jeffery L. Bleich, Palo Alto, CA (US); Vahid Saadat, Atherton, CA (US); Winnie Chung, San Francisco, CA (US)

(73) Assignee: Amendia, Inc., Marietta, GA (US)

(*) Notice: Subject to any disclaimer, the term of this patent is extended or adjusted under 35 U.S.C. 154(b) by 513 days.

(21) Appl. No.: 14/790,598

(22) Filed: Jul. 2, 2015

(65) Prior Publication Data

US 2015/0306348 A1 Oct. 29, 2015

Related U.S. Application Data

(60) Division of application No. 12/911,537, filed on Oct. 25, 2010, now Pat. No. 9,101,386, which is a
(Continued)

(51) Int. Cl.
*A61B 17/32* (2006.01)
*A61B 17/16* (2006.01)
(Continued)

(52) U.S. Cl.
CPC .......... *A61B 17/32* (2013.01); *A61B 17/1659* (2013.01); *A61B 17/1671* (2013.01);
(Continued)

(58) Field of Classification Search
CPC ............................ A61B 17/1659; A61B 17/32
See application file for complete search history.

(56) References Cited

U.S. PATENT DOCUMENTS

| 184,804 A | 11/1876 | Stohlmann |
|---|---|---|
| 273,806 A | 3/1883 | Boice |

(Continued)

FOREIGN PATENT DOCUMENTS

| CN | 1338911 | 3/2002 |
|---|---|---|
| CN | 101291633 | 10/2008 |

(Continued)

OTHER PUBLICATIONS

Arcenio et al.; U.S. Appl. No. 12/980,165 entitled "Systems and Methods for Performing Spinal Fusion", filed Dec. 28, 2010.
(Continued)

*Primary Examiner* — Andrew Yang
(74) *Attorney, Agent, or Firm* — David L. King

(57) ABSTRACT

Described herein are devices, systems and methods for treating target tissue in a patient's spine. In general, the methods include the steps of advancing a wire into the patient from a first location, through a neural foramen, and out of the patient from a second location; connecting a tissue modification device to the wire; positioning the tissue modification device through the neural foramen using the wire; modifying target tissue in the spine by moving the tissue modification device against the target tissue; and delivering an agent to modified target tissue, wherein the agent is configured to inhibit blood flow from the modified target tissue. In some embodiments, the step of modifying target tissue comprises removing target tissue located ventral to the superior articular process while avoiding non-target tissue located lateral to the superior articular process.

9 Claims, 32 Drawing Sheets

US 10,052,116 B2
Page 2

Related U.S. Application Data continuation-in-part of application No. 11/251,205, filed on Oct. 15, 2005, now Pat. No. 7,918,849, and a continuation-in-part of application No. 11/468,247, filed on Aug. 29, 2006, now Pat. No. 7,857,813.

(60) Provisional application No. 60/619,306, filed on Oct. 15, 2004, provisional application No. 60/622,865, filed on Oct. 28, 2004, provisional application No. 60/681,719, filed on May 16, 2005, provisional application No. 60/681,864, filed on May 16, 2005, provisional application No. 60/685,190, filed on May 27, 2005, provisional application No. 61/254,656, filed on Oct. 23, 2009, provisional application No. 61/260,012, filed on Nov. 11, 2009, provisional application No. 61/289,075, filed on Dec. 22, 2009, provisional application No. 61/388,601, filed on Sep. 30, 2010.

(51) Int. Cl.
*A61F 2/00* (2006.01)
*A61M 25/00* (2006.01)
*A61B 90/00* (2016.01)
*A61B 17/34* (2006.01)
*A61B 18/14* (2006.01)
*A61B 17/00* (2006.01)
*A61B 17/22* (2006.01)
*A61N 1/05* (2006.01)
*A61N 1/36* (2006.01)
*A61M 25/09* (2006.01)
*A61B 17/14* (2006.01)

(52) U.S. Cl.
CPC .. *A61B 17/320016* (2013.01); *A61B 17/3468* (2013.01); *A61B 18/1487* (2013.01); *A61B 90/04* (2016.02); *A61F 2/0045* (2013.01); *A61M 25/0067* (2013.01); *A61B 17/149* (2016.11); *A61B 17/3401* (2013.01); *A61B 17/3403* (2013.01); *A61B 18/1477* (2013.01); *A61B 2017/003* (2013.01); *A61B 2017/00261* (2013.01); *A61B 2017/00331* (2013.01); *A61B 2017/00867* (2013.01); *A61B 2017/22038* (2013.01); *A61B 2017/22049* (2013.01); *A61B 2017/320004* (2013.01); *A61B 2017/32006* (2013.01); *A61B 2017/320044* (2013.01); *A61B 2018/1407* (2013.01); *A61B 2018/1425* (2013.01); *A61B 2090/061* (2016.02); *A61B 2090/08021* (2016.02); *A61M 25/09* (2013.01); *A61M 2210/1003* (2013.01); *A61N 1/0551* (2013.01); *A61N 1/36017* (2013.01)

(56) References Cited

U.S. PATENT DOCUMENTS

| | | |
|---|---|---|
| 289,104 A | 11/1883 | How |
| 432,384 A | 7/1890 | Eastin |
| 863,389 A | 8/1907 | Harkin |
| 1,039,487 A | 9/1912 | Casebolt |
| 1,201,467 A | 10/1916 | Hoalund |
| 1,374,638 A | 4/1921 | De Cew et al. |
| 1,543,195 A | 6/1925 | Thvaesen |
| 1,690,812 A | 11/1928 | Bertels |
| 1,938,200 A | 12/1933 | Wells |
| 2,243,757 A | 5/1941 | Kohls et al. |
| 2,269,749 A | 1/1942 | Wilkie |
| 2,372,553 A | 3/1945 | Coddinaton |
| 2,437,697 A | 3/1948 | Kalom |
| 2,516,882 A | 8/1950 | Kalom |
| 2,704,064 A | 5/1955 | Fizzell |
| 2,820,281 A | 1/1958 | Arnsen |
| 2,843,128 A | 7/1958 | Storz |
| 2,982,005 A | 5/1961 | Booth |
| RE25,582 E | 5/1964 | Davies |
| 3,150,470 A | 9/1964 | Barron |
| 3,200,814 A | 8/1965 | Taylor et al. |
| 3,214,824 A | 11/1965 | Brown |
| 3,389,447 A | 6/1968 | Theobald et al. |
| 3,491,776 A | 1/1970 | Flemina |
| 3,495,590 A | 2/1970 | Zeiller |
| 3,528,152 A | 9/1970 | Funakubo et al. |
| 3,624,484 A | 11/1971 | Colyer |
| 3,640,280 A | 2/1972 | Slanker et al. |
| 3,651,844 A | 3/1972 | Barnes |
| 3,664,329 A | 5/1972 | Naylor |
| 3,682,162 A | 8/1972 | Colyer |
| 3,699,729 A | 10/1972 | Garvey et al. |
| 3,752,166 A | 8/1973 | Lyon et al. |
| 3,774,355 A | 11/1973 | Dawson et al. |
| 3,830,226 A | 8/1974 | Staub et al. |
| 3,835,859 A | 9/1974 | Roberts et al. |
| 3,956,858 A | 5/1976 | Catlin et al. |
| 3,957,036 A | 5/1976 | Normann |
| 3,978,862 A | 9/1976 | Morrison |
| 3,999,294 A | 12/1976 | Shaben |
| 4,015,931 A | 4/1977 | Thakur |
| 4,099,519 A | 7/1978 | Warren |
| 4,108,182 A | 8/1978 | Hartman et al. |
| 4,160,320 A | 7/1979 | Wikoff |
| 4,172,440 A | 10/1979 | Schneider et al. |
| 4,203,444 A | 5/1980 | Bonnell et al. |
| 4,207,897 A | 6/1980 | Lloyd et al. |
| 4,259,276 A | 3/1981 | Rawlings |
| 4,405,061 A | 9/1983 | Bergandy |
| D273,806 S | 5/1984 | Boleskv et al. |
| 4,464,836 A | 8/1984 | Hissa |
| 4,502,184 A | 3/1985 | Karubian |
| 4,515,168 A | 5/1985 | Chester et al. |
| 4,518,022 A | 5/1985 | Valdes et al. |
| 4,545,374 A | 10/1985 | Jacobson |
| 4,573,448 A | 3/1986 | Kambin |
| 4,580,545 A | 4/1986 | Dorsten |
| 4,590,949 A | 5/1986 | Pohndorf |
| 4,616,660 A | 10/1986 | Johns |
| 4,621,636 A | 11/1986 | Fogarty |
| 4,625,725 A | 12/1986 | Davison et al. |
| 4,660,571 A | 4/1987 | Hess et al. |
| 4,678,459 A | 7/1987 | Onik et al. |
| 4,690,642 A | 9/1987 | Kvotani |
| 4,700,702 A | 10/1987 | Nilsson |
| 4,709,699 A | 12/1987 | Michael et al. |
| 4,741,343 A | 5/1988 | Bowman |
| 4,750,249 A | 6/1988 | Richardson |
| 4,794,931 A | 1/1989 | Yock |
| 4,808,157 A | 2/1989 | Coombs |
| 4,817,628 A | 4/1989 | Zealear et al. |
| 4,856,193 A | 8/1989 | Grachan |
| 4,867,155 A | 9/1989 | Isaacson |
| 4,872,452 A | 10/1989 | Alexson |
| 4,873,978 A | 10/1989 | Ginsburi |
| 4,883,460 A | 11/1989 | Zanetti |
| 4,894,063 A | 1/1990 | Nashe |
| 4,912,799 A | 4/1990 | Coleman, Jr. |
| RE33,258 E | 7/1990 | Onik et al. |
| 4,943,295 A | 7/1990 | Hartlaub et al. |
| 4,946,462 A | 8/1990 | Watanabe |
| 4,957,117 A | 9/1990 | Wysham |
| 4,962,766 A | 10/1990 | Herzon |
| 4,973,329 A | 11/1990 | Park et al. |
| 4,990,148 A | 2/1991 | Warrick, III et al. |
| 4,994,036 A | 2/1991 | Biscopinq et al. |
| 4,994,072 A | 2/1991 | Bhate et al. |
| 4,995,200 A | 2/1991 | Eberhart |
| 5,019,082 A | 5/1991 | Frey et al. |
| 5,025,787 A | 6/1991 | Sutherland et al. |
| 5,026,379 A | 6/1991 | Yoon |
| 5,026,386 A | 6/1991 | Michelson |
| 5,078,137 A | 1/1992 | Edell et al. |

(56) References Cited

U.S. PATENT DOCUMENTS

| | | |
|---|---|---|
| 5,089,003 A | 2/1992 | Fallin et al. |
| 5,100,424 A | 3/1992 | Janq et al. |
| 5,108,403 A | 4/1992 | Stern |
| 5,123,400 A | 6/1992 | Edgerton |
| 5,125,928 A | 6/1992 | Parins et al. |
| 5,147,364 A | 9/1992 | Comparetto |
| 5,152,749 A | 10/1992 | Giesv et al. |
| 5,161,534 A | 11/1992 | Berthiaume |
| 5,163,939 A | 11/1992 | Winston |
| 5,176,649 A | 1/1993 | Wakabayashi |
| 5,178,145 A | 1/1993 | Rea |
| 5,178,161 A | 1/1993 | Kovacs |
| 5,191,888 A | 3/1993 | Palmer et al. |
| 5,195,507 A | 3/1993 | Bilweis |
| 5,201,704 A | 4/1993 | Ray |
| 5,215,105 A | 6/1993 | Kizelshteyn et al. |
| 5,219,358 A | 6/1993 | Bendel et al. |
| 5,234,435 A | 8/1993 | Seagrave, Jr. |
| 5,242,418 A | 9/1993 | Weinstein |
| 5,250,035 A | 10/1993 | Smith et al. |
| 5,255,691 A | 10/1993 | Otten |
| 5,271,415 A | 12/1993 | Foerster et al. |
| 5,281,218 A | 1/1994 | Imran |
| 5,284,153 A | 2/1994 | Raymond et al. |
| 5,284,154 A | 2/1994 | Raymond et al. |
| 5,300,077 A | 4/1994 | Howell |
| 5,325,868 A | 7/1994 | Kimmelstiel |
| 5,341,807 A | 8/1994 | Nardella |
| 5,351,679 A | 10/1994 | Mavzels et al. |
| 5,353,784 A | 10/1994 | Nady-Mohamed |
| 5,353,789 A | 10/1994 | Schlobohm |
| 5,353,802 A | 10/1994 | Ollmar |
| 5,360,441 A | 11/1994 | Otten |
| 5,365,928 A | 11/1994 | Rhinehart et al. |
| 5,374,261 A | 12/1994 | Yoon |
| 5,383,879 A | 1/1995 | Phillips |
| 5,385,146 A | 1/1995 | Goldreyer |
| 5,387,218 A | 2/1995 | Meswania |
| 5,396,880 A | 3/1995 | Kagan et al. |
| 5,421,348 A | 6/1995 | Lamard |
| 5,423,331 A | 6/1995 | Wysham |
| 5,437,661 A | 8/1995 | Rieser |
| 5,439,464 A | 8/1995 | Shapiro |
| 5,441,044 A | 8/1995 | Tovey et al. |
| 5,441,510 A | 8/1995 | Simpson et al. |
| 5,454,815 A | 10/1995 | Geisser et al. |
| 5,456,254 A | 10/1995 | Pietroski et al. |
| 5,496,325 A | 3/1996 | Mclees |
| 5,512,037 A | 4/1996 | Russell et al. |
| 5,515,848 A | 5/1996 | Corbett, III et al. |
| 5,531,749 A | 7/1996 | Michelson |
| 5,534,009 A | 7/1996 | Lander |
| 5,546,958 A | 8/1996 | Thorud et al. |
| 5,554,110 A | 9/1996 | Edwards et al. |
| 5,555,892 A | 9/1996 | Tipton |
| 5,560,372 A | 10/1996 | Cory |
| 5,562,695 A | 10/1996 | Obenchain |
| 5,571,181 A | 11/1996 | Li |
| 5,582,618 A | 12/1996 | Chin et al. |
| 5,591,170 A | 1/1997 | Spievack et al. |
| 5,598,848 A | 2/1997 | Swanson et al. |
| 5,620,447 A | 4/1997 | Smith et al. |
| 5,630,426 A | 5/1997 | Eaaers et al. |
| 5,634,475 A | 6/1997 | Wolvek |
| 5,643,304 A | 7/1997 | Schechter et al. |
| 5,651,373 A | 7/1997 | Mah |
| 5,656,012 A | 8/1997 | Sienkiewcz |
| 5,680,860 A | 10/1997 | Imran |
| 5,681,324 A | 10/1997 | Kammerer et al. |
| 5,697,889 A | 12/1997 | Slotman et al. |
| 5,709,697 A | 1/1998 | Ratcliff et al. |
| 5,725,530 A | 3/1998 | Popken |
| 5,735,792 A | 4/1998 | Vanden Hoek et al. |
| 5,755,732 A | 5/1998 | Green et al. |
| 5,759,159 A | 6/1998 | Masreliez |
| 5,762,629 A | 6/1998 | Kambin |
| 5,766,168 A | 6/1998 | Mantell |
| 5,769,865 A | 6/1998 | Kermode et al. |
| 5,775,331 A | 7/1998 | Raymond et al. |
| 5,779,642 A | 7/1998 | Nightenqale |
| 5,788,653 A | 8/1998 | Lorenzo |
| 5,792,044 A | 8/1998 | Foley et al. |
| 5,795,308 A | 8/1998 | Russin |
| 5,800,350 A | 9/1998 | Coppleson et al. |
| 5,803,902 A | 9/1998 | Sienkiewicz et al. |
| 5,803,904 A | 9/1998 | Mehdizadeh |
| 5,807,263 A | 9/1998 | Chance |
| 5,810,744 A | 9/1998 | Chu et al. |
| 5,813,405 A | 9/1998 | Montano, Jr. et al. |
| 5,824,040 A | 10/1998 | Cox et al. |
| 5,830,151 A | 11/1998 | Hadzic et al. |
| 5,830,157 A | 11/1998 | Foote |
| 5,830,188 A | 11/1998 | Abouleish |
| 5,833,692 A | 11/1998 | Cesarini et al. |
| 5,836,810 A | 11/1998 | Asum |
| 5,836,948 A | 11/1998 | Zucherman et al. |
| 5,843,110 A | 12/1998 | Dross et al. |
| 5,846,196 A | 12/1998 | Siekmeyer et al. |
| 5,846,244 A | 12/1998 | Cripe |
| 5,851,191 A | 12/1998 | Gozani |
| 5,851,209 A | 12/1998 | Kummer et al. |
| 5,851,214 A | 12/1998 | Larsen et al. |
| 5,853,373 A | 12/1998 | Griffith et al. |
| 5,865,844 A | 2/1999 | Plaia et al. |
| 5,868,767 A | 2/1999 | Farley et al. |
| 5,879,353 A | 3/1999 | Terrv |
| 5,885,219 A | 3/1999 | Nightengale |
| 5,895,417 A | 4/1999 | Pomeranz et al. |
| 5,897,583 A | 4/1999 | Meyer et al. |
| 5,899,909 A | 5/1999 | Claren et al. |
| 5,904,657 A | 5/1999 | Unsworth et al. |
| 5,916,173 A | 6/1999 | Kirsner |
| 5,918,604 A | 7/1999 | Whelan |
| 5,919,190 A | 7/1999 | VanDusseldorp |
| 5,928,158 A | 7/1999 | Aristides |
| 5,928,159 A | 7/1999 | Eaaers et al. |
| 5,941,822 A | 8/1999 | Skladnev et al. |
| 5,961,522 A | 10/1999 | Mehdizadeh |
| 5,972,013 A | 10/1999 | Schmidt |
| 5,976,110 A | 11/1999 | Greengrass et al. |
| 5,976,146 A | 11/1999 | Oaawa et al. |
| 6,002,964 A | 12/1999 | Feler et al. |
| 6,004,326 A | 12/1999 | Castro et al. |
| 6,004,330 A | 12/1999 | Middleman et al. |
| 6,010,493 A | 1/2000 | Snoke |
| 6,015,406 A | 1/2000 | Goble et al. |
| 6,022,362 A | 2/2000 | Lee et al. |
| 6,030,383 A | 2/2000 | Benderev |
| 6,030,401 A | 2/2000 | Marino |
| 6,038,480 A | 3/2000 | Hrdlicka et al. |
| 6,048,345 A | 4/2000 | Berke et al. |
| 6,068,642 A | 5/2000 | Johnson et al. |
| 6,073,051 A | 6/2000 | Sharkey et al. |
| 6,099,514 A | 8/2000 | Sharkey et al. |
| 6,102,930 A | 8/2000 | Simmons, Jr. |
| 6,106,558 A | 8/2000 | Picha |
| 6,113,534 A | 9/2000 | Koros et al. |
| D432,384 S | 10/2000 | Simons |
| 6,132,387 A | 10/2000 | Gozani et al. |
| 6,136,014 A | 10/2000 | Sirimanne et al. |
| 6,142,993 A | 11/2000 | Whavne et al. |
| 6,142,994 A | 11/2000 | Swanson et al. |
| 6,146,380 A | 11/2000 | Racz et al. |
| 6,152,894 A | 11/2000 | Kubler |
| 6,169,916 B1 | 1/2001 | West |
| 6,205,360 B1 | 3/2001 | Carter |
| 6,214,001 B1 | 4/2001 | Casscells et al. |
| 6,214,016 B1 | 4/2001 | Williams et al. |
| 6,236,892 B1 | 5/2001 | Feler |
| 6,251,115 B1 | 6/2001 | Williams et al. |
| 6,256,540 B1 | 7/2001 | Panescu et al. |
| 6,259,945 B1 | 7/2001 | Epstein et al. |
| 6,261,582 B1 | 7/2001 | Needham et al. |
| 6,266,551 B1 | 7/2001 | Osadchv et al. |

(56) References Cited

U.S. PATENT DOCUMENTS

| | | |
|---|---|---|
| 6,266,558 B1 | 7/2001 | Gozani et al. |
| 6,267,760 B1 | 7/2001 | Swanson |
| 6,272,367 B1 | 8/2001 | Chance |
| 6,277,094 B1 | 8/2001 | Schendel |
| 6,280,447 B1 | 8/2001 | Marino et al. |
| 6,292,702 B1 | 9/2001 | Kinci et al. |
| 6,298,256 B1 | 10/2001 | Meyer |
| 6,312,392 B1 | 11/2001 | Herzon |
| 6,324,418 B1 | 11/2001 | Crowley et al. |
| 6,324,432 B1 | 11/2001 | Rigaux et al. |
| 6,325,764 B1 | 12/2001 | Griffith et al. |
| 6,334,068 B1 | 12/2001 | Hacker |
| 6,343,226 B1 | 1/2002 | Sunde et al. |
| 6,358,254 B1 | 3/2002 | Anderson |
| 6,360,750 B1 | 3/2002 | Gerber et al. |
| 6,364,886 B1 | 4/2002 | Sklar |
| 6,368,324 B1 | 4/2002 | Dinqer et al. |
| 6,370,411 B1 | 4/2002 | Osadchy et al. |
| 6,370,435 B2 | 4/2002 | Panescu et al. |
| 6,383,509 B1 | 5/2002 | Donovan et al. |
| 6,390,906 B1 | 5/2002 | Subramanian |
| 6,391,028 B1 | 5/2002 | Fanton et al. |
| 6,416,505 B1 | 7/2002 | Fleischman et al. |
| 6,423,071 B1 | 7/2002 | Lawson |
| 6,423,080 B1 | 7/2002 | Gellman et al. |
| 6,425,859 B1 | 7/2002 | Foley et al. |
| 6,425,887 B1 | 7/2002 | McGuckin et al. |
| 6,428,486 B2 | 8/2002 | Ritchart et al. |
| 6,436,101 B1 | 8/2002 | Hamada |
| 6,442,848 B1 | 9/2002 | Dean |
| 6,446,621 B1 | 9/2002 | Svensson |
| 6,451,335 B1 | 9/2002 | Goldenheim et al. |
| 6,454,767 B2 | 9/2002 | Alleyne |
| 6,464,682 B1 | 10/2002 | Snoke |
| 6,466,817 B1 | 10/2002 | Kaula et al. |
| 6,468,289 B1 | 10/2002 | Bonutti |
| 6,470,209 B2 | 10/2002 | Snoke |
| 6,478,805 B1 | 11/2002 | Marino et al. |
| 6,487,439 B1 | 11/2002 | Skladnev et al. |
| 6,488,636 B2 | 12/2002 | Bryan et al. |
| 6,491,646 B1 | 12/2002 | Blackledqe |
| 6,500,128 B2 | 12/2002 | Marino |
| 6,500,189 B1 | 12/2002 | Lanq et al. |
| 6,512,958 B1 | 1/2003 | Swoyer et al. |
| 6,516,223 B2 | 2/2003 | Hofmann |
| 6,520,907 B1 | 2/2003 | Foley et al. |
| 6,527,786 B1 | 3/2003 | Davis et al. |
| 6,533,749 B1 | 3/2003 | Mitusina et al. |
| 6,535,759 B1 | 3/2003 | Epstein et al. |
| 6,540,742 B1 | 4/2003 | Thomas et al. |
| 6,540,761 B2 | 4/2003 | Houser |
| 6,546,270 B1 | 4/2003 | Goldin et al. |
| 6,558,353 B2 | 5/2003 | Zohmann |
| 6,558,390 B2 | 5/2003 | Craaa |
| 6,562,033 B2 | 5/2003 | Shah et al. |
| 6,564,078 B1 | 5/2003 | Marino et al. |
| 6,564,079 B1 | 5/2003 | Cory et al. |
| 6,564,088 B1 | 5/2003 | Soller et al. |
| 6,569,160 B1 | 5/2003 | Goldin et al. |
| 6,575,979 B1 | 6/2003 | Craoo |
| 6,579,291 B1 | 6/2003 | Keith et al. |
| 6,584,345 B2 | 6/2003 | Govari |
| 6,592,559 B1 | 7/2003 | Pakter et al. |
| 6,595,932 B2 | 7/2003 | Ferrera |
| 6,597,955 B2 | 7/2003 | Panescu et al. |
| 6,606,523 B1 | 8/2003 | Jenkins |
| 6,607,530 B1 | 8/2003 | Carl et al. |
| 6,609,018 B2 | 8/2003 | Corv et al. |
| 6,610,066 B2 | 8/2003 | Dinger et al. |
| 6,620,129 B2 | 9/2003 | Stecker et al. |
| 6,622,731 B2 | 9/2003 | Daniel et al. |
| 6,624,510 B1 | 9/2003 | Chan et al. |
| 6,626,916 B1 | 9/2003 | Yeung et al. |
| 6,632,184 B1 | 10/2003 | Truwit |
| 6,638,233 B2 | 10/2003 | Corvi et al. |
| RE38,335 E | 11/2003 | Aust et al. |
| 6,648,883 B2 | 11/2003 | Francischelli et al. |
| 6,666,874 B2 | 12/2003 | Heitzmann et al. |
| 6,673,063 B2 | 1/2004 | Brett |
| 6,673,068 B1 | 1/2004 | Berube |
| 6,678,552 B2 | 1/2004 | Pearlman |
| 6,682,535 B2 | 1/2004 | Hoooland |
| 6,682,536 B2 | 1/2004 | Vardi et al. |
| 6,685,709 B2 | 2/2004 | Sklar |
| 6,699,246 B2 | 3/2004 | Zuckerman et al. |
| 6,723,049 B2 | 4/2004 | Skladnev et al. |
| 6,726,531 B1 | 4/2004 | Harrel |
| 6,726,685 B2 | 4/2004 | To et al. |
| 6,733,496 B2 | 5/2004 | Sharkey et al. |
| 6,736,815 B2 | 5/2004 | Ginn |
| 6,736,835 B2 | 5/2004 | Pelleqrino et al. |
| 6,746,451 B2 | 6/2004 | Middleton et al. |
| 6,752,814 B2 | 6/2004 | Gellman et al. |
| 6,760,616 B2 | 7/2004 | Hoey et al. |
| 6,764,491 B2 | 7/2004 | Frey et al. |
| 6,772,012 B2 | 8/2004 | Ricart et al. |
| 6,776,765 B2 | 8/2004 | Soukup et al. |
| 6,786,876 B2 | 9/2004 | Cox |
| 6,788,966 B2 | 9/2004 | Kenan et al. |
| 6,790,210 B1 | 9/2004 | Craaa et al. |
| 6,795,737 B2 | 9/2004 | Gielen et al. |
| 6,805,695 B2 | 10/2004 | Keith et al. |
| 6,805,697 B1 | 10/2004 | Helm et al. |
| 6,807,444 B2 | 10/2004 | Tu et al. |
| 6,830,561 B2 | 12/2004 | Jansen et al. |
| 6,830,570 B1 | 12/2004 | Frey et al. |
| 6,832,111 B2 | 12/2004 | Tu et al. |
| 6,845,264 B1 | 1/2005 | Skladnev et al. |
| 6,847,849 B2 | 1/2005 | Mamo et al. |
| 6,851,430 B2 | 2/2005 | Tsou |
| 6,865,409 B2 | 3/2005 | Getsla et al. |
| 6,872,204 B2 | 3/2005 | Houser |
| 6,875,221 B2 | 4/2005 | Cull |
| 6,882,879 B2 | 4/2005 | Rock |
| 6,884,220 B2 | 4/2005 | Aviv et al. |
| 6,890,353 B2 | 5/2005 | Cohn et al. |
| 6,895,283 B2 | 5/2005 | Erickson et al. |
| 6,899,716 B2 | 5/2005 | Craaa Andrew |
| 6,907,884 B2 | 6/2005 | Pellegrino et al. |
| 6,911,003 B2 | 6/2005 | Anderson et al. |
| 6,911,016 B2 | 6/2005 | Balzum et al. |
| 6,916,328 B2 | 7/2005 | Brett |
| 6,923,813 B2 | 8/2005 | Phillips et al. |
| 6,929,647 B2 | 8/2005 | Cohen |
| 6,949,104 B2 | 9/2005 | Griffis et al. |
| 6,953,461 B2 | 10/2005 | Mcclurken et al. |
| 6,962,587 B2 | 11/2005 | Johnson et al. |
| 6,969,392 B2 | 11/2005 | Gitis et al. |
| 6,971,986 B2 | 12/2005 | Staskin et al. |
| 6,972,199 B2 | 12/2005 | Lebouitz et al. |
| 6,973,342 B1 | 12/2005 | Swanson |
| 6,976,986 B2 | 12/2005 | Berube |
| 6,991,643 B2 | 1/2006 | Saadat |
| 6,994,693 B2 | 2/2006 | Tai |
| 6,997,934 B2 | 2/2006 | Snow et al. |
| 6,999,820 B2 | 2/2006 | Jordan |
| 7,001,333 B2 | 2/2006 | Hamel et al. |
| 7,008,431 B2 | 3/2006 | Simonson |
| 7,010,352 B2 | 3/2006 | Hogan |
| 7,011,635 B1 | 3/2006 | Delay |
| 7,011,663 B2 | 3/2006 | Michelson |
| 7,014,616 B2 | 3/2006 | Ferrera |
| 7,033,373 B2 | 4/2006 | de la Torre et al. |
| 7,041,099 B2 | 5/2006 | Thomas et al. |
| 7,047,084 B2 | 5/2006 | Erickson et al. |
| 7,048,682 B2 | 5/2006 | Neisz et al. |
| 7,050,848 B2 | 5/2006 | Hoey et al. |
| 7,063,682 B1 | 6/2006 | Whayne et al. |
| 7,069,083 B2 | 6/2006 | Finch et al. |
| 7,070,556 B2 | 7/2006 | Anderson et al. |
| 7,070,596 B1 | 7/2006 | Woloszko et al. |
| 7,079,883 B2 | 7/2006 | Marino et al. |
| 7,081,122 B1 | 7/2006 | Reiley et al. |
| 7,087,053 B2 | 8/2006 | Vanney |

(56) References Cited

U.S. PATENT DOCUMENTS

| | | |
|---|---|---|
| 7,087,058 B2 | 8/2006 | Craaa |
| 7,107,104 B2 | 9/2006 | Keravel et al. |
| 7,118,576 B2 | 10/2006 | Gitis et al. |
| 7,141,019 B2 | 11/2006 | Pearlman |
| 7,166,073 B2 | 1/2007 | Ritland |
| 7,166,081 B2 | 1/2007 | McKinley |
| 7,166,107 B2 | 1/2007 | Anderson |
| 7,169,107 B2 | 1/2007 | Jersey-Willuhn et al. |
| 7,169,147 B2 | 1/2007 | Nosel |
| 7,172,562 B2 | 2/2007 | McKinley |
| 7,177,677 B2 | 2/2007 | Kaula et al. |
| 7,181,289 B2 | 2/2007 | Pflueger et al. |
| 7,189,240 B1 | 3/2007 | Dekel |
| 7,192,430 B2 | 3/2007 | Truckai et al. |
| 7,198,598 B2 | 4/2007 | Smith et al. |
| 7,198,626 B2 | 4/2007 | Lee et al. |
| 7,207,949 B2 | 4/2007 | Miles et al. |
| 7,211,082 B2 | 5/2007 | Hall et al. |
| 7,214,186 B2 | 5/2007 | Ritland |
| 7,214,197 B2 | 5/2007 | Prass |
| 7,216,001 B2 | 5/2007 | Hacker et al. |
| 7,223,278 B2 | 5/2007 | Davison et al. |
| 7,236,832 B2 | 6/2007 | Hemmerling et al. |
| 7,238,189 B2 | 7/2007 | Schmiedinq et al. |
| 7,239,911 B2 | 7/2007 | Scholz |
| 7,245,789 B2 | 7/2007 | Bates et al. |
| 7,270,658 B2 | 9/2007 | Woloszko et al. |
| 7,270,659 B2 | 9/2007 | Ricart et al. |
| 7,282,033 B2 | 10/2007 | Urmey |
| 7,282,061 B2 | 10/2007 | Sharkey et al. |
| 7,295,881 B2 | 11/2007 | Cohen et al. |
| 7,318,823 B2 | 1/2008 | Sharps et al. |
| 7,337,005 B2 | 2/2008 | Kim et al. |
| 7,337,006 B2 | 2/2008 | Kim et al. |
| 7,367,972 B2 | 5/2008 | Francischelli et al. |
| 7,383,639 B2 | 6/2008 | Malandain |
| 7,390,330 B2 | 6/2008 | Haro |
| 7,419,487 B2 | 9/2008 | Johnson et al. |
| 7,449,019 B2 | 11/2008 | Uchida et al. |
| 7,452,351 B2 | 11/2008 | Miller et al. |
| 7,470,236 B1 | 12/2008 | Kelleher et al. |
| 7,476,226 B2 | 1/2009 | Weikel et al. |
| 7,494,473 B2 | 2/2009 | Eooers et al. |
| 7,500,977 B2 | 3/2009 | Assell et al. |
| 7,503,920 B2 | 3/2009 | Siegal |
| 7,507,218 B2 | 3/2009 | Aliski et al. |
| 7,522,953 B2 | 4/2009 | Gharib et al. |
| 7,553,307 B2 | 6/2009 | Bleich et al. |
| 7,555,343 B2 | 6/2009 | Bleich |
| 7,578,819 B2 | 8/2009 | Bleich et al. |
| 7,617,006 B2 | 11/2009 | Metzler et al. |
| 7,641,658 B2 | 1/2010 | Shaolian et al. |
| 7,648,521 B2 | 1/2010 | Hestad |
| 7,655,026 B2 | 2/2010 | Justis et al. |
| 7,666,186 B2 | 2/2010 | Harp |
| 7,666,209 B2 | 2/2010 | Zucherman et al. |
| 7,738,968 B2 | 6/2010 | Bleich |
| 7,738,969 B2 | 6/2010 | Bleich |
| 7,740,631 B2 | 6/2010 | Bleich et al. |
| 7,857,813 B2 | 12/2010 | Schmitz et al. |
| 8,303,516 B2 | 11/2012 | Schmitz et al. |
| 8,366,712 B2 | 2/2013 | Bleich et al. |
| 8,398,641 B2 | 3/2013 | Wallace et al. |
| 2001/0014806 A1 | 8/2001 | Ellman et al. |
| 2001/0025192 A1 | 9/2001 | Gerber et al. |
| 2001/0039419 A1 | 11/2001 | Francischelli et al. |
| 2002/0022788 A1 | 2/2002 | Corvi et al. |
| 2002/0029060 A1 | 3/2002 | Hogendiik |
| 2002/0106681 A1 | 8/2002 | Wexler et al. |
| 2002/0128700 A1 | 9/2002 | Cross |
| 2002/0138091 A1 | 9/2002 | Pflueger |
| 2002/0165590 A1 | 11/2002 | Crowe et al. |
| 2002/0183647 A1 | 12/2002 | Gozani et al. |
| 2003/0015203 A1 | 1/2003 | Makower et al. |
| 2003/0074037 A1 | 4/2003 | Moore et al. |
| 2003/0105503 A1 | 6/2003 | Marino |
| 2003/0113906 A1 | 6/2003 | Sangha et al. |
| 2003/0130655 A1 | 7/2003 | Woloszko |
| 2003/0130738 A1 | 7/2003 | Hovda et al. |
| 2003/0167021 A1 | 9/2003 | Shimm |
| 2003/0187368 A1 | 10/2003 | Sata et al. |
| 2003/0188749 A1 | 10/2003 | Nichols et al. |
| 2003/0212400 A1 | 11/2003 | Bloemer et al. |
| 2003/0225412 A1 | 12/2003 | Shiraishi |
| 2003/0225415 A1 | 12/2003 | Richard |
| 2004/0006379 A1 | 1/2004 | Brett |
| 2004/0006391 A1 | 1/2004 | Reiley |
| 2004/0019359 A1 | 1/2004 | Worley et al. |
| 2004/0030330 A1 | 2/2004 | Brassell et al. |
| 2004/0049208 A1 | 3/2004 | Hill et al. |
| 2004/0059260 A1 | 3/2004 | Truwit |
| 2004/0064058 A1 | 4/2004 | McKay |
| 2004/0097927 A1 | 5/2004 | Yeung et al. |
| 2004/0106940 A1 | 6/2004 | Shaolian et al. |
| 2004/0111084 A1 | 6/2004 | Brett |
| 2004/0122433 A1 | 6/2004 | Loubens et al. |
| 2004/0122482 A1 | 6/2004 | Tung et al. |
| 2004/0127893 A1 | 7/2004 | Hovda |
| 2004/0143165 A1 | 7/2004 | Alleyne |
| 2004/0143280 A1 | 7/2004 | Suddaby |
| 2004/0162609 A1 | 8/2004 | Hossainy et al. |
| 2004/0167444 A1 | 8/2004 | Laroya et al. |
| 2004/0167553 A1 | 8/2004 | Simpson et al. |
| 2004/0181150 A1 | 9/2004 | Evans et al. |
| 2004/0199084 A1 | 10/2004 | Kelleher et al. |
| 2004/0199159 A1 | 10/2004 | Lee et al. |
| 2004/0220576 A1 | 11/2004 | Sklar |
| 2004/0225233 A1 | 11/2004 | Frankowski |
| 2004/0260358 A1 | 12/2004 | Vaughan et al. |
| 2005/0027199 A1 | 2/2005 | Clarke |
| 2005/0033393 A1 | 2/2005 | Daglow |
| 2005/0049592 A1 | 3/2005 | Keith et al. |
| 2005/0149035 A1 | 7/2005 | Pimenta et al. |
| 2005/0171587 A1 | 8/2005 | Daqlow et al. |
| 2005/0182454 A1 | 8/2005 | Gharib et al. |
| 2005/0187537 A1 | 8/2005 | Loeb et al. |
| 2005/0197661 A1 | 9/2005 | Carrison et al. |
| 2005/0203599 A1 | 9/2005 | Garabedian et al. |
| 2005/0209610 A1 | 9/2005 | Carrison |
| 2005/0209617 A1 | 9/2005 | Koven et al. |
| 2005/0209622 A1 | 9/2005 | Carrison |
| 2005/0216023 A1 | 9/2005 | Aram et al. |
| 2005/0222598 A1 | 10/2005 | Ho et al. |
| 2005/0222647 A1 | 10/2005 | Wahlstrand et al. |
| 2005/0256423 A1 | 11/2005 | Kirsner |
| 2005/0261692 A1 | 11/2005 | Carrison et al. |
| 2005/0267529 A1 | 12/2005 | Crockett et al. |
| 2005/0277942 A1 | 12/2005 | Kullas et al. |
| 2005/0283148 A1 | 12/2005 | Janssen et al. |
| 2005/0283204 A1 | 12/2005 | Buhlmann et al. |
| 2006/0004369 A1 | 1/2006 | Patel et al. |
| 2006/0015035 A1 | 1/2006 | Rock |
| 2006/0025702 A1 | 2/2006 | Sterratino et al. |
| 2006/0025703 A1 | 2/2006 | Miles et al. |
| 2006/0025797 A1 | 2/2006 | Lock et al. |
| 2006/0030854 A1 | 2/2006 | Haines |
| 2006/0036211 A1 | 2/2006 | Solsberq et al. |
| 2006/0036271 A1 | 2/2006 | Schomer et al. |
| 2006/0036272 A1 | 2/2006 | Solsberq et al. |
| 2006/0058732 A1 | 3/2006 | Harp |
| 2006/0064101 A1 | 3/2006 | Arramon |
| 2006/0079919 A1 | 4/2006 | Harp |
| 2006/0085048 A1 | 4/2006 | Corv et al. |
| 2006/0085049 A1 | 4/2006 | Cory et al. |
| 2006/0089633 A1 | 4/2006 | Bleich et al. |
| 2006/0089650 A1 | 4/2006 | Nolde |
| 2006/0089688 A1 | 4/2006 | Panescu |
| 2006/0095028 A1 | 5/2006 | Bleich |
| 2006/0095059 A1 | 5/2006 | Bleich et al. |
| 2006/0100651 A1 | 5/2006 | Bleich |
| 2006/0122458 A1 | 6/2006 | Bleich |
| 2006/0122620 A1 | 6/2006 | Kim |
| 2006/0122653 A1 | 6/2006 | Bradley et al. |
| 2006/0122654 A1 | 6/2006 | Bradley et al. |

(56) References Cited

U.S. PATENT DOCUMENTS

| | | |
|---|---|---|
| 2006/0129201 A1 | 6/2006 | Lee et al. |
| 2006/0142753 A1 | 6/2006 | Francischelli et al. |
| 2006/0149278 A1 | 7/2006 | Abdou |
| 2006/0161189 A1 | 7/2006 | Harp |
| 2006/0173374 A1 | 8/2006 | Neubardt et al. |
| 2006/0184175 A1 | 8/2006 | Schomer et al. |
| 2006/0195107 A1 | 8/2006 | Jones et al. |
| 2006/0200153 A1 | 9/2006 | Harp |
| 2006/0200154 A1 | 9/2006 | Harp |
| 2006/0200155 A1 | 9/2006 | Harp |
| 2006/0200219 A1 | 9/2006 | Thrope et al. |
| 2006/0206115 A1 | 9/2006 | Schomer et al. |
| 2006/0206117 A1 | 9/2006 | Harp |
| 2006/0206118 A1 | 9/2006 | Kim et al. |
| 2006/0206178 A1 | 9/2006 | Kim |
| 2006/0224060 A1 | 10/2006 | Garell et al. |
| 2006/0224078 A1 | 10/2006 | Hoey et al. |
| 2006/0235451 A1 | 10/2006 | Schomer et al. |
| 2006/0235452 A1 | 10/2006 | Schomer et al. |
| 2006/0241648 A1 | 10/2006 | Bleich et al. |
| 2006/0264952 A1 | 11/2006 | Nelson et al. |
| 2006/0264994 A1 | 11/2006 | Schomer et al. |
| 2006/0271080 A1 | 11/2006 | Suddaby |
| 2006/0276720 A1 | 12/2006 | McGinnis et al. |
| 2006/0276802 A1 | 12/2006 | Vresilovic et al. |
| 2006/0276836 A1 | 12/2006 | BerQin et al. |
| 2007/0010717 A1 | 1/2007 | Craaa |
| 2007/0016097 A1 | 1/2007 | Farquhar et al. |
| 2007/0016185 A1 | 1/2007 | Tullis et al. |
| 2007/0027464 A1 | 2/2007 | Way et al. |
| 2007/0027514 A1 | 2/2007 | Gerber |
| 2007/0049962 A1 | 3/2007 | Marino et al. |
| 2007/0055215 A1 | 3/2007 | Tran et al. |
| 2007/0055262 A1 | 3/2007 | Tomita et al. |
| 2007/0055263 A1 | 3/2007 | Way et al. |
| 2007/0073356 A1 | 3/2007 | Rooney et al. |
| 2007/0106219 A1 | 5/2007 | Grabinsky |
| 2007/0123766 A1 | 5/2007 | Whalen et al. |
| 2007/0123888 A1 | 5/2007 | Bleich et al. |
| 2007/0123890 A1 | 5/2007 | Way et al. |
| 2007/0162044 A1 | 7/2007 | Marino |
| 2007/0162061 A1 | 7/2007 | Way et al. |
| 2007/0162062 A1 | 7/2007 | Norton et al. |
| 2007/0166345 A1 | 7/2007 | Pavcnik et al. |
| 2007/0168007 A1 | 7/2007 | Kuzma et al. |
| 2007/0198019 A1 | 8/2007 | Schomer et al. |
| 2007/0213583 A1 | 9/2007 | Kim et al. |
| 2007/0213584 A1 | 9/2007 | Kim et al. |
| 2007/0213733 A1 | 9/2007 | Bleich et al. |
| 2007/0213734 A1 | 9/2007 | Bleich et al. |
| 2007/0213735 A1 | 9/2007 | Saadat et al. |
| 2007/0213795 A1 | 9/2007 | Bradley et al. |
| 2007/0225703 A1 | 9/2007 | Schmitz et al. |
| 2007/0255162 A1 | 11/2007 | Abboud et al. |
| 2007/0255369 A1 | 11/2007 | Bonde et al. |
| 2007/0260252 A1 | 11/2007 | Schmitz et al. |
| 2007/0270795 A1 | 11/2007 | Francischelli et al. |
| 2007/0270865 A1 | 11/2007 | Amin et al. |
| 2007/0276286 A1 | 11/2007 | Miller |
| 2007/0276390 A1 | 11/2007 | Solsberq et al. |
| 2007/0282217 A1 | 12/2007 | McGinnis et al. |
| 2007/0293782 A1 | 12/2007 | Marino |
| 2007/0299403 A1 | 12/2007 | Crowe et al. |
| 2007/0299459 A1 | 12/2007 | Way et al. |
| 2008/0015582 A1 | 1/2008 | DiPoto et al. |
| 2008/0033465 A1 | 2/2008 | Schmitz et al. |
| 2008/0051812 A1 | 2/2008 | Schmitz et al. |
| 2008/0058820 A1 | 3/2008 | Harp |
| 2008/0058874 A1 | 3/2008 | Westlund et al. |
| 2008/0064945 A1 | 3/2008 | Marino et al. |
| 2008/0064976 A1 | 3/2008 | Kelleher et al. |
| 2008/0064977 A1 | 3/2008 | Kelleher et al. |
| 2008/0065178 A1 | 3/2008 | Kelleher et al. |
| 2008/0071191 A1 | 3/2008 | Kelleher et al. |
| 2008/0086034 A1 | 4/2008 | Schmitz et al. |
| 2008/0091227 A1 | 4/2008 | Schmitz et al. |
| 2008/0097465 A1 | 4/2008 | Rollins et al. |
| 2008/0103504 A1 | 5/2008 | Schmitz et al. |
| 2008/0119711 A1 | 5/2008 | Nikumb et al. |
| 2008/0125621 A1 | 5/2008 | Gellman et al. |
| 2008/0125709 A1 | 5/2008 | Chanq et al. |
| 2008/0140153 A1 | 6/2008 | Burdulis |
| 2008/0140169 A1 | 6/2008 | Imran |
| 2008/0146867 A1 | 6/2008 | Gellman et al. |
| 2008/0147084 A1 | 6/2008 | Bleich et al. |
| 2008/0161809 A1 | 7/2008 | Schmitz et al. |
| 2008/0161810 A1 | 7/2008 | Melkent |
| 2008/0197024 A1 | 8/2008 | Simpson et al. |
| 2008/0200912 A1 | 8/2008 | Lonq et al. |
| 2008/0221383 A1 | 9/2008 | Way et al. |
| 2008/0221586 A1 | 9/2008 | Garcia-Benqochea et al. |
| 2008/0255439 A1 | 10/2008 | Tang et al. |
| 2008/0275458 A1 | 11/2008 | Bleich et al. |
| 2008/0288005 A1 | 11/2008 | Jackson |
| 2008/0312660 A1 | 12/2008 | Bleich et al. |
| 2008/0319459 A1 | 12/2008 | Al-najjar |
| 2009/0018507 A1 | 1/2009 | Schmitz et al. |
| 2009/0018610 A1 | 1/2009 | Gharib et al. |
| 2009/0036936 A1 | 2/2009 | Solsberq et al. |
| 2009/0054804 A1 | 2/2009 | Gharib et al. |
| 2009/0054936 A1 | 2/2009 | Eaaen et al. |
| 2009/0054941 A1 | 2/2009 | Eggen et al. |
| 2009/0062871 A1 | 3/2009 | Chin et al. |
| 2009/0062872 A1 | 3/2009 | Chin et al. |
| 2009/0069709 A1 | 3/2009 | Schmitz et al. |
| 2009/0082763 A1 | 3/2009 | Quick et al. |
| 2009/0105604 A1 | 4/2009 | Bertaqnoli et al. |
| 2009/0105788 A1 | 4/2009 | Bartol et al. |
| 2009/0118709 A1 | 5/2009 | Sand et al. |
| 2009/0124934 A1 | 5/2009 | Rabbitte et al. |
| 2009/0138056 A1 | 5/2009 | Anderson et al. |
| 2009/0143807 A1 | 6/2009 | Sand |
| 2009/0143829 A1 | 6/2009 | Shluzas |
| 2009/0149865 A1 | 6/2009 | Schmitz et al. |
| 2009/0171381 A1 | 7/2009 | Schmitz et al. |
| 2009/0177112 A1 | 7/2009 | Gharib et al. |
| 2009/0177144 A1 | 7/2009 | Masmanidis et al. |
| 2009/0177241 A1 | 7/2009 | Bleich et al. |
| 2009/0182382 A1 | 7/2009 | Justis et al. |
| 2009/0192403 A1 | 7/2009 | Gharib et al. |
| 2009/0204016 A1 | 8/2009 | Gharib et al. |
| 2009/0204119 A1 | 8/2009 | Bleich et al. |
| 2009/0204192 A1 | 8/2009 | Carlton et al. |
| 2009/0209879 A1 | 8/2009 | Kaula et al. |
| 2009/0216284 A1 | 8/2009 | Chin et al. |
| 2009/0299166 A1 | 12/2009 | Nishida |
| 2010/0004654 A1 | 1/2010 | Schmitz et al. |
| 2010/0010334 A1 | 1/2010 | Bleich et al. |
| 2010/0057087 A1 | 3/2010 | Cha |
| 2010/0094231 A1 | 4/2010 | Bleich et al. |
| 2010/0274250 A1 | 10/2010 | Wallace et al. |
| 2010/0331883 A1 | 12/2010 | Schmitz et al. |
| 2010/0331900 A1 | 12/2010 | Garabedian et al. |
| 2011/0004207 A1 | 1/2011 | Wallace et al. |
| 2011/0190772 A1 | 8/2011 | Saadat et al. |
| 2011/0224709 A1 | 9/2011 | Bleich |
| 2011/0224710 A1 | 9/2011 | Bleich |
| 2012/0016368 A1 | 1/2012 | Bleich et al. |
| 2012/0022538 A1 | 1/2012 | Schmitz et al. |
| 2012/0065639 A1 | 3/2012 | Schmitz et al. |
| 2012/0123294 A1 | 5/2012 | Sun et al. |
| 2012/0143206 A1 | 6/2012 | Wallace et al. |
| 2012/0184809 A1 | 7/2012 | Bleich et al. |
| 2012/0191003 A1 | 7/2012 | Garabedian et al. |
| 2012/0239041 A1 | 9/2012 | Bleich et al. |
| 2013/0012831 A1 | 1/2013 | Schmitz et al. |
| 2013/0053851 A1 | 2/2013 | Schmitz et al. |
| 2013/0053853 A1 | 2/2013 | Schmitz et al. |
| 2013/0150855 A1 | 6/2013 | Bleich et al. |
| 2013/0150856 A1 | 6/2013 | Mimran et al. |

(56) References Cited

U.S. PATENT DOCUMENTS

| | | |
|---|---|---|
| 2013/0310837 A1 | 11/2013 | Saadat et al. |
| 2014/0074097 A1 | 3/2014 | Schmitz et al. |

FOREIGN PATENT DOCUMENTS

| | | |
|---|---|---|
| DE | 3209403 A1 | 9/1983 |
| DE | 4036804 A1 | 5/1992 |
| EP | 359883 A1 | 3/1990 |
| EP | 1304080 A2 | 4/2003 |
| EP | 1340467 A2 | 9/2003 |
| EP | 1207794 B1 | 5/2004 |
| EP | 1315463 B1 | 5/2005 |
| EP | 1611851 A1 | 1/2006 |
| EP | 1006885 B1 | 9/2006 |
| FR | 2706309 | 12/1994 |
| GB | 1460837 A | 1/1977 |
| JP | 2960140 B2 | 10/1999 |
| JP | 23116868 | 4/2003 |
| JP | 24065380 A2 | 3/2004 |
| RU | 2107459 | 3/1998 |
| WO | WO9222259 A2 | 12/1992 |
| WO | WO9622057 | 7/1996 |
| WO | WO9714362 A1 | 4/1997 |
| WO | WO9734536 A2 | 9/1997 |
| WO | WO9918866 A1 | 4/1999 |
| WO | WO9921500 A1 | 5/1999 |
| WO | WO0067651 A1 | 11/2000 |
| WO | WO0108571 A1 | 2/2001 |
| WO | WO0162168 A2 | 8/2001 |
| WO | WO0207901 A1 | 1/2002 |
| WO | WO0234120 A2 | 5/2002 |
| WO | WO02076311 A2 | 10/2002 |
| WO | WO03026482 A2 | 4/2003 |
| WO | WO03066147 A1 | 8/2003 |
| WO | WO2004002331 A1 | 1/2004 |
| WO | WO2004028351 A2 | 4/2004 |
| WO | WO2004043272 A1 | 5/2004 |
| WO | WO2004056267 A1 | 7/2004 |
| WO | WO2004078066 A2 | 9/2004 |
| WO | WO2004080316 A1 | 9/2004 |
| WO | WO2004096080 A2 | 11/2004 |
| WO | WO2005009300 A1 | 2/2005 |
| WO | WO2005057467 A2 | 6/2005 |
| WO | WO2005077282 A1 | 8/2005 |
| WO | WO2005089433 A2 | 9/2005 |
| WO | WO2006009705 A2 | 1/2006 |
| WO | WO2006015302 A1 | 2/2006 |
| WO | WO2006017507 A2 | 2/2006 |
| WO | WO2006039279 A2 | 4/2006 |
| WO | WO2006042206 A2 | 4/2006 |
| WO | WO2006044727 A2 | 4/2006 |
| WO | WO2006047598 A1 | 5/2006 |
| WO | WO2006058079 A3 | 6/2006 |
| WO | WO2006058195 A2 | 6/2006 |
| WO | WO2006062555 A2 | 6/2006 |
| WO | WO2006086241 A2 | 8/2006 |
| WO | WO2006099285 A2 | 9/2006 |
| WO | WO2006102085 A2 | 9/2006 |
| WO | WO2007008709 A2 | 1/2007 |
| WO | WO2007021588 A1 | 2/2007 |
| WO | WO2007022194 A2 | 2/2007 |
| WO | WO2007059343 A2 | 2/2007 |
| WO | WO2007067632 A2 | 6/2007 |
| WO | WO2008008898 A2 | 1/2008 |
| WO | WO2008157513 A1 | 12/2008 |
| WO | WO2009012265 A2 | 1/2009 |
| WO | WO2009018220 A1 | 2/2009 |
| WO | WO2009021116 A2 | 2/2009 |
| WO | WO2009036156 A1 | 3/2009 |
| WO | WO2009046046 A1 | 4/2009 |
| WO | WO2009058566 A1 | 5/2009 |
| WO | WO2009151926 A2 | 12/2009 |
| WO | WO2010014538 | 4/2010 |

OTHER PUBLICATIONS

Bleich et al.; U.S. Appl. No. 12/984,162 entitled "Devices and Methods for Tissue Access", filed Jan. 4, 2011.

Schmitz et al.; U.S. Appl. No. 12/917,253; entitled "Tissue Access Guidewire System and Method"; filed Nov. 1, 2010.

Wallace et al.; U.S. Appl. No. 13/007,381 entitled "Tissue Modification Devices", filed Jan. 14, 2011.

Mopec Bone-Cutting tool, Product brochure, Total pp. 4. First accessed Dec. 15, 2005.

Edwards et al; "T-Saw Laminoplasty for the Management of Cervical Spondylotic Myelopathy," SPINE, Lippincott Williams & Wilkins, Inc., 2000, vol. 25 (14): 1788-1794. Jan. 1, 2000.

Honl et al; "The Use of Water-Jetting Technology in Prostheses Revision Surgery—First Results of Parameter Studies on Bone and Bone Cement," J. Biomed Mater Res (Applied Biomaterials), John Wiley & Sons, Inc, 2000, 53, 6: 781-790. Jan. 1, 2000.

Jun, Byung-Yoon, "Posterior Lumbar Interbody Fusion With Restoration of Lamina and Facet Fusion," SPINE, Lippincott Williams & Wilkins, Inc., 2000, vol. 25 No. 8, 917-922. Jan. 1, 2000.

Abdel-Wanis et al., "Tumor growth potential after tumoral and instrumental contamination: an in-vivo comparative study of T-saw, Gigli saw, and scalpel," Journal of orthopaedic science, 2001, vol. 6, 424-429. Jan. 1, 2001.

Cadman Laminectomy Shaver (a Johnson & Johnson company www.codman.com) catalogue, pp. 416-431, [online] Retrieved from the internet: <URL: http:IIwww.codman.com/PDFs/Cataloa 04 R.pdf >. Jan. 1, 2001.

Ellman Int. Disc-FX System Accessories K052241 [online] Retrieved from the Internet: <URL: http://www.ellman.com/medical/ >. Jan. 1, 2001.

Hara et al., "En Bloc Laminoplasty Performed with Threadwire Saw: Technical Note," Neurosurgery, Jan. 2001, vol. 48, No. 1, pp. 235-239. Jan. 1, 2001.

Hata et al; "A less invasive surgery for rotator cuff tear: Mini-open repair," Journal of Shoulder and Elbow Surciery, 2001, vol. 10 No. 1, 11-16. Jan. 1, 2001.

Integra Ruggles TM Kerrison Rongeurs [online] Retrieved from the internet: <URL: http://www.inteqra-Is.com/products!? product=22>. Jan. 1, 2001.

US Surgical Kerrison Spinal Rongeur K943116 [online] Retrieved from the internet: <URL: http://www.ussurg.com/uss/index.html>. Jan. 1, 2001.

Sen, Cengiz, Tibia proksimalinde Gigli testeresi ile yapilanperkutan osteotominin guvenilirligi: Kadavra calismasi, Acta orthopaedica et traurnatologica turcica, 2002, vol. 36, 136-140; (In Russian w/ Eng Summary). Jan. 1, 2002.

Shiraishi T., "A new technique for exposure of the cervical spine laminae," Journal of neurosurgery. Spine, 2002, vol. 96(1), 122-126. Jan. 1, 2002.

Shiraishi T., Skip laminectomy—a new treatment for cervical spondylotic myelopathy, preserving bilateral muscular attachments to the spinous processes: a oreliminary report, Spine, 2002, vol. 2(2), 108-115. Jan. 1, 2002.

Tomita et al., "The Use of the T-Saw for Expansive Midline laminoplasty in the Treatment of Cervical Myelopathy," Orthopedics and Traumatology, No. 3, pp. 169-178, 2002 Jan. 1, 2002.

Martin-Benlloch et al., "Expansive Laminoplasty as a Method for Managing Cervical Multilevel Spondylotic Myelopathy," Spine, Lippincott Williams & Wilkins, Inc., 2003, vol. 28 No. 7, 680-684. Jan. 1, 2003.

Miyamoto et al., "Kyphectomy Using a Surgical Threadwire (T-saw) for Kyphotic Deformity in a Child With Myelomeningocele," SPINE, Lippincott Williams & Wilkins, Inc., 2003, vol. 28 No. 10, E187-E190. Jan. 1, 2003.

Shiraishi et al., "Results of Skip Laminectomy—Minimum 2-Year Follow-up Study Compared With Open-Door Laminoplasty," Spine, Lippincott Williams & Wilkins, Inc., 2003, vol. 28 No. 24, 2667-2672. Jan. 1, 2003.

Takada et al., "Unusual Metastasis to the Cauda Equina From Renal Cell Carcinoma," SPINE, Lippincott Williams & Wilkins, Inc., 2003, vol. 28 No. 6, E114-E117. Jan. 1, 2003.

(56) References Cited

OTHER PUBLICATIONS

Eralp et al., "A comparison of two osteotomy techniques for tibial lengthening," Archives of orthopaedic and trauma surqerv, 2004, vol. 124:298-300. Jan. 1, 2004.
Skippen et al., "The Chain Saw—A Scottish Invention," Scottish Medical Journal, 2004, vol. 49(2), 72-75. Jan. 1, 2004.
Bohinski et al., "Novel use of a threadwire saw for high sacral amputation," Journal of neurosurnerv: Spine, 2005, vol. 3, 71-78. Jan. 1, 2005.
Nakagiri et al., "Thoracoscopic Rib Resection Using a Gigli Saw," The Annals of Thoracic Surgery, 2005, vol. 80, 755-756. Jan. 1, 2005.
Osaka et al., "Clinical significance of a wide excision policy for sacrococcygeal chordoma," J Cancer Res Clin Oncol, 2005, Total pp. 6. Jan. 1, 2005.
Fessler Richard G, "Minimally Invasive Microendoscopic Decompressive Laminotomy for Lumbar Stenosis," American Association of Neurological Surgeons, 2006, Online CME course, [Retrieved on Jun. 29, 2006 from the internet http://www.aans.emedtrain.com/lumbar ste Jan. 1, 2006.
Park et al; "Cases of the Excision of Carious Joints," John Scrymgeour, Glasgow, 1806, Total pp. 6. Jan. 1, 1806.
Pancoast, Joseph, "A Treatise on Operative Jan. 1, 1844 Surgery," Carey and Hart, Philadelphia,1844, Total pp. 11. Jan. 1, 1844.
Truax, Charles, "The Mechanics of Surgery," Chicago, IL; 1899, Total pp. 3. Jan. 1, 1899.
Burrows, Harold, "Surgical instruments and appliances used in operations," Faber and Faber, London, 1937, total pp. 4. Jan. 1, 1937.
Wilkins, Robert H, "Neurosurgical Classics," Johnson Reprint Corporation, New York, 1965, 377-382. Jan. 1, 1965.
Dammann, Gordon, Pictorial Encyclopedia of Civil War Medical Instruments and Equipment, Pictorial Histories Publishing Company, Missoula, Montana, 1983, Total pp. 2. Jan. 1, 1983.
Barer Malvin, "Instrument to Enhance Passage of the Gigli Saw," Journal of Pediatric Orthopedics, Raven Press, New York, 1984, 4:762-763. Jan. 1, 1984.
Paley et al., "Percutaneous Osteotomies," Orthopedic Clinics of North America, 1991, vol. 22 No. 4, 613-624. Jan. 1, 1991.
Paktiss et al., "Afghan Percutaneous Osteotomy," Journal of Pediatric Orthopaedics, Raven Press Ltd, New York, 1993, vol. 13 No. 4, 531-533. Jan. 1, 1993.
Peltier, Leonard Orthopedics: A History and Iconography, Norman Publishing, San Francisco, 1993, Total pp. 3. Jan. 1, 1993.
Rutkow, Ira, "Surgery an Illustrated History," Mosby-Year Book, Inc., St. Louis, 1993, Total pp. 4. Jan. 1, 1993.
Goel, Atul, "Neurosurgical forum, Supraorbital Craniotomy," Journal of Neurosurgery, 1994, vol. 81, 642-643. Jan. 1, 1994.
Tomita et al., "Total en bloc spondylectomy and circumspinal decompression for solitary spinal metastasis," Paraplegia, 1994, 32:36-46. Jan. 1, 1994.
Tomita K. et al., "Total en bloc spondylectomy for solitary spinal metastases," International Orthopaedics (SICOT), 1994, 18: 291-298. Jan. 1, 1994.
Brunori et al., "Celebrating the centennial (1894-1994): Leonardo Gigli and his wire saw," J. Neurosun:i, 1995, 82:1086-1090. Jan. 1, 1995.
Tomita et al., "The Threadwire Saw: a New Device for Cutting Bone," The Journal of Bone and Joint Surgery, 1996, vol. 78, 1915-1917. Jan. 1, 1996.
Baumgart et al., "Indikation and Technik der Knochendurchtrennung," Der Chirura, 1998, vol. 69:1188-1196. (in German with Eng Summary). Jan. 1, 1998.
Stevens et al., "Calvarial Bone Graft Harvest Using the Gigli Saw," Journal of Oral and Maxillofacial Surgery, 1998, vol. 56, 798-799. Jan. 1, 1998.
Tomita et al., "Expansive Midline T-Saw Laminoplasty (Modified Spinour Process-Splitting) for the Management of Cervical Myelopathy," SPINE, Lippincott Williams & Wilkins, Inc, 1998, 23(1), 32-37. Jan. 1, 1998.
Fujita et al., "Chordoma in the Cervical Spine Managed with En Bloc Excision," SPINE, Lippincott Williams & Wilkins, Inc., 1999, 24 (17), 1848-1851. Jan. 1, 1999.
Gore Smoother User Manual, W. L. Gore & Associates, Inc. Flagstaff, AZ., Dec. 1999, Total pp. 3. Jan. 1, 1999.
Kawahara et al., "Recapping T-Saw Laminoplasty for Spinal Cord Tumors," SPINE, 1999, vol. 24 No. 13, DD. 1363-1370. Jan. 1, 1999.
Peavy et al., "Comparison of Cortical Bone Ablations by Using Infrared Laser Wavelengths 2.9 to 9.2 μm, Lasers in Surgery and Medicine," 1999, vol. 26, 421-434. Jan. 1, 1999.
Zeppelin Laminectomy Rongeur K901372, [online] Retrieved from the Internet: <URL: http://www.zeppelin-medical.com/download/instruments.pdf>. Oct. 24, 2006.
Reckling Frederick, "Modified Stethoscope Earpiece Makes Excellent Gigli Saw Guide," J Bone and Joint Surgery Am, Dec. 1972, 54-A{8}, 1787-1788. Dec. 1, 1972.
Schwieger et al., "Abrasive Water Jet Cutting as a New Procedure for Cutting Cancellous Bone-In Vitro Testing in Comparison with the Oscillating Saw," Wiley Interscience, www.interscience,wiley.com, Sep. 20, 2004, 223-228. 9120104.
Bleich et al.; U.S. Appl. No. 14/180,221 entitled "Flexible tissue rasp," filed Feb. 13, 2014.
Schmitz et al.; U.S. Appl. No. 14/195,197 entitled "Tissue modification devices," filed Mar. 3, 2014.
Leguidleguid et al.; U.S. Appl. No. 14/209,418 entitled "Tissue Modification Devices," filed Mar. 13, 2014.
Schmitz et al.; U.S. Appl. No. 14/023,893 entitled "Tissue Access Guidewire System and Method," filed Sep. 11, 2013.
Leguidleguid et al.; U.S. Appl. No. 14/061,641 entitled "Tissue Modification Devices," filed Oct. 23, 2013.
Schmitz et al.; U.S. Appl. No. 14/064,085 entitled "Access and Tissue Modification Systems and Methods," filed Oct. 25, 2013.
Herkowitz, "The Cervical Spine Surgery Atlas", 2004, Lippincott Williams & Wilkins; 2nd Edition; pp. 203-206, & 208; Dec. 2003.
Ohta et al., "Superimposed Mechanomyographic Response at Different Contraction Intensity in Medial Gastrocnemius and Soleus Muscles," International Journal of Sport and Health Science: vol. 5, 63-70, Nov. 2007.
Wallace et al.; U.S. Appl. No. 13/728,767 entitled "Devices, systems and methods for tissue modification," filed Dec. 27, 2012.

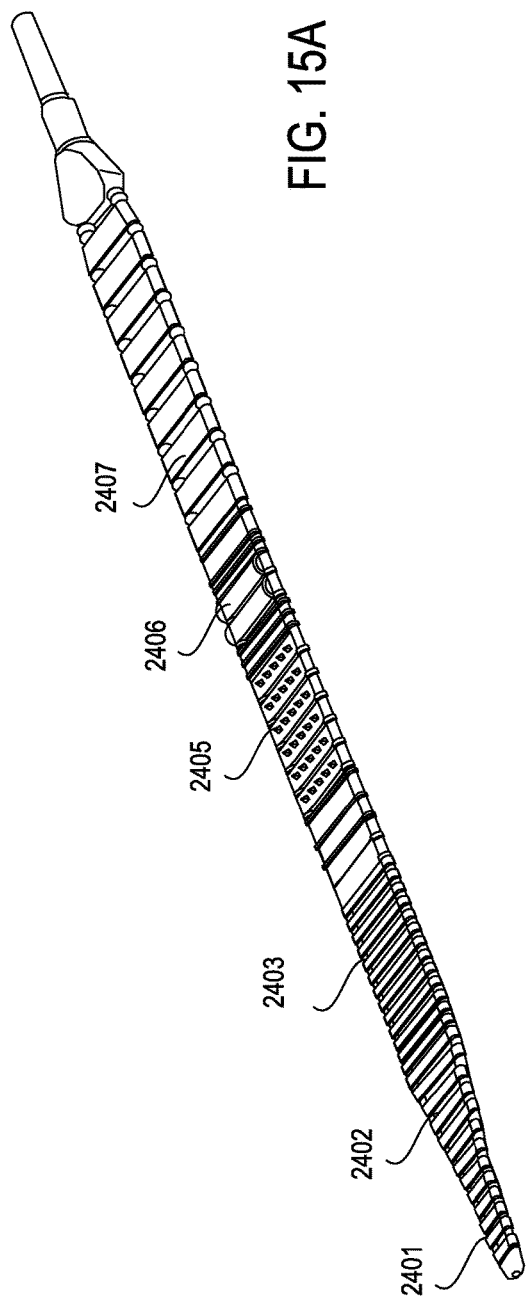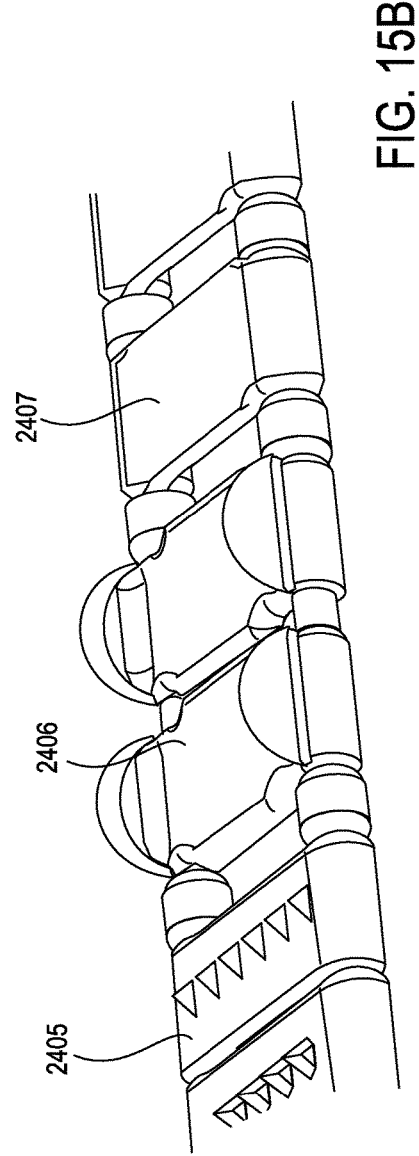

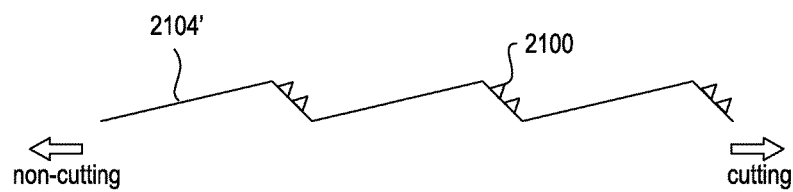
FIG. 27
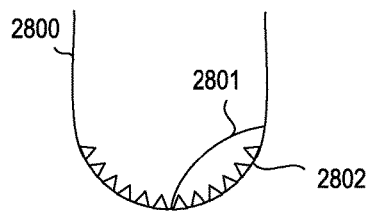 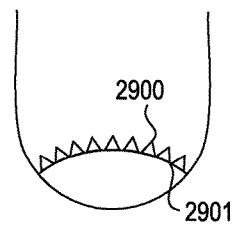 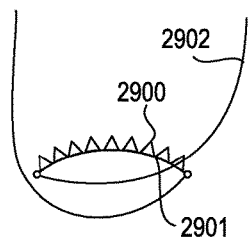
FIG. 28  FIG. 29A  FIG. 29B
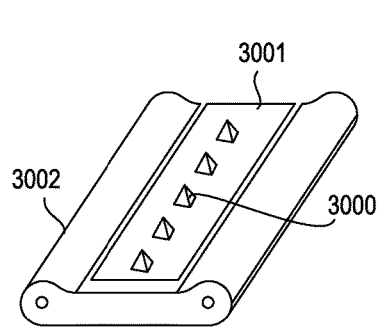 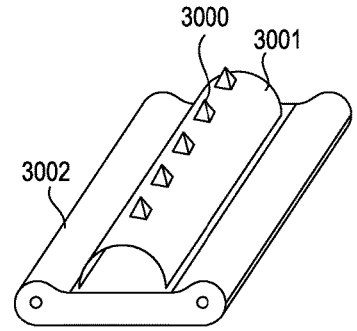
FIG. 30A  FIG. 30B

DEVICES AND METHODS FOR TREATING TISSUE

RELATED APPLICATIONS

This application is a division of U.S. patent application Ser. No. 12/911,537 filed on Oct. 25, 2010 entitled "DEVICES AND METHODS FOR TREATING TISSUE". Application Ser. No. 12/911,537 is a continuation-in-part to U.S. patent application Ser. No. 11/251,205, titled "DEVICES AND METHODS FOR TISSUE ACCESS", filed on Oct. 15, 2005, now U.S. Pat. No. 7,918,849 issued on Apr. 5, 2011. U.S. Pat. No. 7,918,849 claims the benefit of U.S. Provisional Patent Application No. 60/619,306, filed Oct. 15, 2004, U.S. Provisional Patent Application No. 60/622,865, filed Oct. 28, 2004, U.S. Provisional Patent Application No. 60/681,719, filed May 16, 2005, U.S. Provisional Patent Application No. 60/681,864, filed May 16, 2005, and U.S. Provisional Patent Application No. 60/685,190, filed May 27, 2005, each of which is incorporated by reference herein in its entirety.

U.S. patent application Ser. No. 12/911,537 is a continuation-in-part to U.S. patent application Ser. No. 11/468,247, titled "TISSUE ACCESS GUIDEWIRE SYSTEM AND METHOD", filed on Aug. 29, 2006, now U.S. Pat. No. 7,857,813 issued on Dec. 28, 2010. This application is herein incorporated by reference in its entirety.

U.S. Ser. No. 12/911,537 also claims priority to U.S. Provisional Patent Application No. 61/254,656, titled "TISSUE REMOVAL DEVICES AND METHODS", filed on Oct. 23, 2009; U.S. Provisional Patent Application No. 61/260,012, titled "DEVICES AND METHODS FOR DELIVERING HEMOSTATIC AGENTS", filed on Nov. 11, 2009; U.S. Provisional Patent Application No. 61/289,075, titled "DEVICES AND METHODS FOR STOPPING OR PREVENTING BLEEDING", filed on Dec. 22, 2009; U.S. Provisional Patent Application No. 61/388,601, titled "TISSUE REMOVAL DEVICES AND METHODS", filed on Sep. 30, 2010; and U.S. Provisional Patent Application No. 61/325,753, filed Apr. 19, 2010, title "TISSUE MODIFICATION DEVICES"; each of these applications is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD OF THE INVENTION

Described herein are systems, devices, and methods of using them, for performing surgical procedures. In particular, described herein are systems, devices and methods for spinal decompression procedures.

BACKGROUND OF THE INVENTION

A significant number of surgical procedures involve modifying tissue in a patient's body, such as by removing, cutting, shaving, abrading, shrinking, ablating or otherwise modifying tissue. Minimally invasive (or "less invasive") surgical procedures often involve modifying tissue through one or more small incisions or percutaneous access, and thus may be more technically challenging procedures. Some of the challenges of minimally invasive tissue modification procedures include working in a smaller operating field, working with smaller devices, and trying to operate with reduced or even no direct visualization of the tissue (or tissues) being modified. For example, using arthroscopic surgical techniques for repairing joints such as the knee or the shoulder, it may be quite challenging to modify certain tissues to achieve a desired result, due to the required small size of arthroscopic instruments, the confined surgical space of the joint, lack of direct visualization of the surgical space, and the like. It may be particularly challenging in some surgical procedures, for example, to cut or contour bone or ligamentous tissue with currently available minimally invasive tools and techniques. For example, trying to shave a thin slice of bone off a curved bony surface, using a small-diameter tool in a confined space with little or no ability to see the surface being cut, as may be required in some procedures, may be incredibly challenging or even impossible using currently available devices.

One area of surgery which would likely benefit from the development of less invasive techniques is the treatment of spinal stenosis. Spinal stenosis occurs when nerve tissue and/or the blood vessels supplying nerve tissue in the spine become impinged by one or more structures pressing against them, causing symptoms. The most common form of spinal stenosis occurs in the lower (or lumbar) spine and can cause severe pain, numbness and/or loss of function in the lower back and/or one or both lower limb.

For example, as shown in FIG. 1 which shows the lateral aspect of a facet joint complex, there are several arteries that may bleed during a decompression of this spinal region. The facet joint complex includes a superior articular process (SAP) and an inferior articular process (IAP). In some embodiments, it is desirable to remove tissue below (ventral) the SAP and/or the bottom (ventral) portions of the SAP while avoiding the tissue on the lateral side of the SAP (the area labeled SAP in FIG. 1). Although not shown, two nerve roots branching from the cauda equina exit the central spinal canal and extend through intervertebral foramina on either side of the vertebra. Spinal stenosis can occur when the spinal cord, cauda equina and/or nerve root(s) are impinged by one or more tissues in the spine, such as buckled or thickened ligamentum flavum, hypertrophied facet joint (shown as superior articular processes in FIG. 1), osteophytes (or "bone spurs") on vertebrae, spondylolisthesis (sliding of one vertebra relative to an adjacent vertebra), facet joint synovial cysts, and/or collapse, bulging or herniation of an intervertebral disc. Impingement of neural and/or neurovascular tissue in the spine by one or more of these tissues may cause pain, numbness and/or loss of strength or mobility in one or both of a patient's lower limbs and/or of the patient's back.

In the United States, spinal stenosis occurs with an incidence of between 4% and 6% (or more) of adults aged 50 and older and is the most frequent reason cited for back surgery in patients aged 60 and older. Patients suffering from spinal stenosis are typically first treated with conservative approaches such as exercise therapy, analgesics, anti-inflammatory medications, and epidural steroid injections. When these conservative treatment options fail and symptoms are severe, as is frequently the case, surgery may be required to remove impinging tissue and decompress the impinged nerve tissue.

Lumbar spinal stenosis surgery involves first making an incision in the back and stripping muscles and supporting structures away from the spine to expose the posterior aspect of the vertebral column. Thickened ligamentum flavum is then exposed by complete or partial removal of the bony arch (lamina) covering the back of the spinal canal (laminectomy or laminotomy). In addition, the surgery often includes partial or complete facetectomy (removal of all or part of one or more facet joints), to remove impinging ligamentum flavum or bone tissue. Spinal stenosis surgery is performed under general anesthesia, and patients are usually admitted to the hospital for five to seven days after surgery, with full recovery from surgery requiring between six weeks and three months. Many patients need extended therapy at a rehabilitation facility to regain enough mobility to live independently.

Removal of vertebral bone, as occurs in laminectomy and facetectomy, often leaves the affected area of the spine very unstable, leading to a need for an additional highly invasive fusion procedure that puts extra demands on the patient's vertebrae and limits the patient's ability to move. Unfortunately, a surgical spine fusion results in a loss of ability to move the fused section of the back, diminishing the patient's range of motion and causing stress on the discs and facet joints of adjacent vertebral segments. Such stress on adjacent vertebrae often leads to further dysfunction of the spine, back pain, lower leg weakness or pain, and/or other symptoms. Furthermore, using current surgical techniques, gaining sufficient access to the spine to perform a laminectomy, facetectomy and spinal fusion requires dissecting through a wide incision on the back and typically causes extensive muscle damage, leading to significant post-operative pain and lengthy rehabilitation. Thus, while laminectomy, facetectomy, and spinal fusion frequently improve symptoms of neural and neurovascular impingement in the short term, these procedures are highly invasive, diminish spinal function, drastically disrupt normal anatomy, and increase long-term morbidity above levels seen in untreated patients.

Therefore, it would be desirable to have less invasive methods and devices for modifying target tissue in a spine to help ameliorate or treat spinal stenosis, while inhibiting unwanted damage to non-target tissues such as nerves and blood vessels. Ideally, such techniques and devices would reduce neural and/or neurovascular impingement without removing significant amounts of vertebral bone, joint, or other spinal support structures, thereby avoiding the need for spinal fusion and, ideally, reducing the long-term morbidity resulting from currently available surgical treatments. It may also be advantageous to have minimally invasive or less invasive tissue modification devices capable of treating target tissues in parts of the body other than the spine.

Described herein are devices, systems and methods that may address many of the problems and identified needs described above.

SUMMARY OF THE INVENTION

Described herein are devices, systems and methods for treating target tissue in a patient's spine. In general the method include the steps of advancing a wire into the patient from a first location, through a neural foramen, and out of the patient from a second location; connecting a tissue modification device to the wire; positioning the tissue modification device through the neural foramen using the wire; modifying target tissue in the spine by moving the tissue modification device against the target tissue; and delivering an agent to modified target tissue, wherein the agent is configured to inhibit blood flow from the modified target tissue.

In some embodiments, the step of advancing a wire includes advancing the wire around at least part of a target tissue and out of the patient from the second location, so that both ends of the wire are external to the patient. In some embodiments, the step of positioning the tissue modification device includes pulling the wire to position the tissue modification device. While in some embodiments, the step of positioning the tissue modification device includes positioning the tissue modification device such that cutting edges on the device are positioned adjacent to the tissue to be treated. In some embodiments, the step of modifying tissue includes pulling on the end of the wire extending from the second location to move the tissue modification device against the tissue.

In some embodiments, the step of delivering an agent to the modified target tissue includes delivering an agent to the modified target tissue through a delivery device. In some embodiments, the delivery device is a cannula having an atraumatic tip. In some embodiments, the delivery device includes a radio opaque marker at a distal end of the device. In some embodiments, the method further includes the step of coupling a syringe to the delivery device. In some embodiments, the method further includes the step of providing suction and irrigation to the modified target tissue through the delivery device.

In some embodiments, the method further includes the step of positioning the delivery device using the wire. In some embodiments, the step of positioning the delivery device includes threading the delivery device over the wire. In some embodiments, the step of positioning the delivery device includes connecting the distal end of the delivery device to the proximal end of the wire. In some embodiments, the step of positioning the delivery device includes positioning the delivery device through the neural foramen. In some embodiments, the step of positioning the delivery device includes positioning the delivery device through an interlaminar window.

In some embodiments, the step of positioning the delivery device includes positioning a catheter of the delivery device, wherein the catheter includes a distal end and a proximal end, wherein the proximal end includes a connector. In some embodiments, the step of positioning the delivery device includes positioning the distal end of the catheter adjacent to the modified target tissue while the connector remains outside of the patient. In some embodiments, the step of positioning the delivery device includes removably locking the delivery device onto the wire with the connector. In some embodiments, the agent is at least one of a haemostatic agent, a tissue sealant, a vasoconstrictor, a corticosteroid, a local anesthetic, an analgesic, and any combination thereof.

In some embodiments, in general the method include the steps of advancing a wire into the patient from a first location, through a neural foramen adjacent to a facet joint having a superior articular process, and out of the patient from a second location; connecting a tissue modification device to the wire; positioning the tissue modification device through the neural foramen using the wire; and modifying target tissue in the spine by moving the tissue modification device against the target tissue to remove target tissue located ventral to the superior articular process while avoiding non-target tissue located lateral to the superior articular process.

In some embodiments, the step of advancing a wire includes advancing the wire through the neural foramen and away from a lateral aspect of the superior articular process. In some embodiments, the step of advancing a wire includes advancing the wire through a probe having an inner cannula and an outer cannula. In some embodiments, the method further includes the step of advancing the inner cannula out of the outer cannula to a position such that a distal tip of the inner cannula points away from a lateral aspect of the superior articular process.

In some embodiments, the tissue modification device includes an elongate body having a stiffness that varies along the length of the elongate body. In some embodiments, the distal portion of the elongate body has a stiffness that is greater than the proximal portion such that the distal portion of the elongate body does not wrap around a lateral aspect of the superior articular process. In some embodiments, the step of modifying tissue includes reciprocating the tissue modification device against the target tissue by alternately pulling on the end of the wire extending from the first location and a proximal end of the tissue modification device extending from the second location.

In some embodiments, the step of modifying tissue includes reciprocating the tissue modification device such that the tissue modification device is reciprocated against target tissue located ventral to the superior articular process and not reciprocated against non-target tissue located lateral to the superior articular process. In some embodiments, a distal handle is coupled to the end of the wire extending from the second location and the tissue modification device includes a proximal handle positioned outside of the patient at the first location. In some embodiments, the step of modifying tissue includes holding the distal handle and the proximal handle a distance apart from one another such that the tissue modification device is not reciprocated against the non-target tissue located lateral to the superior articular process. In some embodiments, the step of modifying tissue includes holding the distal handle and the proximal handle a distance apart from one another such that the such that the wire extending from the second location is not parallel to the tissue modification device.

In general, a device for delivering an agent to tissue in a patient's spine includes a elongate flexible catheter having a proximal end and a distal end, wherein the distal end of the elongate catheter is configured to be advanced into the patient from a first location and toward a neural foramen; a connector coupled to the proximal end of the catheter that remains outside of the patient and is configured to receive a syringe containing an agent; and an aperture at the distal end portion of the catheter configured to deliver the agent to the tissue.

In general a kit having a device for delivering an agent to tissue in a patient's spine includes a catheter and a connector, wherein the connector is configured to couple to a guidewire, a catheter, and a syringe. In some embodiments, the kit further includes a syringe having a hemostatic agent, wherein the syringe configured to couple to the connector. In some embodiments, the kit further includes a guidewire configured to couple to the connector. In some embodiments, the kit further includes a guidewire delivery probe. In some embodiments, the kit further includes a tissue modification device.

BRIEF DESCRIPTION OF THE DRAWINGS

FIGS. 11-15B show various components and configurations of tissue modification devices.

FIGS. 26-27 show various configurations where the tissue modification device cuts when it is reciprocated in a first direction and does not cut when it is reciprocated in the second direction.

FIGS. 28-30B show various configurations wherein a substrate or shield bends to move the blades toward or away from the tissue.

DETAILED DESCRIPTION OF THE INVENTION

The devices, systems and methods described herein may be use in any appropriate surgical procedure, particularly for the surgical treatment of spinal stenosis. For example, described herein are systems including one or more of the following devices: a guidewire, a probe for positioning a guidewire, and a tissue modification device for use with the guidewire. As described herein, the systems and methods may be used to decompress one or more spinal regions. In particular, any of these devices may be used to decompress nerve roots within the spinal anatomy along various paths. Because these devices are flexible, and may be appropriately sized and shaped to fit within a neural foramen, these devices may be used to accesses appropriate regions of the spine from a single access point (e.g., from the patient's midline or near-midline region). While the systems and methods described herein may used to decompress one or more spinal regions they may also be configured to avoid portions of the vascular anatomy or other non target tissue within the spinal regions that are being decompressed. Furthermore, the devices, systems and methods described herein may be use in any appropriate surgical procedure, particularly for stopping or preventing bleeding during the surgical treatment of spinal stenosis.

Figure 1:
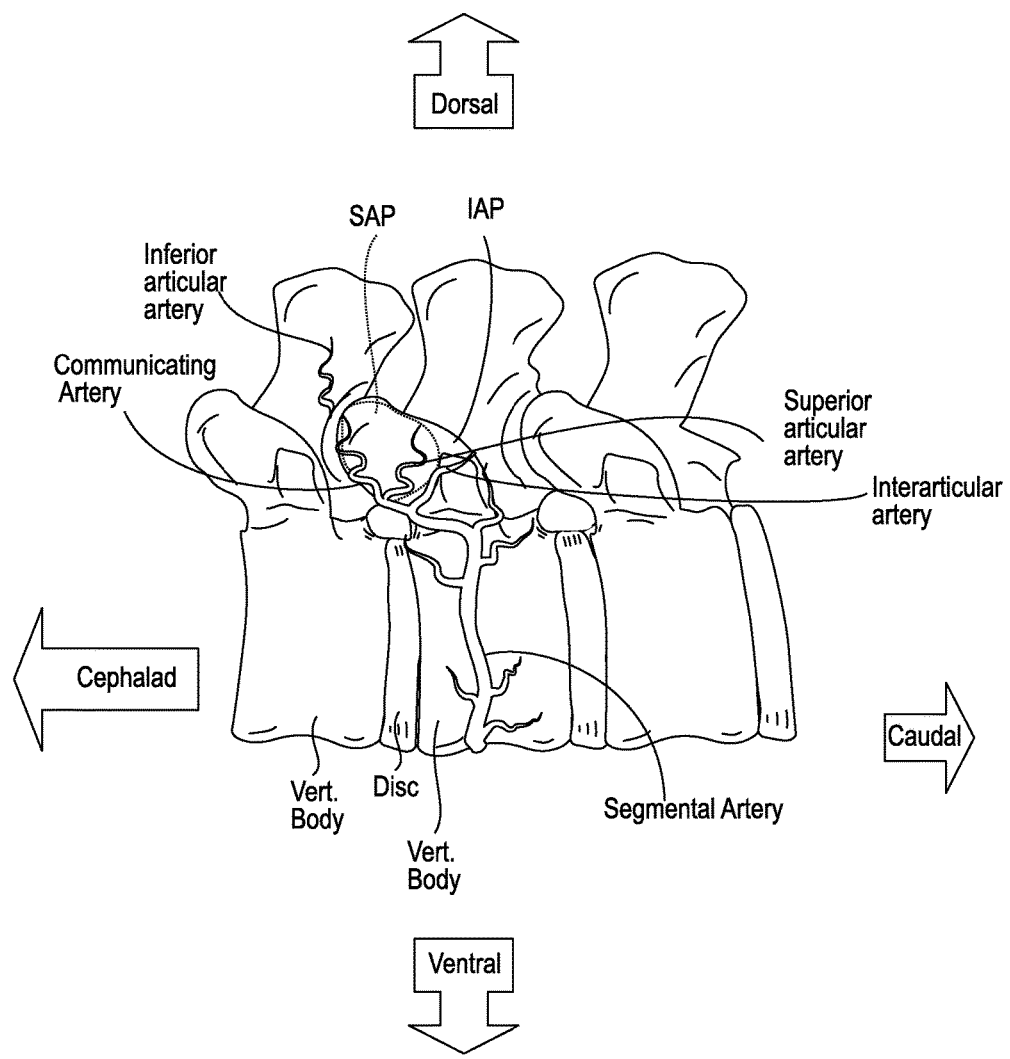
FIG. 1 illustrates the vascular anatomy of a spinal region.

For example, as shown in FIG. 1 which shows the lateral aspect of a facet joint complex, there are several arteries that may bleed during a decompression of this spinal region. Haemostatic agents or other devices or methods for stopping or preventing bleeding may be delivered to an artery or other vessel that has been or may be damaged or ruptured or is otherwise bleeding. The agent will promote homeostasis and stop or prevent unwanted and/or excessive bleeding. Alternatively, vasoconstrictors or vasopressors, such as Epinephrine may be delivered to the surgical site to constrict the surrounding vessels to slow or stop bleeding. In some embodiments, the agent delivered to the surgical site may include a tissue sealant, a steroid, a corticosteroid, a local anesthetic, and/or an analgesic.

A hemostatic agent, which may also be an antihemorrhagic (antihaemorrhagic) agent include substances that promote hemostasis (i.e., to stop bleeding). For example, styptics (also spelled stiptics) are one type of antihemorrhagic agent that work by contracting tissue to seal injured blood vessels. Styptic may include astringents. Antihemorrhagic agents used in medicine may have various mechanisms of action, including inhibiting fibrinolysis or promoting coagulation (particularly in systemic agent), causing vasoconstriction or promoting platelet aggregation (particularly in local agents). Examples of such agents include microfibrillar collagen, chitosan, antiliem01Thagic drugs such as antifibrinolytics, vitamin K, fibrinogen, and blood coagulation factors, anhydrous aluminum sulfate, potassium alum, titanium dioxide, styptic powder, etc. These examples are illustrative only, and any appropriate hemostatic agent may be used with the methods, devices and systems described herein.

For example, as shown in FIG. 1 which shows the lateral aspect of a facet joint complex, there are several arteries at least a portion of which are preferably avoided during a decompression of this spinal region. The facet joint complex includes a superior articular process (SAP) and an inferior articular process (IAP). In some embodiments, it is desirable to remove tissue below (ventral) the SAP and/or the bottom (ventral) portions of the SAP while avoiding the tissue on the lateral side of the SAP (the area labeled SAP in FIG. 1). A tissue modification device (not shown) may be positioned below (ventral) to the SAP to remove tissue in that area while, in some embodiments as described in detail below, avoiding the tissue (including vascular anatomy) on lateral side of the SAP.

As described herein, devices, systems and methods may be configured to stop or prevent the bleeding of non-target tissue, such as blood vessels. For example, the devices, systems and methods may be configured to deliver hemostatic agents or tissue sealants to the non-target tissue. Alternatively or additionally, as described herein, devices, systems and methods may be configured to avoid the tissue (including vascular anatomy) on lateral side of the SAP in one of several variations, as described in detail below. For example, a probe and guidewire may be configured and/or the method of use may be configured such that the guidewire is positioned to avoid the tissue (including vascular anatomy) on lateral side of the SAP. Alternatively, while moving the tissue modification device to remove tissue, the proximal and distal handles of the device may be held a distance apart from one another such that the tissue modification device is positioned and moved to avoid the tissue (including vascular anatomy) on lateral side of the SAP. In a third variation, the tissue modification device may be configured to have a variable stiffness along the length of the device. A more stiff portion of the device will prevent the device from wrapping around the lateral side of the SAP and will therefore not remove tissue (including vascular anatomy) on lateral side of the SAP.

In general, the procedure may be used to decompress spinal nerve roots on the unilateral or contralateral side from the access point. A probe or guide may be introduced into the spinal epidural space (or along or just within the ligamentum flavum) at an appropriate spinal level using image guidance and/or tracking (e.g., electromagnetic tracking). Introduction may be either via percutaneous puncture or open laminotomy.

Figure 2:
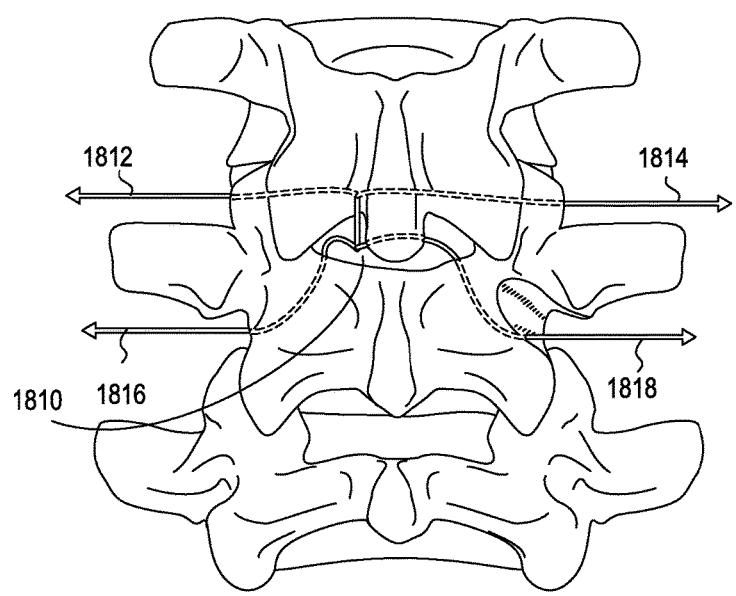
FIG. 2 is a posterior view of the spine indicating decompression paths at disc level and along the nerve root.

As shown in FIG. 2, the device may be used to decompress an ipsilateral or contralateral proximal nerve (in a lateral recess). A guide or probe may be deployed immediately cephalad to the caudal segment pedicle on the appropriate side (e.g., location 1810). This access point can be confirmed radiographically. If neural structures adjacent to the guide cannot be directly visualized, the relationship of these structures to the guide or tissue modification devices can be determined using electrical stimulation, ultrasound imaging, endoscopic mean or other techniques.

As shown in FIG. 2, the guidewire may be threaded along a path from location 1810 to where it exits through the foramen, as shown by at least one of arrows 1812 (for ipsilateral decompression of the nerve root origin at the disc level) and 1814 (for contralateral decompression of the nerve root origin at the disc level). Alternatively, as shown in FIG. 2, the guidewire may be threaded along a path from location 1810 to where it exits through the foramen, as shown by at least one of arrows 1816 (for ipsilateral decompression along the nerve root) and 1818 (for contralateral decompression along the nerve root). In some embodiments, the probe/guide is removed once the guidewire has been positioned.

The guidewire may include a wire exchange tip on its proximal end, as described in more detail below. A flexible tissue modification device is attached to the proximal wire exchange tip, and a distal handle may be secured to guidewire at the distal wire tip. The device can then be introduced into the epidural space and then into the lateral recess by careful upward force applied to the distal handle. In some embodiments, the device is pulled by the guidewire on the path through the spinal anatomy. As described above, suitable paths include paths shown by arrows 1812 and 1814 and/or 1816 and 1818 to decompress the nerve root origin at disc level and/or along the nerve root, respectively.

Figure 3:
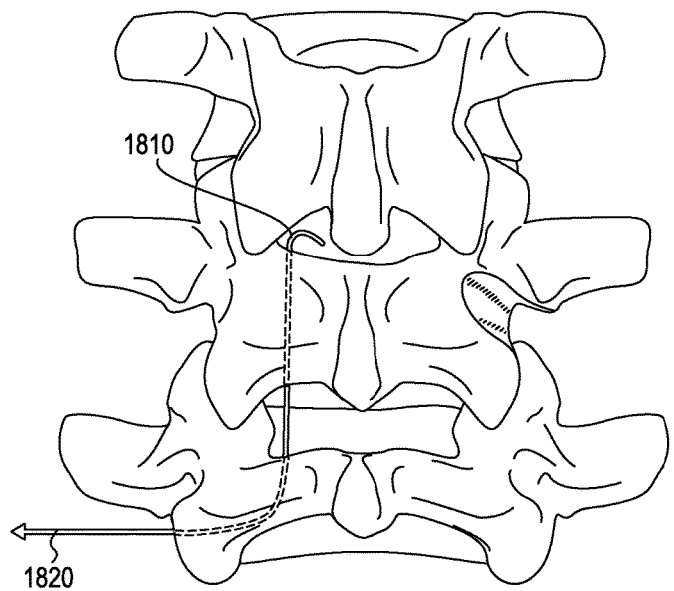
FIG. 3 is a posterior view of the spine indicating a decompression path for adjacent level lateral recess decompression.

Once the device is in place as confirmed visually or radiographically, binlanual reciprocating strokes may be utilized to decompress dorsal impinging bone or soft tissue at the nerve root origin. The probe/guide may be reinserted to decompress the ipsilateral or contralateral distal (foraminal) portion of the nerve root, so that the same (or a different) tissue modification device may be used to decompress another region of the spine (or nerve root) using the same access or entry site. As shown in FIG. 3, the devices described herein can used to decompress the ipsilateral or contralateral (not shown), or both, regions adjacent the level proximal to the nerve root (lateral recess). A guide may be deployed in the same access point (location 1810) as described above. As shown in FIG. 3, the guidewire can then be threaded along a path from location 210 to where it exits through the foramen, as shown by arrow 220 (for ipsilateral decompression of the adjacent nerve root origin).

Guidewire and Probe for Positioning a Guidewire

Figure 4:
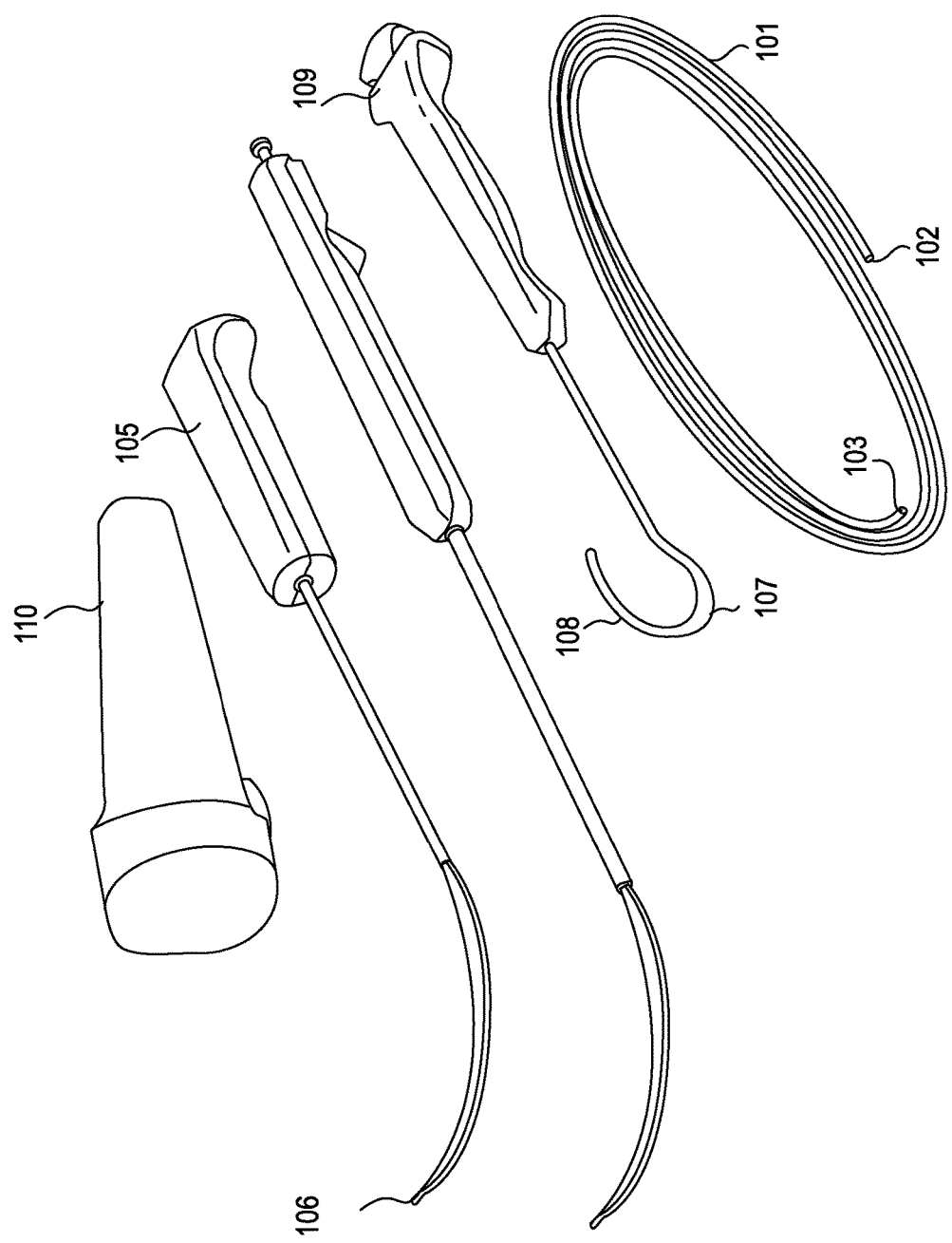
FIG. 4 illustrates a system of devices including a guidewire, a probe for positioning a guidewire, and a tissue modification device for use with the guidewire.

Described herein are systems including one or more of the following devices: a guidewire and a probe for positioning a guidewire. The guidewire 101 shown in FIG. 4 is typically long (e.g., elongated) and flexible, and may have a sharp (tissue penetrating) distal end 103 and a proximal end 102 that allows it to be coupled to a guidewire coupling member securely. For example, in FIG. 4, the guidewire 101 includes a ball or other shaped end (which may be conical, tubular, ring, etc.) secured to the distal end for coupling to a guidewire coupling member. The proximal end 102 may be configured to lock into a guidewire coupling member I 06 at the distal end of a tissue modification device (such as the one 105 indicated in FIG. 4). A guidewire coupler member is configured to attach to a guidewire (e.g., one end of a guidewire) so that the tissue modification device can be manipulated, at least in part, by pulling on the guidewire after the guidewire has been secured to the device. For example, in some variations a guidewire may be inserted into the body from a first location outside of the body, then passed around the target tissue (e.g., around a spinal foramen) and out of the body from a second position. The distal end of the guidewire may then be coupled to the flexible tissue modification device 105 and pulled through the body until the tissue modifying region of the device, e.g., the portion of the device including cutting edges or blades, is positioned opposite the target tissue. In some variations the distal end of the device may be completely withdrawn from the patient, so that it can be grasped and manipulated. In other variations, the distal end of the tissue-modification device remains coupled to the guidewire, and the guidewire may be grasped to manipulate the distal end of the tissue-modification device. A handle 110 may be attached to the distal end of the guidewire. Similarly, the proximal end of the guidewire may be configured to pass through the probe 109 so that the probe may be removed from over the proximal end of the guidewire during operation. In general, the distal end 107 of the probe 109 described herein may be curved or bent, and/or may be curveable or bendable. The outer distal end may be more or less curved. The inner cannula 108 may be configured to bend as it exits the distal end of the outer cannula, as shown, thereby increasing the ability of the probe to guide a guidewire around a target tissue.

Figure 5A:
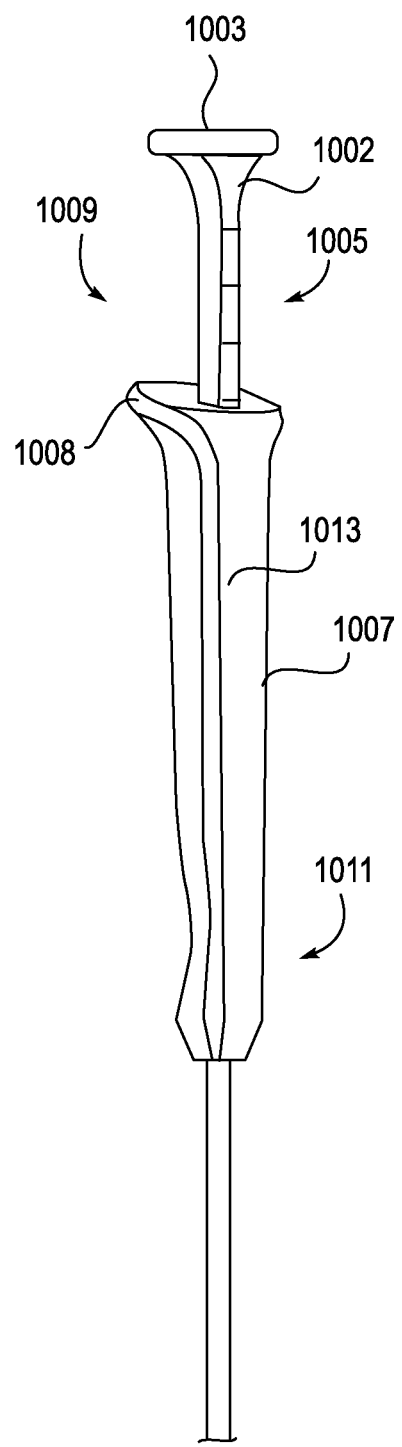
FIGS. 5A and 5B illustrate a probe for positioning a guidewire.
Figure 5B:
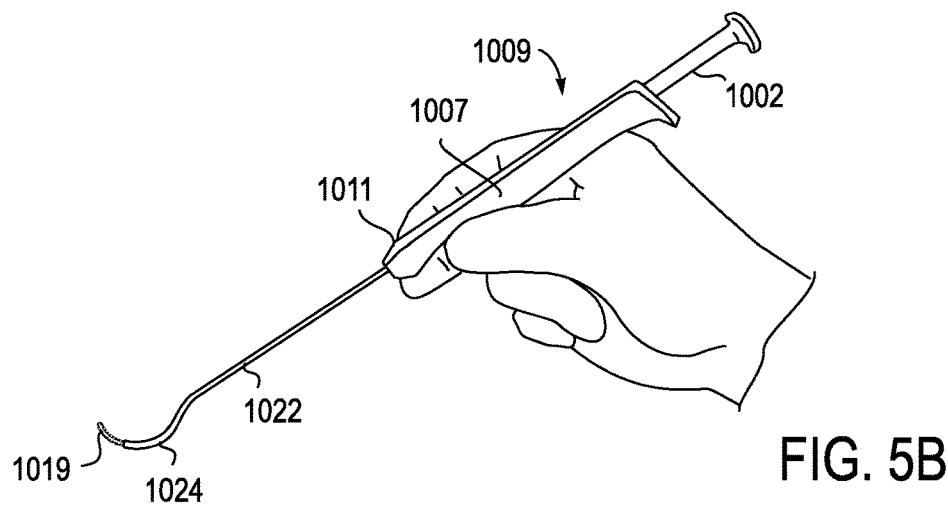

For example, in the variation illustrated in FIGS. 5A and 5B, the probe 1009 includes a handle portion having a pusher or plunger 1002 that communicates with an internal cannula slideably disposed within the external cannula so that the internal cannula may be extended from the distal end of the probe for placement around a target tissue, as illustrated in FIG. 5B. The pusher includes a flanged 1003 proximal end having a finger (e.g., thumb) pushing surface that is perpendicular to the long axis of the device (including the long axis of the handle). As described in greater detail, this proximal end may be formed to more readily allow insertion of a guidewire by guiding the guidewire into the lumen of the inner cannula. The pusher is calibrated 1005 along the side in a top-facing surface. The calibration shown in this example includes markings to indicate depth (e.g., how far down the pusher has been extended), which corresponds to how far out of the distal end the inner cannula is extended. The calibrations may include alphanumeric symbols, colors, textures, or any combination of the like. The calibrations may be referenced to distance (e.g., depth, length, etc.), or they may be un-referenced (as shown in FIG. 5A).

Figure 6A:
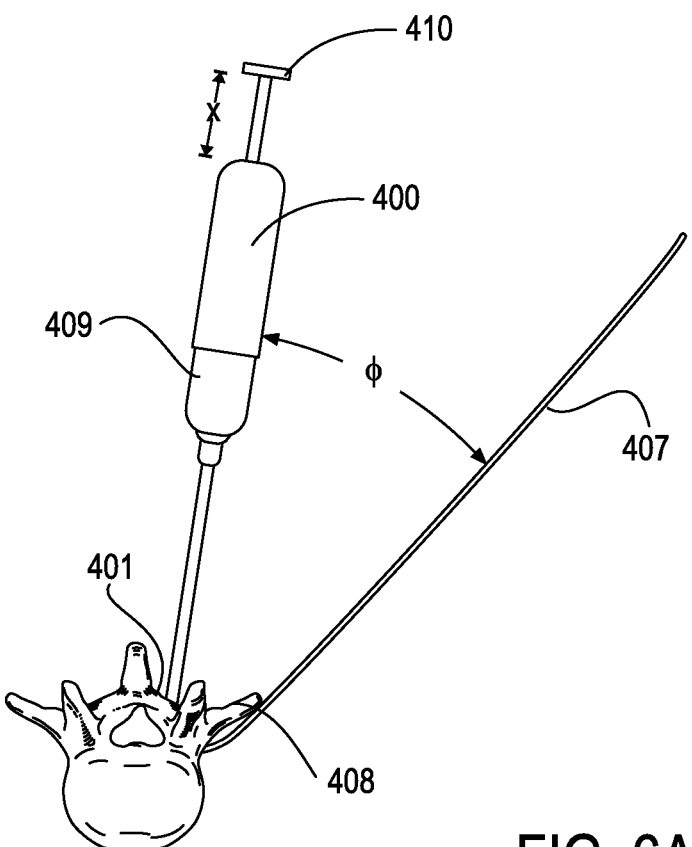
FIGS. 6A-6C and FIG. 7 demonstrate a path of a probe, guidewire, and tissue modification device through a spinal region.
Figure 6B:
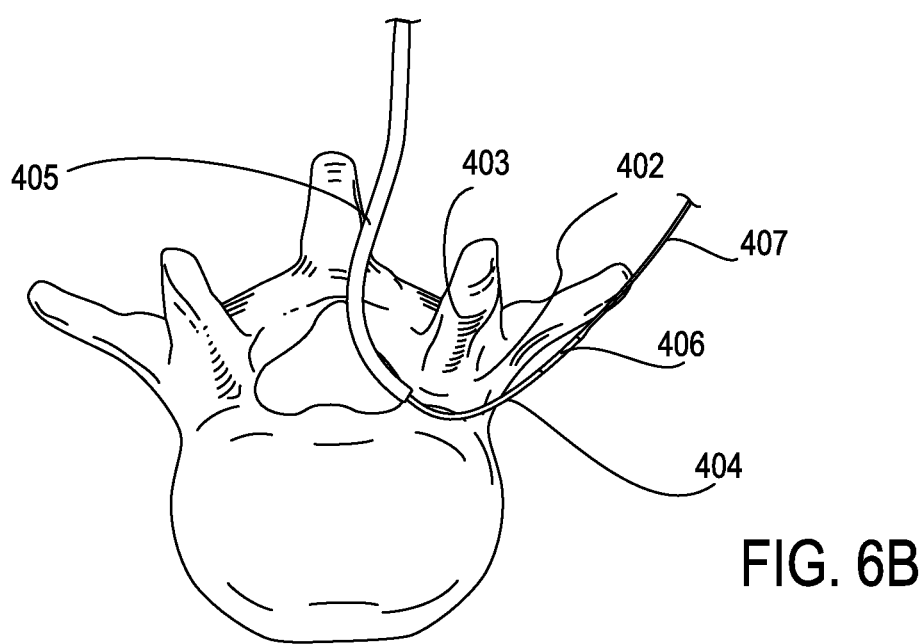
Figure 8A:
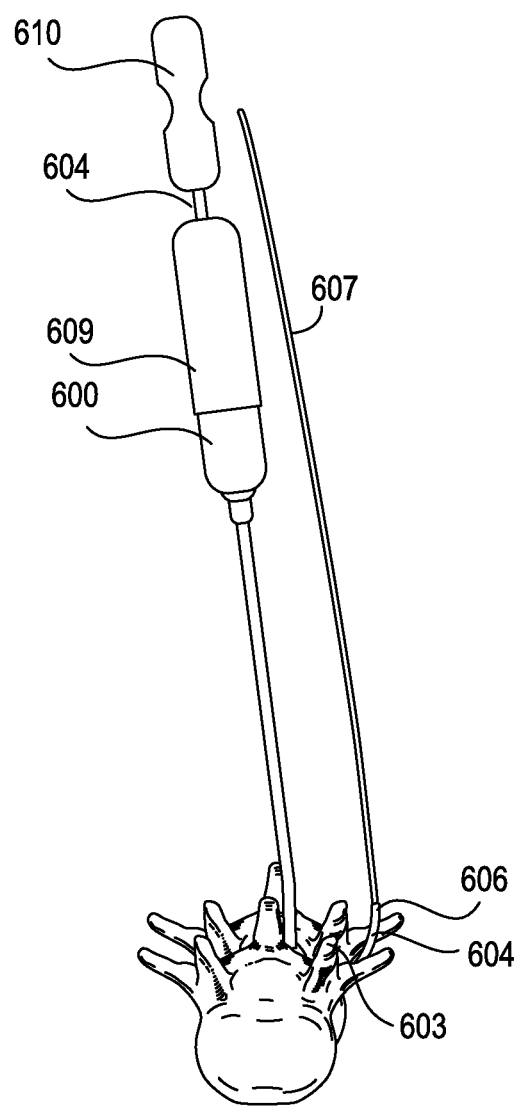
FIGS. 8A-8C demonstrate an alternative path of a probe, guidewire, and tissue modification device through a spinal region.
Figure 8B:
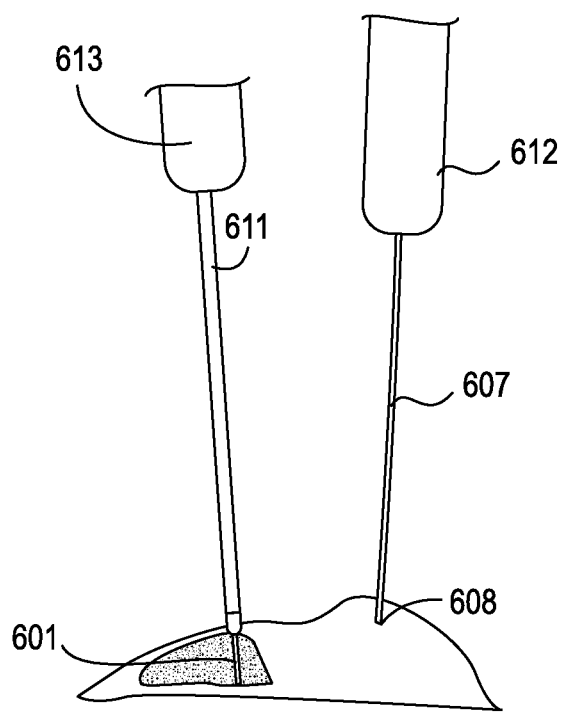
Figure 8C:
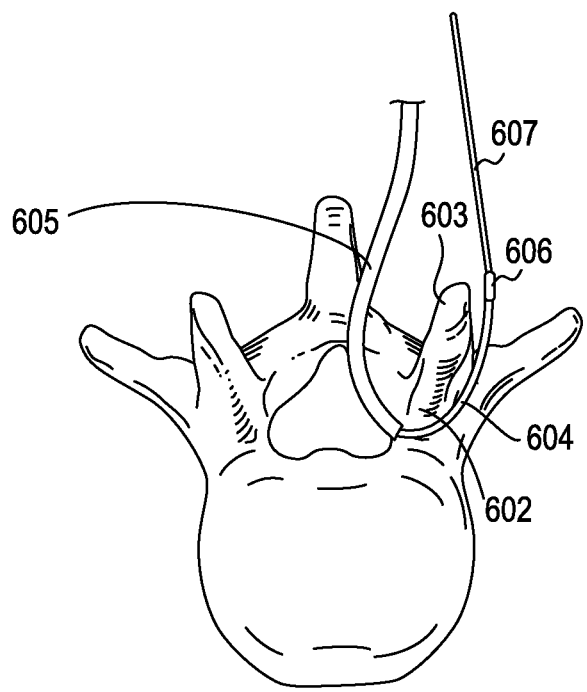

As shown in FIGS. 6A and 6B the probe 400 may be configured and/or used such that the guidewire is positioned to avoid the tissue (including vascular anatomy) on lateral side of the SAP. As shown, the probe 400 may be passed from outside of a patient's body at a first location 401 and through a spinal neural foramen 402 between a spinal nerve root or ganglia and a facet joint complex 403. As shown in FIG. 6B, the probe is configured such that inner cannula 404 may be advanced through outer cannula 405. The inner cannula advances out of the outer cannula to a position such that the tip 406 of the inner cannula points away from the lateral aspect of the SAP of the joint complex 403. In some embodiments, as described in more detail below, the inner cannula may include a plunger (610 in FIG. SA) coupled to the inner cannula that is configured to advance the inner cannula through the outer cannula. The outer cannula may include a handle 409 coupled to the outer cannula used to grasp and position the probe. The plunger and the handle may be configured such that the inner cannula may only be advanced within the outer cannula to a point where the plunger hits the handle and cannot be further advanced. In some embodiments, the plunger and the handle may be configured such that the inner cannula may only be advanced to a position such that the tip 406 of the inner cannula points away from the lateral aspect of the SAP of the joint complex 403. Alternatively, the inner cannula may be configured such that it may advance further to a position where it may wrap around the lateral aspect of the SAP, as shown in FIGS. 8A-8C. In this configuration, the plunger may include marking such that a user may only advance the plunger and the inner cannula to the desired position. As shown in FIG. 6A, the plunger 410 has been advanced such that there is an gap X between the plunger and the handle 409. The gap may be any suitable distance such that the tip 406 of the inner cannula points away from the lateral aspect of the SAP of the joint complex 403.

Figure 7:
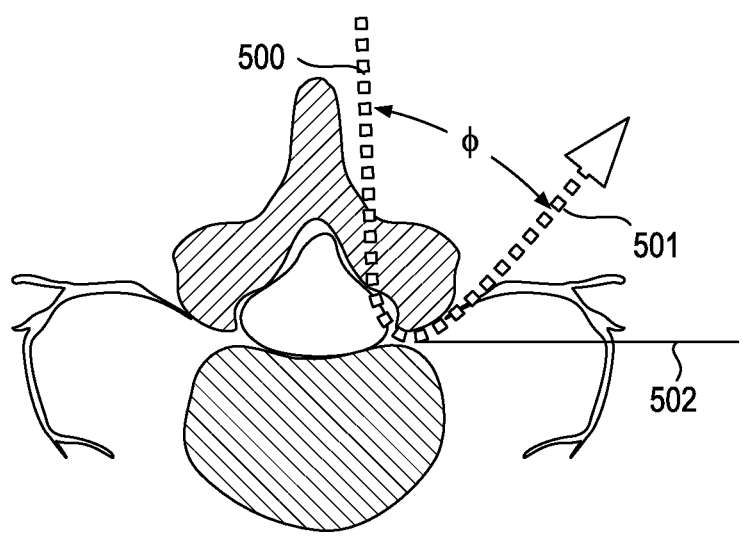

In some variations, as shown in FIGS. 6A and 6B, once the probe is deployed and optional neural localization is complete, a guidewire 407 is passed via the cannulated guide or probe. The guidewire can be sharp on its distal end and penetrate the skin dorsolaterally after exiting the foramen. As shown, the guidewire 407 may be passed through the inner cannula 404 from outside of a patient's body at a first location 401, through a spinal neural foramen 402 between a spinal nerve root or ganglia and a facet joint complex 403 where the guidewire exits the inner cannula and is advanced out of the patient's body at a second location 408. As shown, the guidewire is passed a distance from the lateral side of the facet joint complex 403 such that the entering portion of the guidewire through the probe 400 is not parallel to the exiting portion of the guidewire 407. As shown in FIGS. 6A and 7, there is an angle Φ between the entering portion 500 and the exiting portion 501. The angle may be any suitable angle greater than 0 degrees such that the guidewire avoids the tissue (including vascular anatomy) on lateral side of the SAP. At 0 degrees, the entering portion and the exiting portion are parallel to one another as shown in FIG. 8B. In some embodiments, the angle may range from about 10 to 60 degrees. For example, the angle may be about 30 degrees, or the angle may be about 45 degrees. As shown in FIG. 7, in most cases, the exiting portion is less than 90 degrees from the entering portion 500 due to anatomical limitations such as the transverse process as shown by line 502.

Figure 6C:
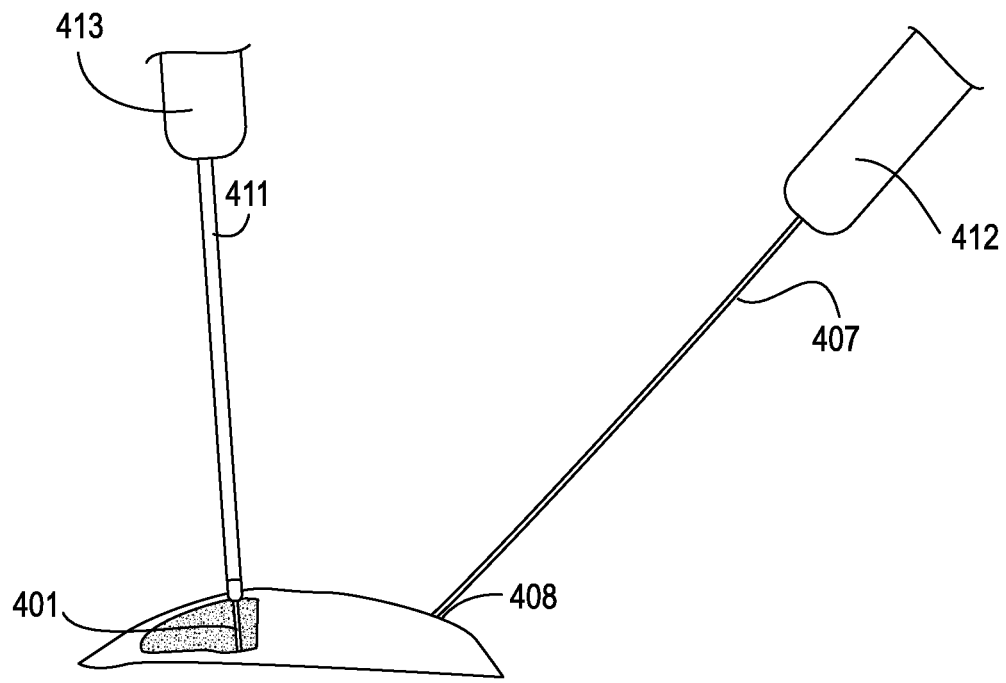

In some embodiments, the probe/guide is removed once the guidewire has been positioned. The guidewire may include a wire exchange tip on its proximal end. As shown in FIG. 6C, a flexible tissue modification device 411 (as described in more detail below) is attached to the proximal wire exchange tip, and a distal handle 412 may be secured to guidewire 407 at the distal end portion of the wire. The device can then be introduced into the epidural space and then into the lateral recess by careful upward force applied to the distal handle 412. As shown in FIG. 6C, the tissue modification device 411 is pulled by the guidewire 407 along the path established by the guidewire as described above. In some embodiments, the device is pulled by the guidewire on the path through the spinal anatomy. As described above in reference to FIGS. 2 and 3, suitable paths include paths shown by arrows 1812 and 1814 and/or 1816 and 1818 to decompress the nerve root origin at disc level and/or along the nerve root, respectively.

As shown in FIGS. 8A to 8C for comparison to the embodiment of FIGS. 6A to 7, the probe 600 may be configured and/or used such that the guidewire is positioned to wrap around the tissue (including vascular anatomy) on lateral side of the SAP. As shown, the probe 600 may be passed from outside of a patient's body at a first location and through a spinal neural foramen between a spinal nerve root or ganglia and a facet joint complex 603. As shown, the probe is configured such that inner cannula 604 may be advanced through outer cannula 605. The inner cannula advances out of the outer cannula to a position such that the tip 606 of the inner cannula wraps up and around the lateral aspect of the SAP of the joint complex 603. In some variations, as shown in FIGS. 8A to 8C, once the probe is deployed and optional neural localization is complete, a guidewire 607 is passed via the cannulated guide or probe. The guidewire can be sharp on its distal end and penetrate the skin dorsolaterally after exiting the foramen. As shown in FIG. 8C, the guidewire 607 may be passed through the inner cannula 604 from outside of a patient's body at a first location 601, through a spinal neural foramen 602 between a spinal nerve root or ganglia and a facet joint complex 603 where the guidewire exits the inner cannula and is advanced out of the patient's body at a second location 608 (FIG. 8B). As shown, the guidewire is substantially along the lateral side of the facet joint complex 603 such that the entering portion of the guidewire through the probe 600 is about parallel to the exiting portion of the guidewire 607.

In some embodiments, the probe/guide is removed once the guidewire has been positioned. The guidewire may include a wire exchange tip on its proximal end. As shown in FIG. 8B, a flexible tissue modification device 611 (as described in more detail below) is attached to the proximal wire exchange tip, and a distal handle 612 may be secured to guidewire 607 at the distal end portion of the wire. The device can then be introduced into the epidural space and then into the lateral recess by careful upward force applied to the distal handle 612. The tissue modification device 611 is pulled by the guidewire 607 along the path established by the guidewire as described above.

Figure 9A:
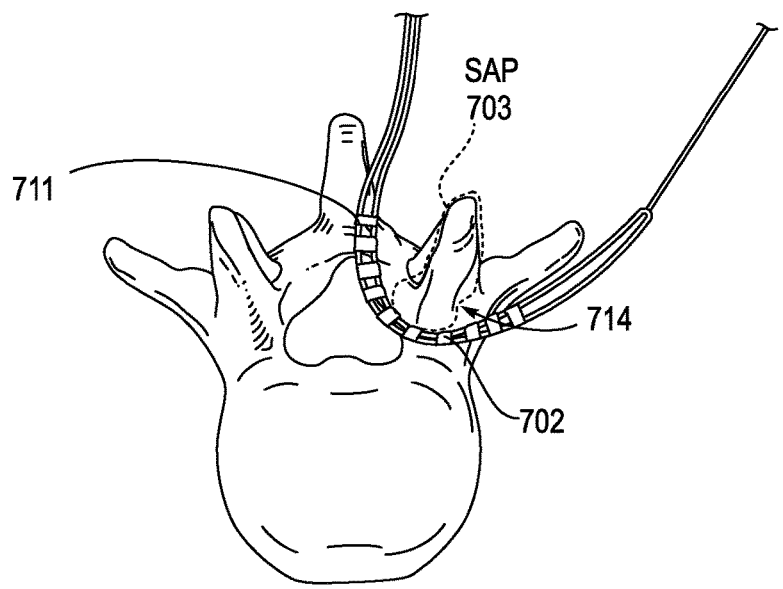
FIGS. 9A and 9B illustrate a space between the tissue modification device and portion of the spinal region.

As shown in FIG. 9A, the tissue modification device 711 is pulled by the guidewire along the path established by the guidewire as described above in reference to FIGS. 6A to 7. The tissue modification device 711 may be pulled from outside of a patient's body at a first location 401 (FIG. 6C), through a spinal neural foramen 702 between a spinal nerve root or ganglia and a facet joint complex 703. As shown in FIG. 9A, the tissue modification device 711 is pulled a distance from the lateral side of the facet joint complex 703 such that there is a space 714 between the tissue modification device and the lateral aspect of the SAP.

Figure 9B:
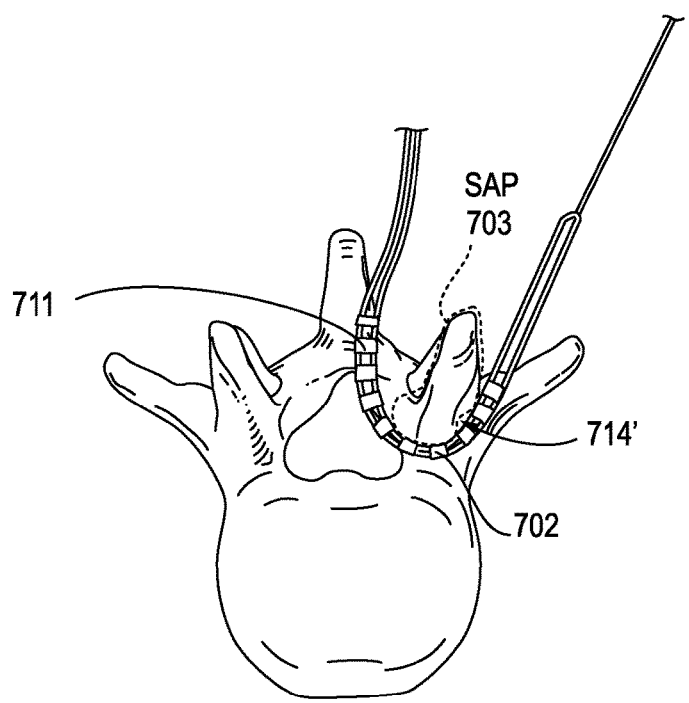

As shown in FIG. 9B, the tissue modification device 711 is pulled by the guidewire along the path established by the guidewire as described above in reference to FIGS. 8A to 8C. The tissue modification device 711 may be pulled from outside of a patient's body at a first location 601 (FIG. 8B), through a spinal neural foramen 702 between a spinal nerve root or ganglia and a facet joint complex 703. As shown in FIG. 9B, the tissue modification device 711 is substantially along the lateral side of the facet joint complex 703 such that there a smaller space 714' (when compared to 714 of FIG. 9A) between the tissue modification device and the lateral aspect of the SAP.

FIGS. 9A and 9B illustrate the difference in the size of the space 714 and 714' between the tissue modification device and the lateral aspect of the SAP when, as shown in FIG. 6A, the probe and guidewire are inserted such that the tip 406 of the inner cannula points away from the lateral aspect of the SAP of the joint complex 403 (FIG. 9A) versus when, as shown in FIG. 8A, the tip 606 of the inner cannula points up and around the lateral aspect of the SAP of the joint complex 603, respectively. As shown, there is a larger space 714 in FIG. 9A.

Once the device is in place as confirmed visually or radiographically, bimanual reciprocating strokes may be utilized to decompress dorsal impinging bone or soft tissue at the nerve root origin. In some embodiments as shown in FIG. 6C, the proximal handle 413 of the tissue modification device and the distal handle 412 may be held a distance apart while moving the tissue modification device to remove tissue, such that the tissue modification device is positioned and moved to avoid the tissue (including vascular anatomy) on lateral side of the SAP. Conversely, as shown in FIG. 8B for example, the proximal handle 613 of the tissue modification device and the distal handle 612 may be held a closer together while moving the tissue modification device to remove tissue, such that the tissue modification device is positioned substantially along lateral side of the SAP.

Figure 10A:
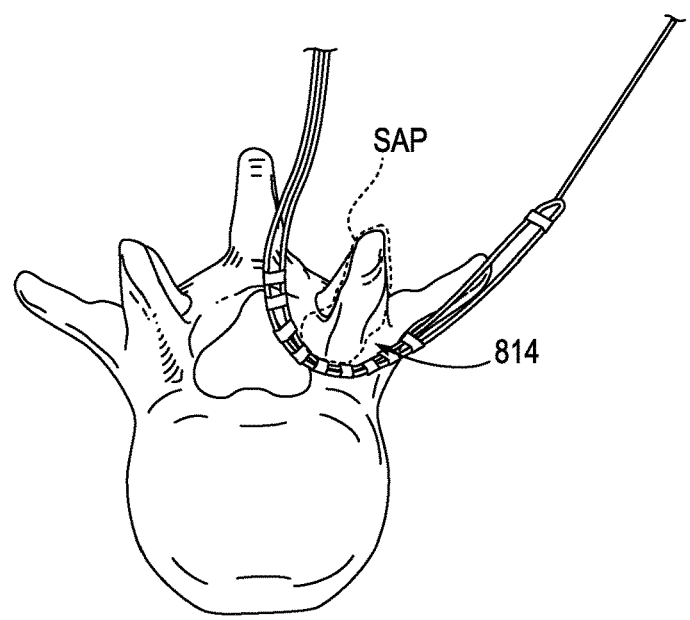
FIGS. 10A and 10B illustrate a space between the tissue modification device and portion of the spinal region.
Figure 10B:
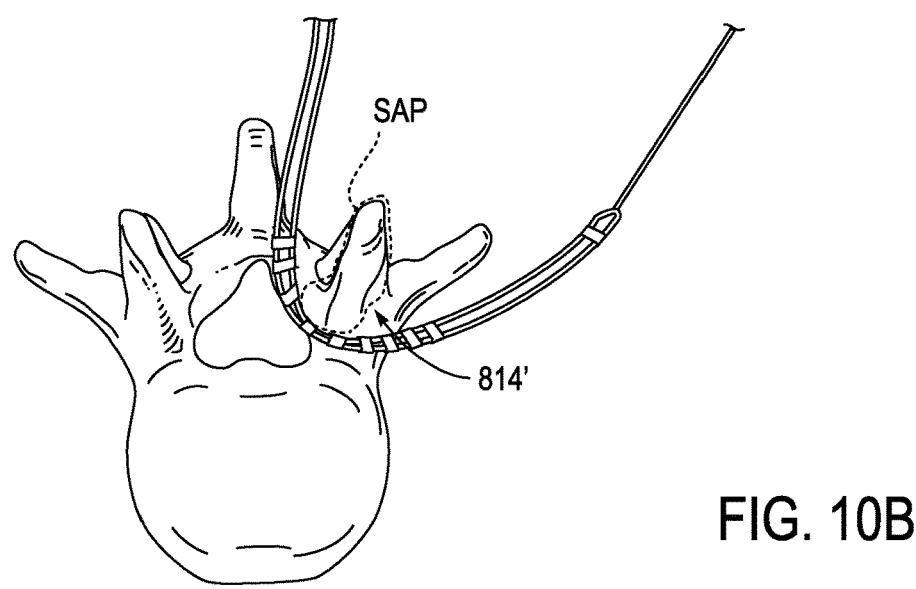

FIGS. 10A and 10B illustrate the difference in the size of the space 814 and 814' between the tissue modification device and the lateral aspect of the SAP. As shown in FIG. 10A, the proximal handle of the tissue modification device and the distal handle are held close together (as shown in FIG. 8B). As shown in FIG. 10B, the proximal handle of the tissue modification device and the distal handle are held a distance from one another (as shown in FIG. 6C). As shown, there is a larger space 814' in FIG. 10B.

Tissue Modification Device

Figure 11:
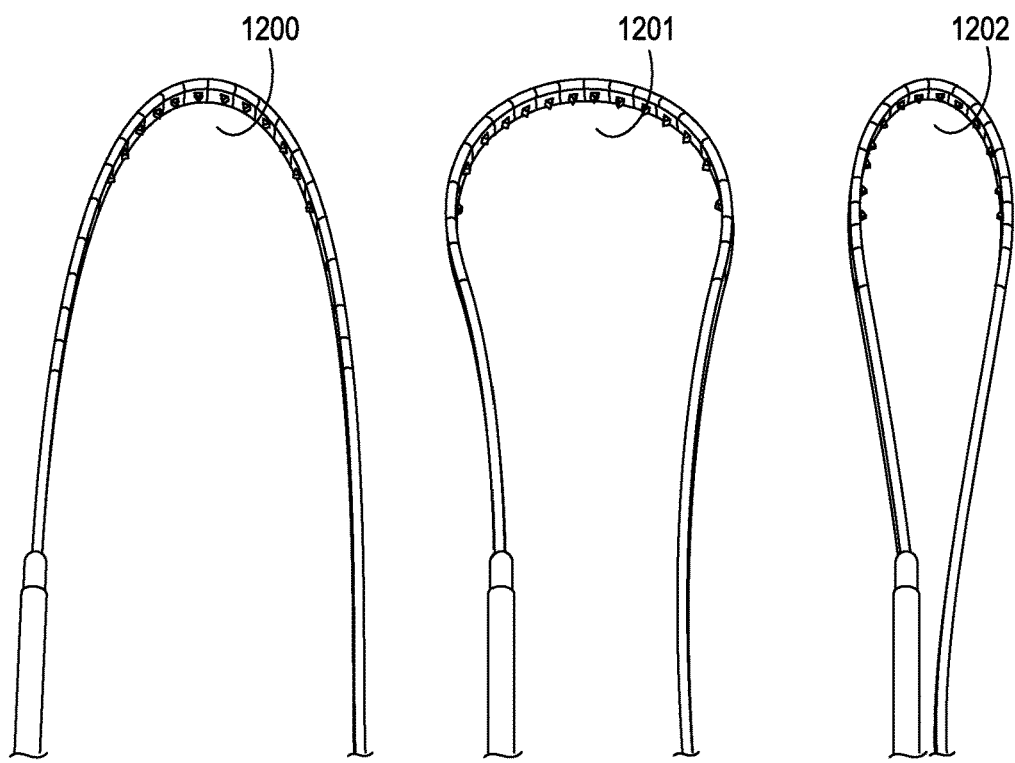

Described herein are systems including a tissue modification device. Various embodiments of tissue modification devices and systems, as well as methods for making and using tissue modification devices and systems, are provided herein. In general, a flexible tissue-modification device as described herein is configured to remove tissue from a patient. In particular, these tissue-modification devices may be configured to decompress spinal stenosis. The tissue modification device may be configured to have a variable stiffness along the length of the device. As shown in FIG. 11, the tissue modification regions 1200, 1201, and 1202 of the devices may have any suitable stiffness. As shown, tissue modification region 1200 that includes "dog bone" rungs, as described below, has a "semi-stiff" modification region. Tissue modification region 1201 includes a radius limiting strap coupled to the device such that the tissue modification region of the device is "stiff". Tissue modification region 1202 is more flexible than regions 1200 and 1201. A more stiff portion of the device will prevent the device from wrapping around the lateral side of the SAP and will therefore not remove tissue (including vascular anatomy) on lateral side of the SAP. In some embodiments, the more stiff portion of the tissue modification device is the tissue modification region. Alternatively, the more stiff portion may be any other suitable portion(s) of the device.

These devices typically include a flexible elongate body that extends proximally to distally (proximal/distal), and is configured to be inserted into a patient so that it extends around the target tissue, so that it can be bimanually pulled against the target tissue by applying tension to either end of the device. Thus, the device may be extended into, through, and/or around a spinal foramen.

The device is flexible in at least one plane and has a variable stiffness along the length of the device. For example, in variations in which the device has an elongated ribbon shape that is long and flat with a width greater than the thickness, the device includes a first major surface (e.g., a front) and a second major surface (a back), and has edges (minor surfaces) between the first and second major surfaces. The first major surface may be referred to as the anterior or front surface and the second major surface may be referred to as the posterior or back surface. The devices described herein may be flexible along the anterior and posterior surfaces, and the anterior or front surface may include one or more cutting edges configured to cut tissue as the anterior surface of the device is urged against a tissue. The posterior surface may be configured to shield or protect non-target tissue.

As mentioned, in operation, the device is urged against the target tissue and may be moved in the proximal/distal direction to modify (e.g., cut) the target tissue. For example, both the proximal and distal ends of the tissue-modification device may be pulled to urge the device against the target tissue, and may each be alternately pulled to a greater degree than the other handle to slide the device over the target tissue, allowing the cutting edges to cut and modify the target tissue.

Flexibly Connected Rungs

In some variations, a tissue modification device is formed from a plurality of flexibly connected rungs. As used herein, a rung may also be referred to as a link or crosspiece. A rung may be stiff (e.g., made of a relatively rigid material) or flexible. The rungs may be connected to or may form the anterior (front) major surface. At least some of these rungs include one or more cutting edges, which may be configured as blades. The cutting edges may be formed as part of the rung, or attached to the rung.

Individual rungs may have any appropriate shape. For example, a rung may have a rectangular shape, an oval shape, a trapezoidal shape, or the like. In general, the rung is relatively flat (e.g., having a thickness that is substantially less than the length and width). A rung may be smooth, rough or some combination. Different rungs in the same device may be different shapes and sizes, as illustrated below. A rung may be directly or indirectly connected to adjacent rungs.

Rungs are flexibly connected to adjacent rungs and/or to another portion of the tissue modification device. A connector, such as a cable, wire, chain, string, sheet, ribbon, mesh, fabric, or the like, may be used to connect adjacent rungs. The connector may be flexible, or stiff. A connector may extend only between adjacent rungs, or it may extend along all or a portion of the length of the device so that multiple rungs may be attached to the same connector. More than one connector may be used to connect adjacent rungs. For example, rungs may be connected between two parallel wires. In some variations, the rungs are directly connected to adjacent rungs by a hinge joint or the like. Combinations of connectors and direct connections between rungs may be used. In some variations, rungs may be separated from each other by a space. The space may be an opening. In some variations, one or more spacers are used to separate adjacent rungs. The spacing between adjacent rungs may be different.

Figure 12:
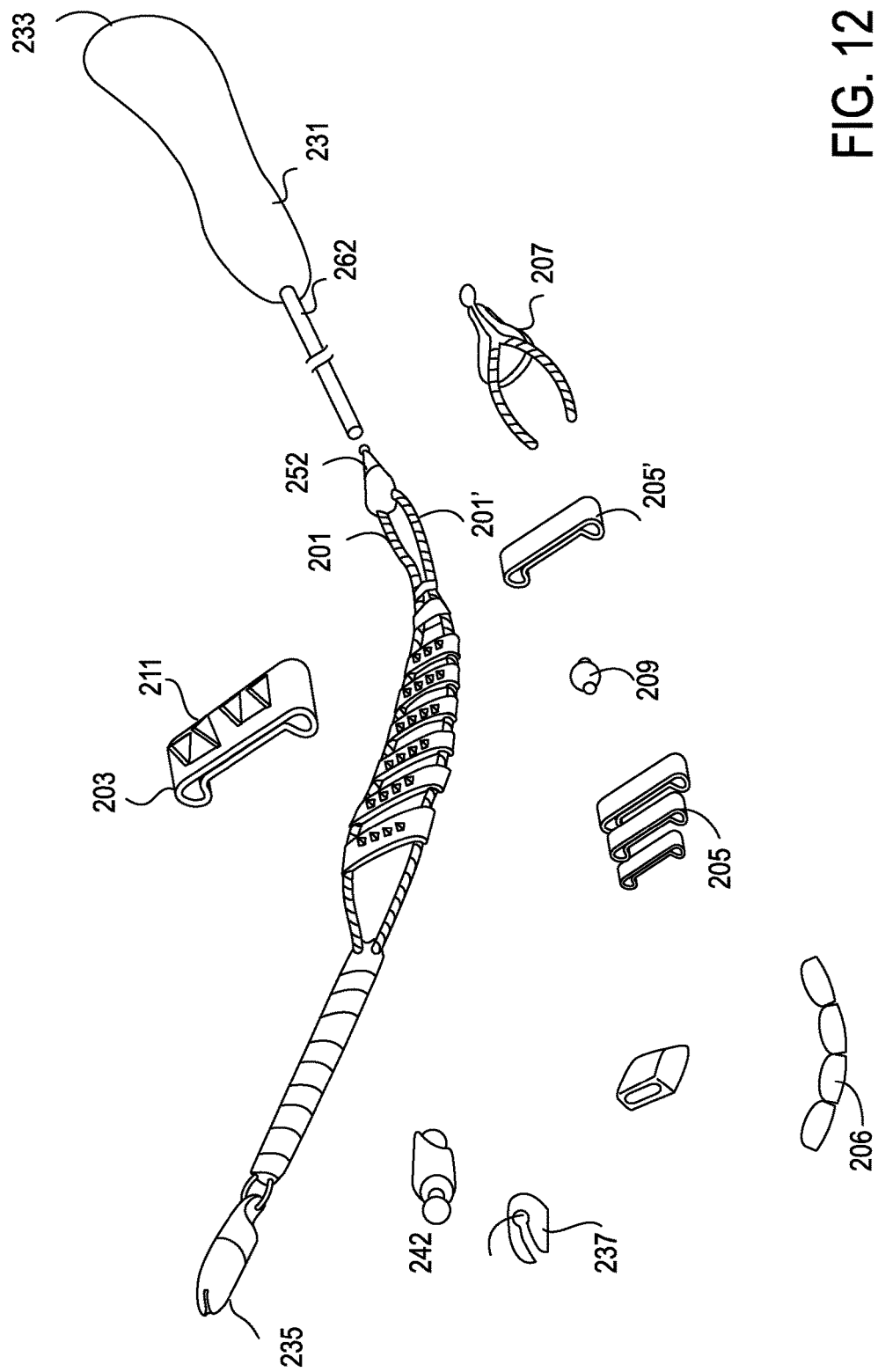

For example, FIG. 12 illustrates one variation of a tissue modification device having a plurality of rungs. FIG. 12 is a partially exploded, perspective view illustrating enlargements of various regions. The tissue-modification device shown in FIG. 12 is flexible and includes individual rungs that may articulate relative to each other. This device includes two parallel cables 201, 201' and a plurality of rungs 205, 205', 206, 203 extend between the cables. The cables are the connectors that link adjacent rungs. In this example, the two cables are joined at the proximal 233 and distal 235 regions. In some variations, the cable is joined at the proximal and distal ends, or is formed from a single cable; in some variations the two cables are separate. At least a portion of the cable is flexible. Any appropriate cable may be used, including metal or polymeric cables. Cables may be single-filament or formed of multiple filaments. The portion of the cable towards the distal end of the device, as shown in this example, may be hinged, and the links between distal and proximal sections may be connected in flexible junctions.

In some embodiments, the links or rungs 205, 205', 206, 203 spanning the cables have different shapes and sizes. The rungs 203 in the central region each include one or more cutting edges 211 projecting from the anterior (target tissue facing) surface. These cutting rungs 203 may form a tissue modifying region of the device. The cutting edges shown are triangular or pointed, although any appropriate shape may be used. Further, these cutting edges may be oriented in any desired manner; the orientation of the cutting edges may help steer or guide the device as it is urged against a target tissue to cut the tissue. In this example the cutting edges are oriented in parallel with the long axis (the distal/proximal axis) of the device.

Figure 13A:
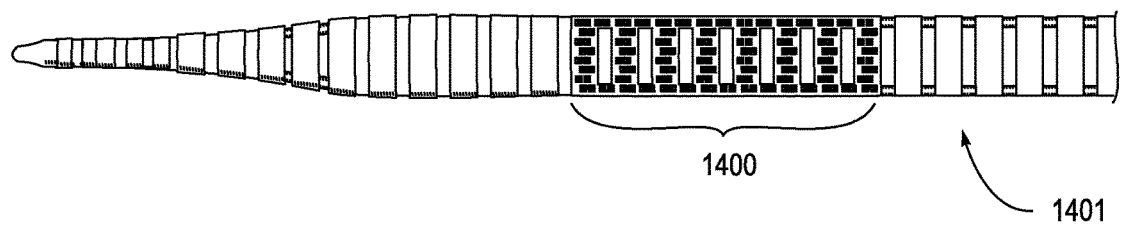
Figure 13B:
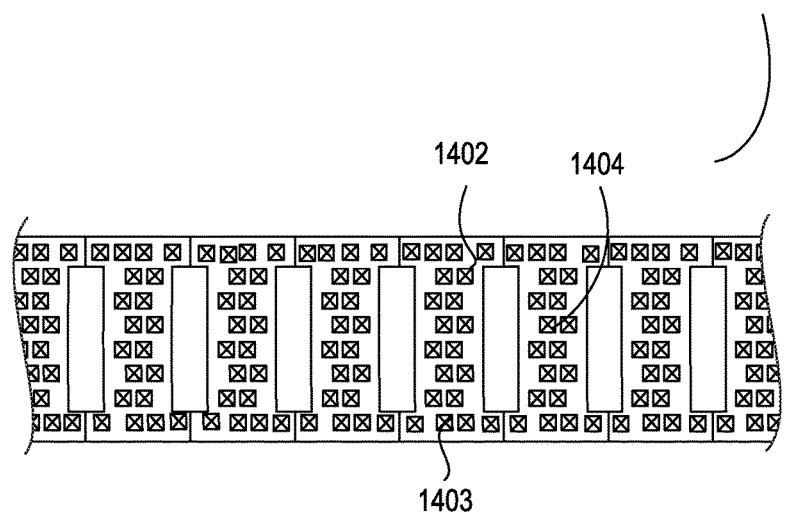

In some embodiments, the tissue modification device may be configured to have a variable stiffness along the length of the device. The variable stiffness may be achieved by one of several variations, or a combination thereof. In a first variation, the geometry of the rungs 211 that make up the tissue modification region has a different geometry than other rungs on the tissue modification device. In a first embodiment, as shown in FIG. 13A, the rungs that make up the tissue modification region 1400 of the tissue modification device 1401 are "dog bone" shaped rungs or "I" shaped rungs. As shown in FIG. 13B, a "dog bone" rung includes rung portions 1402 and 1403 that are coupled to the cables of the device. Rung portions 1402 and 1403 are wider than the center rung portion 1404 thereby creating a "dog bone" geometry. A series of rungs having a "dog bone" geometry is more stiff than a series of rungs having a standard rectangular geometry because the rung portions 1402 and 1403 are wider (or longer, with respect to the entire device) than the standard rectangular geometry. In general, the flexibility of a portion of the device is determined by the number of flex points within the portion. A flex point is a point along the device where two rungs (or a rung and a spacer) may flex and bend with respect to one another. For example, a portion of the device having a length of 1 inch with 10 flex points will be more flexible than a portion of the device having a length of 1 inch with 5 flex points. The wider the rungs are along the cable, the less flex points.

Figure 14A:
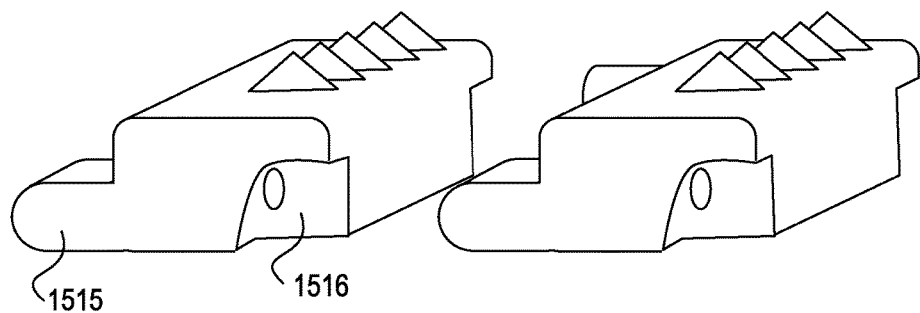
Figure 14B:
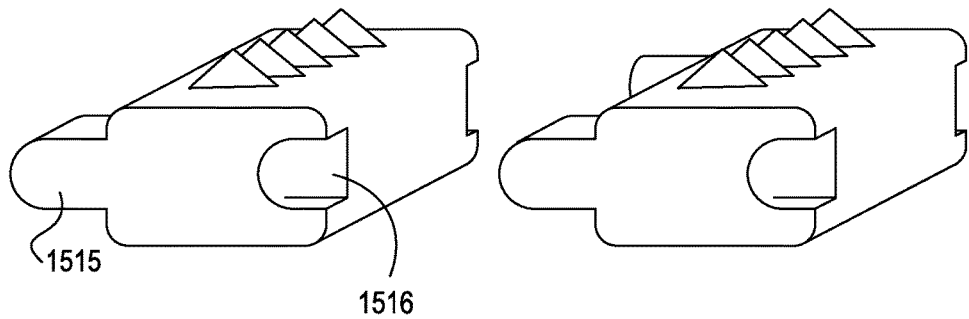

In some embodiments, the variable stiffness along the length of the device may be determined by an alternative rung geometry as shown in FIGS. 14A and 14B. As shown, the rung includes a male portion 1515 and a female portion 1516 adapted to receive the male portion. The height (or thickness) of the receiving portion (or the overall geometry of the shape of the receiving portion) vs. the overall height or shape of the rung is varied in order to dial in the desired stiffness on the cutting side of the system. In practice, the male and female portions will interact that the rungs are only able to bend a certain amount with respect to each other. As shown in FIG. 14A, the rungs may be fed onto a cable, or as in FIG. 14B, the rungs may snap together and not need to be fed onto a cable.

Alternatively, the variable stiffness along the length of the device may be determined by the flexibility of the cables. For example, the cables may be more stiff along the tissue modification region of the device and more flexible in other regions of the device. The stiffness of the cables may be determined by the material of the cables, the thickness or diameter of the cables, the number of cables used, etc.

The variation shown in FIGS. 15A and 15B, includes both rungs 2405 having a triangular (or other suitable shaped cutting edge) and rungs 2406 having tombstone shaped cutting edges. In some embodiments, as shown in FIG. 15B, the tombstone shaped cutting edges are located toward the outer side or edge of the rung, while the triangular shaped cutting edges may be located toward the center of the rung. For example, the tombstone cutting edges may be sized and configured to cut a flexible and/or soft tissue, including ligament, such as ligamentum flavum in a patient's spine; while the triangular shaped cutting edges may be sized and configured to cut a rigid tissue, including bone, such as the bone of a facet joint, the bone that defines a central canal, and/or the bone that defines a neural foramen of a spine of a patient, including a pedicle. The tombstone cutting edges positioned toward the outer edges of the rung, will cut a swath or strip of soft tissue. By positioning the cutting edge toward the outer edge of the rung, the cutting edge will cut an outline of the swath or strip into the soft tissue. In some embodiments, the device includes tombstone cutting edges toward the proximal end of the device while the device will not include cutting edges, specifically tombstone cutting edges, toward the distal end of the device. By having not cutting rungs toward the distal end of the device, this will prevent the distal end of the device from cutting on the lateral side of the SAP and will therefore not remove tissue (including vascular anatomy) on lateral side of the SAP.

Returning to FIG. 12, in some embodiments, cutting rungs 203 are separated by a gap formed by spacing elements 209 between the rungs. These spacing elements are also attached to the connector 201, 201' that flexibly connects the rungs. In FIG. 12 the spacers are threaded on the two parallel cables. The sizes of the connectors and/or spacing elements 209 may be varied to change the spacing between the rungs, and also the longitudinal shape (curvature) of the device, as described in greater detail, below. The sizes of the connectors and/or spacing elements 209 may also be varied indifferent regions along the length of the device to change the stiffness of the device in various regions.

The proximal end 233 of the device shown in FIG. 12 includes a handle 231 which may be permanently or removeably attached to the proximal end. The distal end 235 shown in FIG. 12 includes a guidewire coupler 237 that is flexibly attached to the distal end of the device. A guidewire coupler is configured to attach to a guidewire (e.g., one end of a guidewire) so that the device can be manipulated, at least in part, by pulling on the guidewire after the guidewire has been secured to the device. For example, in some variations a guidewire may be inserted into the body from a first location outside of the body, then passed around the target tissue (e.g., around a spinal foramen) and out of the body from a second position. The distal end of the guidewire may then be coupled to the flexible tissue modification device (such as the one shown in FIG. 12) and pulled through the body until the tissue modifying region of the device, e.g., the portion of the device including cutting rungs 203, is positioned opposite the target tissue. In some variations the guidewire used includes a tip region that is enlarged and may engage the guidewire coupler. For example, the guidewire may have a proximal end with a flange or ball. This enlarged region may be configured to fit into an opening on the guidewire coupler 242 so that the guidewire can be pulled distally from outside of the patient. In some variations the distal end of the device may be completely withdrawn, so that it can be grasped and manipulated. In other variations, the distal end of the tissue-modification device remains coupled to the guidewire, and the guidewire may be grasped to manipulate the distal end of the tissue-modification device. A handle may be attached to the guidewire.

As mentioned, in operation, the device is urged against the target tissue and may be moved in the proximal/distal direction to modify (e.g., cut) the target tissue. For example, both the proximal and distal ends of the tissue-modification device may be pulled to urge the device against the target tissue, and may each be alternately pulled to a greater degree than the other handle to slide the device over the target tissue, allowing the cutting edges to cut and modify the target tissue. In this example, as the blade(s) cut the tissue, a moment is generated between the tip of the blade and the base of the blade, on the rung, where the cable runs through the rung. Thus, in some variations, the base of the blade rung must be sufficiently wide to resist rotating about the length of the cable. Furthermore, it may be advantageous to include fixed rigid sections.

Radius Limiting Strap

Figure 16A:
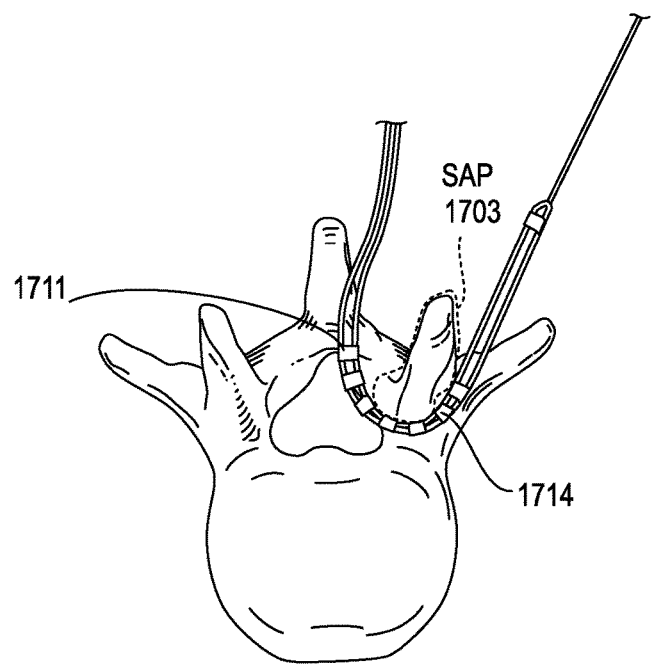
FIGS. 16A and 16B illustrate a space between the tissue modification device and portion of the spinal region.
Figure 16B:
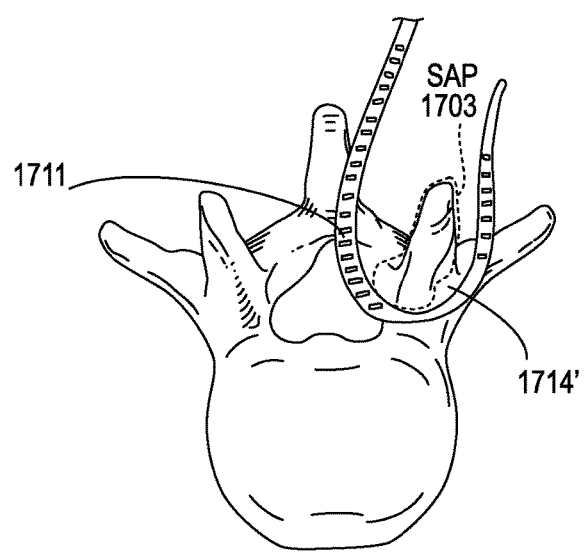

In some embodiments, the tissue modification device may be configured to have a variable stiffness along the length of the device. The variable stiffness may be achieved by one of several variations, or a combination thereof. In some embodiments, the tissue modification device may include a radius limiter. The radius limiter is configured to allow flexibility of elongate body while limiting the radius of curvature that the tissue modification region may achieve in at least one direction (e.g. concave or convex curvature). The radius limiter may be one of several variations. FIGS. 16A and 16B illustrate the difference in the size of the space 1714 and 1714' between the tissue modification device and the lateral aspect of the SAP. As shown in FIG. 16A, the tissue modification device does not include a radius limiting strap. As shown in FIG. 16B, the tissue modification device does include a radius limiting strap. As shown, there is a larger space 1714' in FIG. 16B.

Figure 17A:
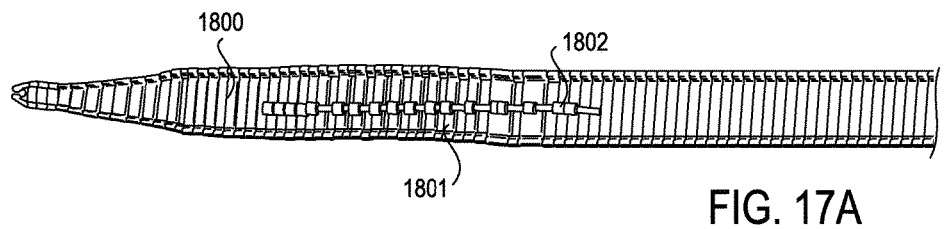
FIGS. 17A-19 show various configurations of radius limiting straps coupled to tissue modification devices.
Figure 17B:
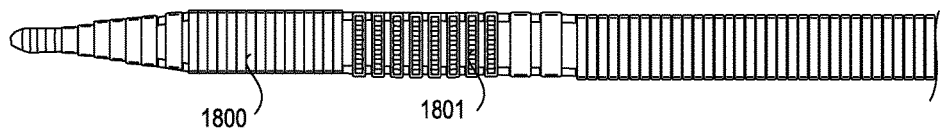

As shown in FIGS. 17A and 17B, the radius limiting strap 1801 is coupled to the elongate body of the tissue modification device 1800 by a plurality of connectors 1802 linking the radius limiting strap to the elongate body. FIG. 17A shows the back (posterior) side of the device. The radius limiting strap is coupled to the posterior side of the device such that it does not interfere with the cutting edges on the front (anterior) side of the device. In this variation, the radius limiting strap is a cable that is fed through the connectors. The connectors are coupled to the elongate body. Additionally, the radius limiter may be coupled to at least one of the connectors. In some embodiments, the radius limiter may be allowed to move with respect to the connectors and/or the elongate body. The radius limiter is positioned toward the center of the elongate body, but may alternatively be positioned in any other suitable position on the elongate body.

Figure 18A:
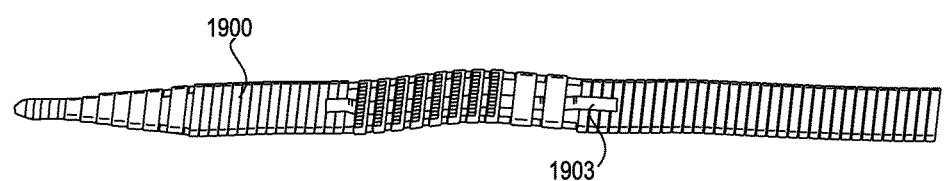
Figure 18B:
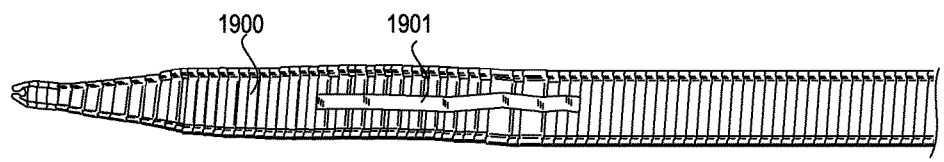

As shown in FIGS. 18A and 18B, the radius limiting strap 1901 is coupled to the elongate body of the tissue modification device 1900 at points 1903 and 1904. As shown in FIG. 18B, the strap 1901 is positioned on the posterior side of the device such that it does not interfere with the cutting edges on the front (anterior) side of the device. Connection points 1903 and 1904 are located on the front (anterior) side of the device, as shown in FIG. 18A, however they may be located on the back side or any combination thereof. In this variation, the radius limiting strap is a flat strap. The radius limiter may be coupled at at least one point along the length of the strap. In some embodiments, the radius limiter may be allowed to move with respect to the elongate body. The radius limiter is positioned toward the center of the elongate body, but may alternatively be positioned in any other suitable position on the elongate body.

Figure 19:
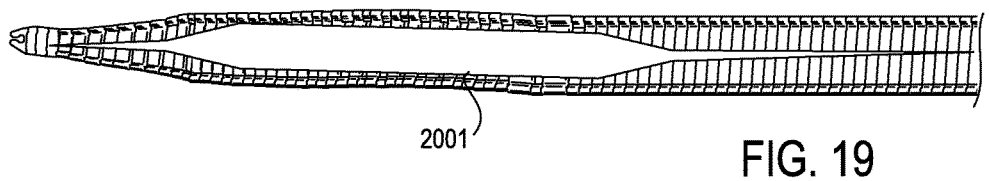

As shown in FIGS. 18A and 18B, the strap 1901 has a constant width and is located along the tissue modification region of the device. Alternatively, as shown in FIG. 19, the strap 2001 may have a varying width along its length and it may run along the device in regions in addition to the tissue modification region. For example, as shown in FIG. 19, the strap 2001 is thin toward the proximal and distal ends of the strap and is wider toward the center of the strap. The wider portion of the strap will limit the flexibility of the device more than the thin portion of the strap. In this example, the thick portion of the strap is behind the tissue modification region of the device and the thin portions of the device are behind the non tissue modifying regions of the device.

Avoid Soft Tissue

Figure 20A:
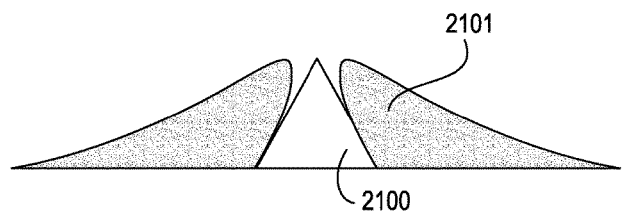
FIGS. 20A-25 show various configurations where the tissue modification device includes some variation of a flexible or compressible blade guard.
Figure 20B:
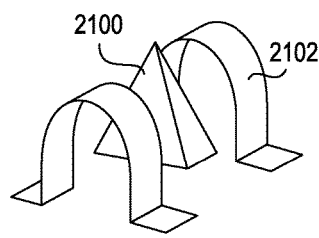
Figure 21:
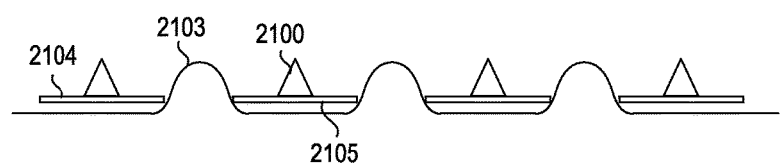

FIGS. 20A-25 show various configurations where the tissue modification device includes some variation of a flexible or compressible blade guard. In some embodiments, the tissue modification device may be configured to avoid cutting or damaging the soft tissue laterally from the facet joint and neural foramen (such as the foraminal vasculature and other healthy or non-target tissue). For example, the tissue modification device may be configured to be soft tissue sparing. In these examples, as the tissue modification device is moved against soft tissue, the blade guards will cover the blade. However, as the tissue modification device is moved against bone or a harder tissue (e.g. tissue, such as ligament, on top of bone), the blade guards will bend, flex, or compress, and allow the blade to enter into the target tissue to cut, or otherwise modify the target tissue. As shown in FIG. 20A, a blade 2100 may be surrounded by a flexible or compressible material 2101. For example, the material may be a foam, rubber, silicone, or other flexible or compressible material. As shown in FIG. 20B, the blade guards 2102 may include a plastic or metal spring adjacent to the blade 2100. As shown in FIG. 21 a substrate having flexible or rigid atraumatic ridges 2103 may be placed adjacent to the elongate body 2104. In some embodiments, the ridges may be placed between the rungs 2105 of the elongate body. In some embodiments, the ridges 2103 may be spring loaded so that they may be raised or lowered between the rungs of the device.

Figure 22:
Figure 23:
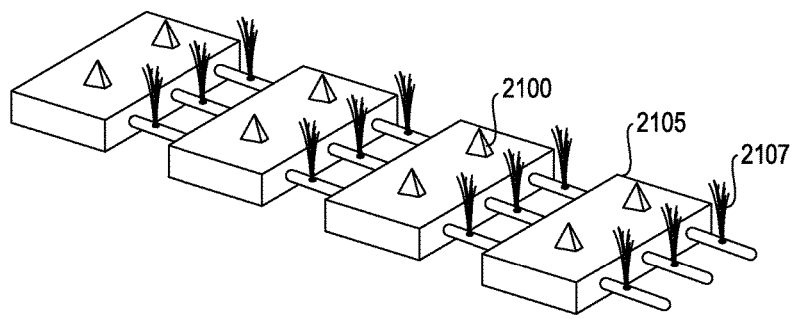
Figure 24:
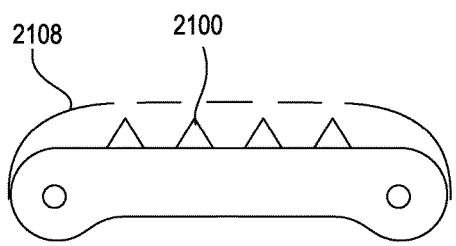

As shown in FIG. 22, the blade guards 2106 may include flexible bumps, such as silicone or other plastic, between each of the blades 2100. As shown in FIG. 23, the tissue modification device may further include brushes or bristles 2107 between the blades 2100 and/or rungs 2105 to push the soft, non-target tissue away from the blades. As shown in cross section in FIG. 24, the tissue modification device may further include a spring shield 2108 coupled along the length of the device. When the shield comes in contact with hard target tissue, it will flex down around the blades 2100, allowing the blades to cut into the target tissue.

Figure 25:
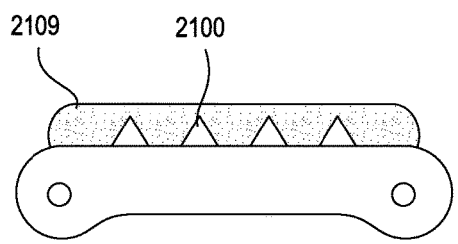

In some embodiments, as shown in FIG. 25, the tissue modification device may be coated in a layer of foam 2109 or other coating that will cover the blades 2100, yet compress or flex out of the way so that the blades can cut into the target tissue.

Figure 26:
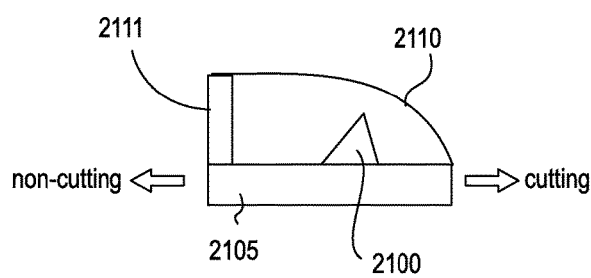

FIGS. 26-27 show various configurations where the tissue modification device cuts when it is reciprocated in a first direction and does not cut when it is reciprocated in the second direction. In some embodiments, the tissue modification device may be configured to avoid cutting or damaging the soft tissue laterally from the facet joint and neural foramen (such as the foraminal vasculature and other healthy or non-target tissue) by being configured to cut when the device is moved across the tissue in a first direction (medially, for example) and not cut when the device is moved across the tissue in a second direction (laterally toward the non-target tissue, for example). As shown in FIG. 26, the rungs 2105 may each have a flexible cover 2110 that can be moved over the blade 2100 to expose the blade in a first direction and a rigid back 2111 that holds the cover fixed when the device is moved in the opposite direction. As shown in FIG. 27, the substrate or elongate body 2104' may have a zig zag configuration with blades 2100 only positioned on the sides facing in a first direction. Therefore, the device can cut when the blades are moved in a first direction and cannot cut when the blades are moved in a second direction.

FIGS. 28-30B show various configurations wherein a substrate or shield bends to move the blades toward or away from the tissue. As shown in FIG. 28, the tissue modification device 2800 may include a shield 2801 that covers a portion of the device. For example, the shield may cover the distal blades 2802 such that the device cannot cut as far laterally beyond the facet joint and the neural foramen. The shield may be fixed at the distal end, and as the device is bent into a curved configuration around the facet joint, the shield may pop up to cover the blades.

As shown in FIGS. 29A and 29B, rather than having a curved shield, the blades 2900 may be coupled to a curved substrate 2901. For example, due to the curvature of the substrate, the blades toward the center of the device will perform the majority of the cutting, while the blades toward the proximal and distal ends of the device will not cut as much. The configuration in FIG. 29B is coupled to a wire 2902 at the distal end so that as the distal wire is pulled, the blades will be pulled further into a curved configuration. FIG. 30A and FIG. 30B illustrate an embodiment where the blades 3000 of the tissue modification device 3002 are coupled to a substrate 3001. In some portions of the substrate, the substrate may be configured to bend up (like a "tape measure") such that the blades can engage into the target tissue, while in other portions, the blades will be on a straight substrate and will be lower in the tissue modification device and will not cut, or will not cut as deeply.

Figure 31:
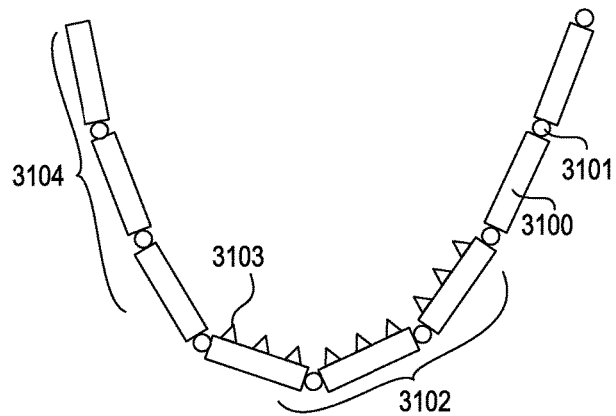
FIGS. 31-32 show various configurations wherein the rungs of the tissue modification device are movable.
Figure 32:
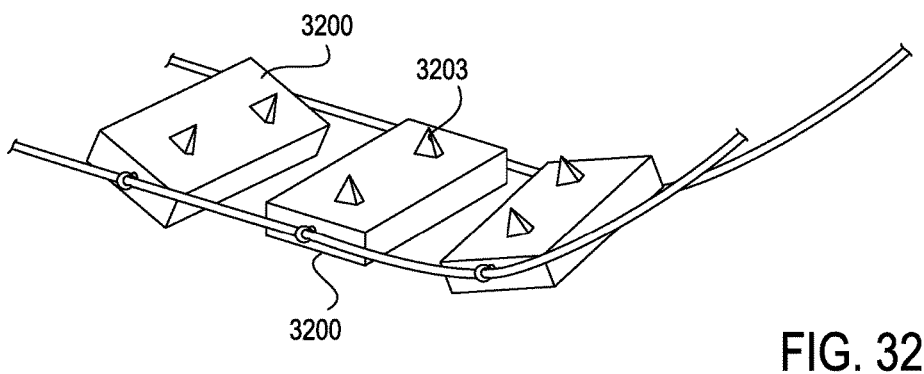

FIGS. 31-32 show various configurations wherein the rungs of the tissue modification device are movable. As shown in FIG. 31, the tissue modification device includes multiple blades sections or rungs 3100. Each section may be coupled to the adjacent section via a cam 3101. The cam may be configured such that it can bend or rotate the blade sections. For example the curved section 3102 as shown, the cam in this curved configuration may bend or rotate the sections such that the blades 3103 are facing up toward the target tissue. Alternatively, the cams may rotate or push the blades out of the substrate or shield (not shown). In the straight section 3104, the cams may rotate the bladed sections such that blades are not exposed to the tissue and will not cut or otherwise modify (or modify to a less degree) the non-target tissue located in these positions. As shown in FIG. 32, the blade sections 3200 are rotatable about a pivot joint 3200 such that in some configurations, the blades 3203 are rotated up, while in other configurations, the blades are 3203 are rotated down and away from the tissue. For example, the rungs toward the distal and proximal ends may be exposed, while the rungs at the center of the device may be rotated such that the blades are exposed and the blades may cut tissue.

Figure 33:
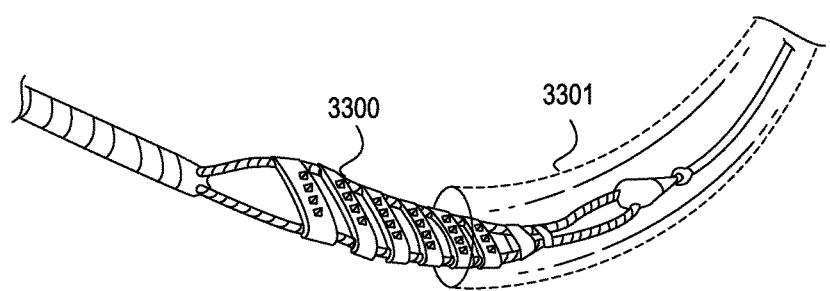
FIG. 33 shows a configuration wherein the tissue modification device includes a shield the covers the distal end of the device.

FIG. 33 shows a configuration wherein the tissue modification device 3300 includes a shield 3301 that covers the distal end of the device. In some embodiments, the shield may be fixed such that the tissue modification device may move into and out of the shield, while the shield covers the distal cutting blades as they moved through the lateral portion of the spine.

Figure 34:
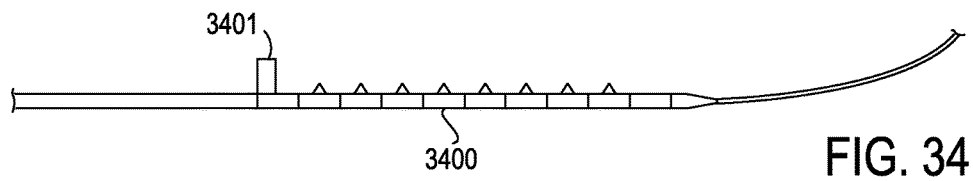
FIG. 34-36B show configurations wherein the travel of the tissue modification device within the body is limited in at least one direction.
Figure 35:
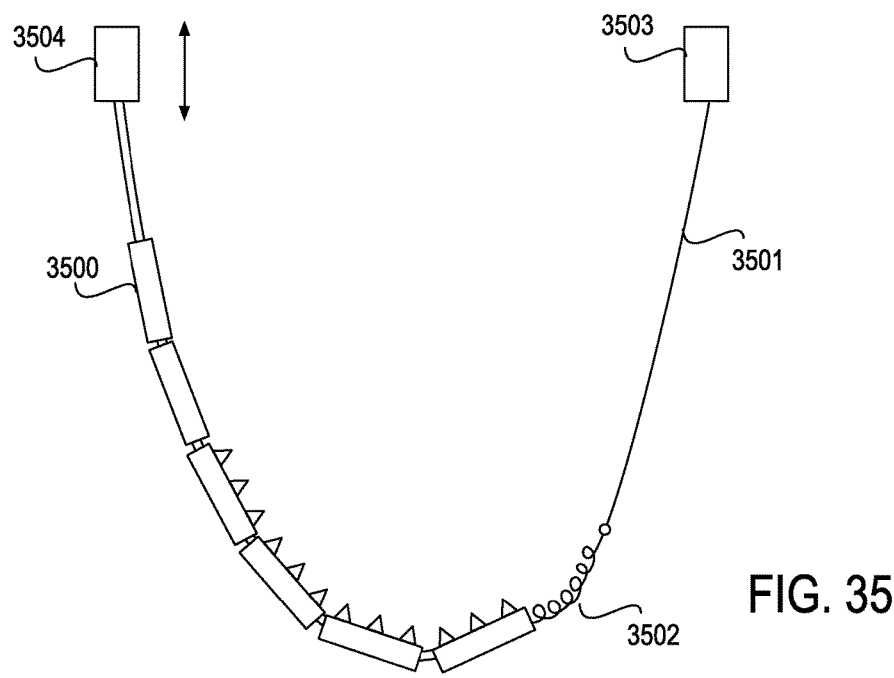

FIGS. 34-36B show configurations wherein the travel of the tissue modification device 3400 within the body of a patient is limited in at least one direction. As shown in FIG. 34, the tissue modification device 3400 includes a physical stop 3401 at the proximal end of the device. This stop will prevent the device from entering too far into, or beyond, the facet joint or neural foramen, such that it will not cut the healthy tissue lateral to the superior articular process of the spine. As shown in FIG. 35, the tissue modification device 3500 may be coupled to the guidewire 3501 via a spring 3502. In this configuration, the tissue modification device may be reciprocated in a unimanual fashion. For example, the distal handle 3503 may be held in place, while the proximal handle 3504 is pulled and then released. When the proximal handle is released the spring will return the tissue modification device to position. The length of the guidewire may determine the distance that the tissue modification device may be moved laterally through the spine. In some embodiments, the distal guidewire may be a rigid element, holding the distal portion of the tissue modification device (e.g. the distal end of the spring) in place.

Figure 36A:
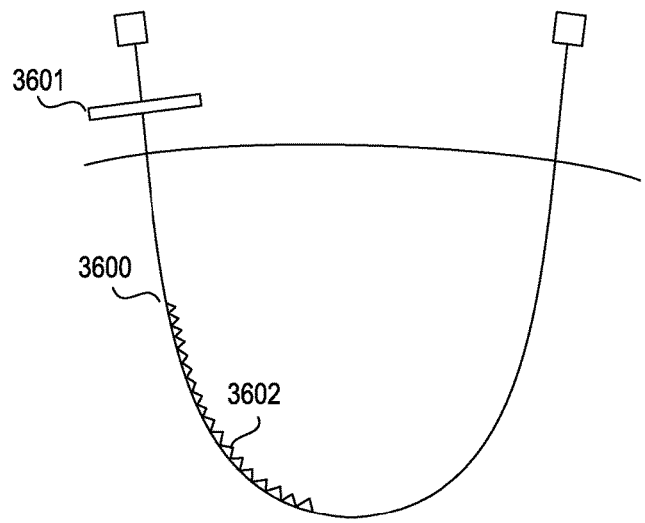
Figure 36B:
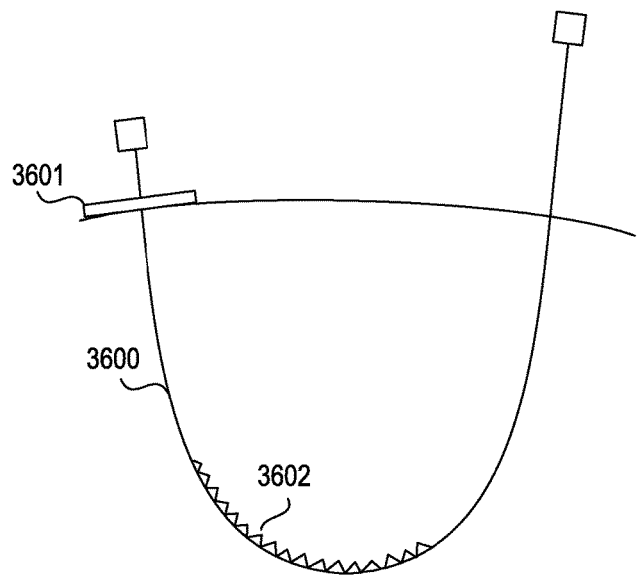

As shown in FIGS. 36A and B, the tissue modification device 3600 may include a physical stop 3601 outside of the patient that may prevent the blades 3602 device from being moved too far laterally (toward the right in the figure) in the spine. In some embodiments, the stop may be fixed to a frame within the operating room. For example, the stop may be coupled to a METRX frame. The stop may be adjustable along the proximal end of the device.

Delivery Devices

Described herein are systems including a delivery device. Various embodiments of delivery devices and systems are provided herein. In general, a delivery device as described herein is configured to deliver a hemostatic agent, tissue sealant analgesics, anti-inflammatories, or any other suitable agent to a desired surgical site. In particular, these delivery devices may be configured to deliver an agent to a surgical site for a spinal decompression procedure. The hemostatic agents may be delivered to an artery or other vessel that has been damaged or ruptured or is otherwise bleeding. The agent will promote hemostasis and stop or prevent unwanted and/or excessive bleeding.

In some embodiments, the agent(s) may be delivered to the surgical site via an agent deliver device. The delivery device may be any suitable device having any suitable configuration such that the agent may be delivered to the desired tissue and/or area within the surgical site. In some embodiments, the tissue modification device may be configured to deliver an agent to the surgical site. In alternative configurations, the delivery device may be a catheter that may be pulled into position within the surgical site via a guidewire. In further alternative configurations, a probe or cannula may be configured to deliver an agent to the surgical site.

Figure 37A:
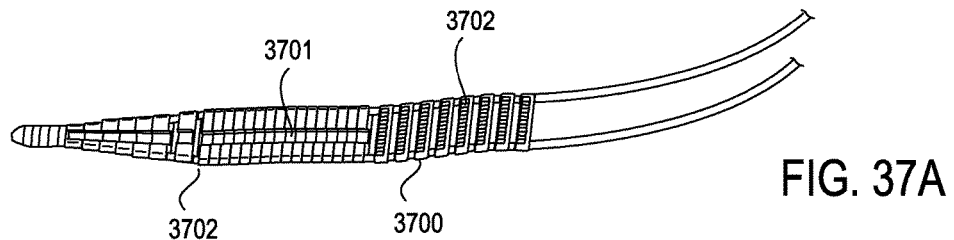
FIGS. 37A-38B show configurations wherein the tissue modification device includes a channel to direct an agent, such as a haemostatic agent.
Figure 37B:
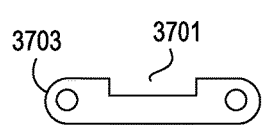
Figure 37C:
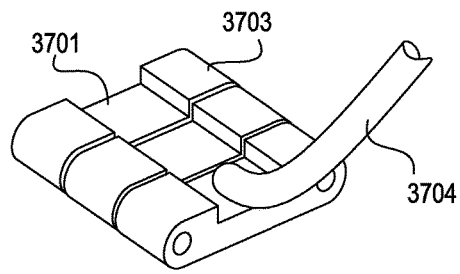
Figure 38A:
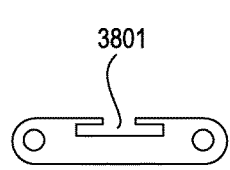
Figure 38B:
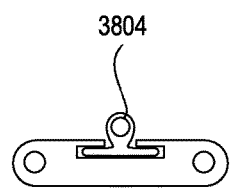

In some embodiments, the tissue modification device may be configured to receive and deliver an agent to tissue and/or a surgical site. For example the agent may be selected to stop or slow bleeding, such as a haemostatic agent. FIGS. 37A-38B show configurations wherein the tissue modification device 3700 includes a channel 3701 to direct an agent, such as a haemostatic agent toward a tissue or surgical site. As shown in FIG. 37A-B, the distal end 3702 of the tissue modification device may include a channel 3701. As shown in cross section FIG. 37B, the rungs 3703 toward the distal end portion of the device include a recess to form a channel 3701. Once the blades 3702 of the tissue modification device have been used to cut tissue (or during or before tissue modification), the device may be pulled proximally (i.e. at least partially out of the patient) such that a user may couple a catheter 3704 or syringe to the channel 3701 and deliver an agent to the channel, as shown in FIG. 37C. The tissue modification device may be used to directly deliver the agent to the desired location. For example, the agent may travel through the channel from the catheter to the desired location or the agent may be placed in the channel, and the device may be moved such that the channel is adjacent to the bleeding tissue. In some embodiments, a user may pull up on the distal and proximal ends of the tissue modification device to pull the device up against the target tissue and deliver the agent from the channel. As shown in FIGS. 38A and 38B, the channel 3801 may be configured to receive a shaped catheter 3804. The catheter may be placed into the channel either before, during, or after the device is used to modify tissue. The shaped catheter may then be used to deliver the agent to the desired location.

Figure 39:
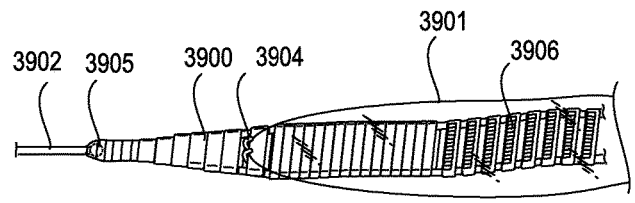
FIGS. 39-40B show configurations wherein a catheter or bladder may be coupled to a tissue modification device or to a guidewire directly.
Figure 40A:
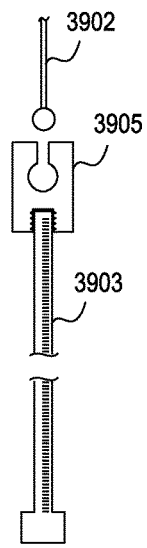
Figure 40B:
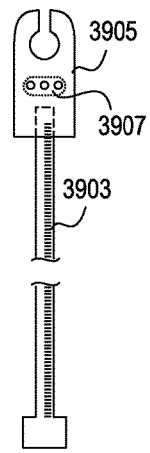

FIGS. 39-40B show configurations wherein a catheter 3903 (FIG. 40A) or bladder 3901 (FIG. 39) may be coupled to a tissue modification device 3900 or to a guidewire 3902 directly. As shown in FIG. 39, rather than the tissue modification device 3900 including a channel, a bladder 3901 or catheter (not shown) may be removably coupled to the tissue modification device. In some embodiments, the device 3900 may coupled to a guidewire 3902 via a guidewire coupler 3905 at the distal end of the device. The device may then be pulled distilling into position within a spine of the patient with the guidewire and may then be reciprocated to cut target tissue within the spine. The device may then be pulled back proximally, at least partially out of the spine of the patient. Then the bladder 3901 may be hooked on via hooks 3904, or otherwise coupled, to the tissue modification device 3900, and the guidewire 3902 may be used to pull the device and bladder distally into position. An agent may then be delivered through the bladder. In some embodiments, the bladder may be configured to function as a shield and cover the blades 3906 of the device, such that the blades cannot cut while an agent is being delivered from the bladder 3901.

In some embodiments, as shown in FIGS. 40A and 40B, after cutting as described above, the tissue modification device (not shown) may be pulled back proximally and removed from the spine and then removed from the guidewire 3902. A catheter 3903 with a guidewire coupler 3905 at its distal end may then be coupled to the guidewire. The guidewire may then be used to pull the catheter into position within the patient and the agent may be delivered. In some embodiments, the agent may be delivered via apertures 3907 in the guidewire coupler, the catheter, or any other suitable location.

Figure 41A:
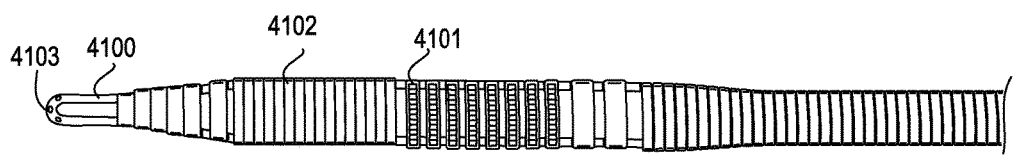
FIGS. 41A-41B show a configuration wherein the cable or tube connecting the rungs or the elongate body is configured to deliver an agent, such as a haemostatic agent.
Figure 41B:
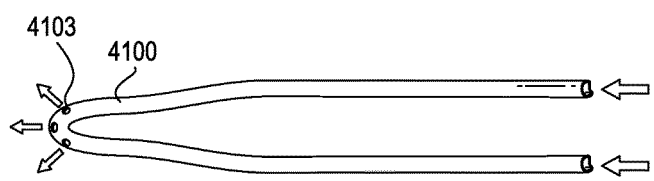

FIGS. 41A-41B show a configuration wherein the cable or tube 4100 connecting the rungs 4101 of the elongate body 4102 is configured to deliver an agent, such as a haemostatic agent. As described above the tissue modification device may be a flexible runged device. As shown, the rungs may be connected via a cable 4100. As shown in FIGS. 41A and 41B, the cable may be a hollow tube configured to receive and deliver an agent. As shown, the tip geometry of the tissue modification device may be modified such that the agent may be delivered from the tube through apertures 4103 in the device and into the desired location within the patient.

Figure 42A:
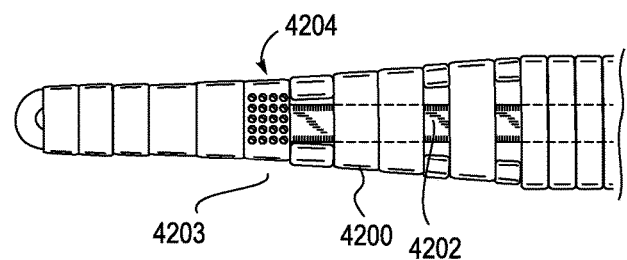
FIGS. 42A-44B show configurations wherein the tissue modification device further comprises a bladder or other device to deliver an agent, such as a haemostatic agent.
Figure 42B:
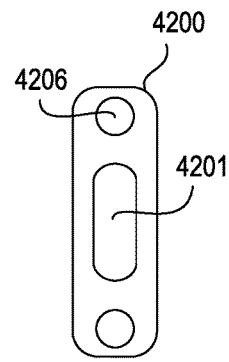
Figure 42C:
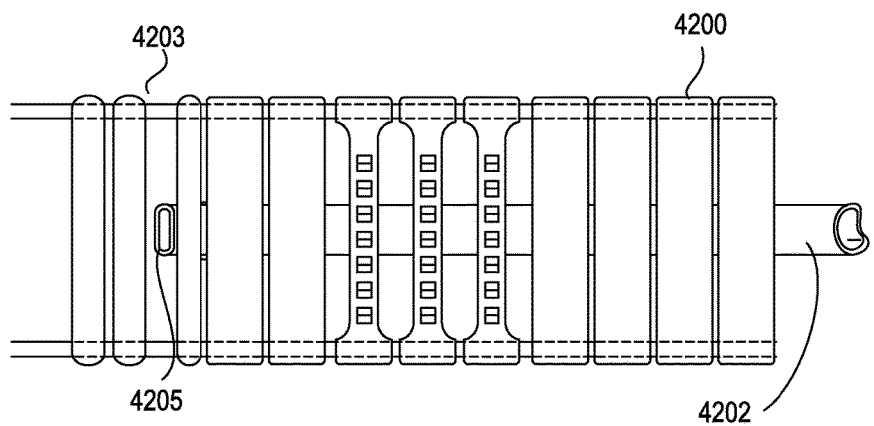

FIGS. 42A-44B show configurations wherein the tissue modification device further comprises a bladder, disposed along the length of the device, or other device to deliver an agent, such as a haemostatic agent. As shown in FIG. 42A and in an end view in FIG. 42B, the rungs 4200 may be modified such that they have a hole 4201 through their width to receive a tube or bladder 4202. As shown, the rung 4200 may also include a hole 4206 to receive a cable. As described above, the cable may be configured to connect the multiple rungs of the device. A tube or bladder 4202 may be disposed along the length of the device such that it exits the distal end 4203 of the device as shown in FIGS. 42A-42C. The device may include multiple holes 4204 or simply an opening 4205 for the distal open end of the tube, through which the agent may be delivered.

Figure 43A:
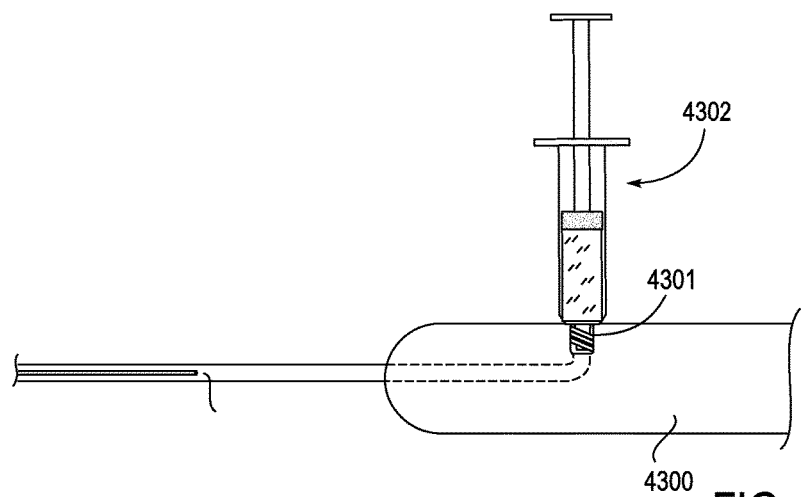
Figure 43B:
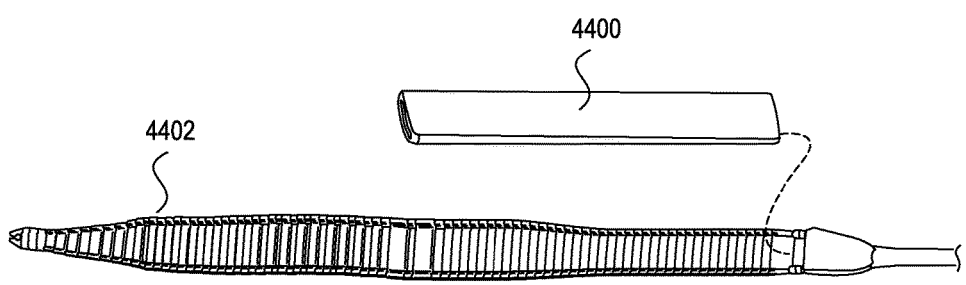
Figure 43C:
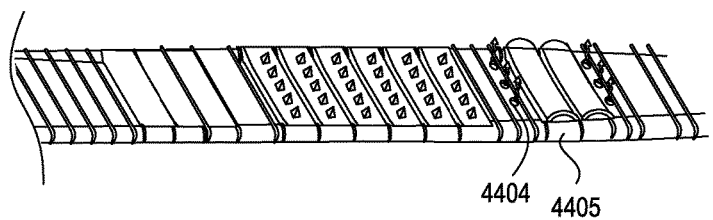
Figure 44A:
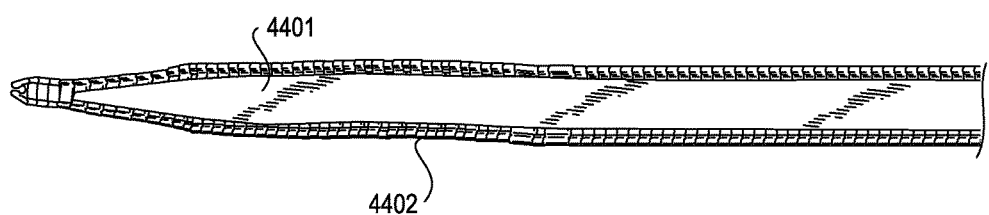
Figure 44B:
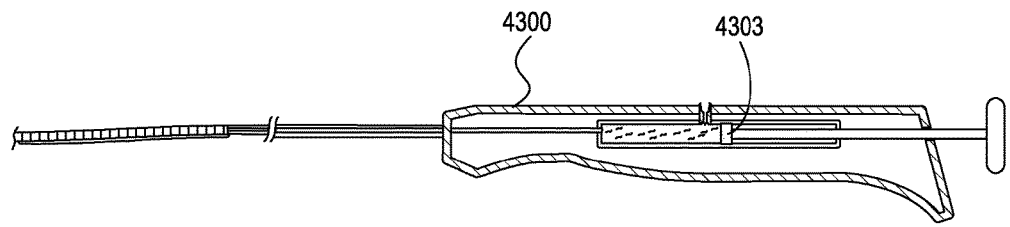

As shown in FIG. 43A, the bladder or tube may run proximally through the device to the proximal handle 4300 of the device. The proximal handle of the device may include a coupler 4301 configured to connect to a syringe 4302, as shown in FIG. 43A, or, as shown in FIG. 44B, the proximal handle 4300 may alternatively include a syringe or chamber 4303 within the proximal handle. As shown in FIGS. 43B and 44A, rather than running through the center of the device, the bladder (4400 and 4401 respectively) may be coupled to the back, non-abrasive, side of the tissue modification device 4402. As shown in FIG. 43C, the bladder 4400 of FIG. 43B may include apertures 4404 positioned between the rungs 4405 of the device. As shown, the agent will be delivered via the apertures 4404 between the rungs of the device to the target tissue or surgical site.

Figure 45A:
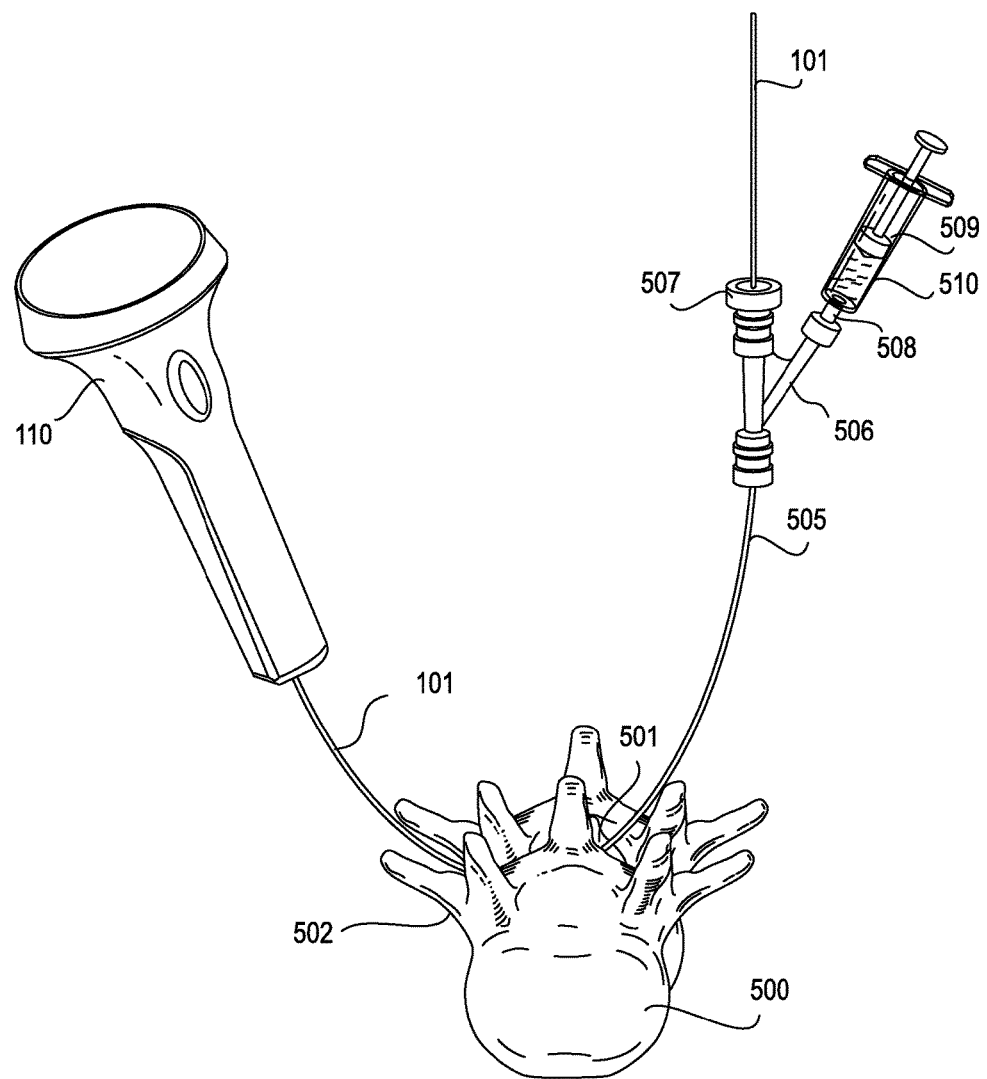
FIGS. 45A-49 illustrate various embodiments of delivery devices.

In alternative configurations, the delivery device may be a catheter that may be pulled into position within the surgical site via a guidewire. As shown in FIG. 45A, a guidewire 101 has been threaded along a path from an access location (such as through an interlaminar window 501) to where it exits through a foramen 502 of the spine 500. A distal guidewire handle 110 is coupled to the distal end of the guidewire. In this embodiment, the delivery device includes a catheter 505 and a connector 506. Catheter 505 preferably has a length such that the proximal end may be accessed outside of the patient and the distal end (not visible) is positioned within the surgical site adjacent to the necessary anatomical structures, such as blood vessels for example. In some embodiments, the catheter may be sized and configured to be fed through a METRX tube (Medtronic) or other minimally invasive surgical access device. The outer diameter of the catheter is about 1 mm to about 10 mm. In one specific embodiment, the catheter is a 14 gauge catheter.

As shown, the connector may be a Y-tube such as a "Tuey" valve. The connector includes a first branch 507 that is sized and configured to receive the guidewire 101. Branch 507 may include a locking mechanism such that the connector can lock down on the guidewire and prevent further motion of the guidewire through the connector. The lock may also prevent agent from escaping out of the connector through branch 507. The connector also includes a second branch 508 that is sized and configured to receive a syringe. The syringe preferably contains an agent 510, such as a hemostatic agent. Alternatively, the syringe may be coupled, over the guidewire, to branch 507 and an irrigation and/or suction source may be coupled to branch 508. In some embodiment, an additional two-way connector may be coupled to branch 508 such that the connector 506 becomes a three-way connector.

Figure 45B:
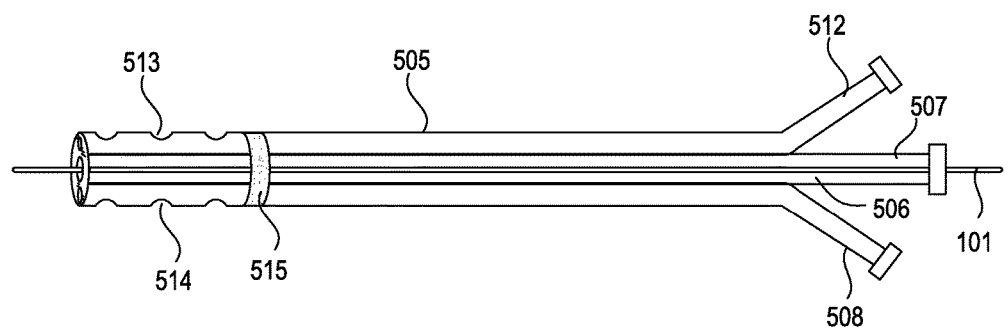

In an alternative variation, as shown in FIG. 45B, the delivery device also includes a catheter 505 and a connector 506, however as shown, the connector may include three branches 507, 508, and 512. The connector may be a three-way valve, for example. The connector includes a first branch 507 that is sized and configured to receive the guidewire 101. Branch 507 may include a locking mechanism such that the connector can lock down on the guidewire and prevent further motion of the guidewire through the connector. The lock may also prevent agent from escaping out of the connector through branch 507. The connector also includes a second branch 508 that is sized and configured to receive a syringe. The syringe preferably contains an agent 510, such as a hemostatic agent. Alternatively, the syringe may be coupled, over the guidewire, to branch 507. In some embodiments, branch 512 and 508 may be configured to provide suction and irrigation to the surgical site. For example, branch 512 may be configured to couple to a suction device. Apertures 513 are in fluid communication with branch 512 and the suction device. Apertures 513 may be positioned within the surgical site, and may be configured to remove fluids such as blood or flushing fluids, such as saline, from the surgical site. Branch 508 may be configured to couple to an irrigation device. Apertures 514 are in fluid communication with branch 508 and the irrigation device. Apertures 514 may be positioned within the surgical site, and may be configured to deliver fluids such irrigation or flushing fluids, such as saline, to the surgical site. These fluids may then be received by apertures 513 and removed as described above. As shown, catheter 505 includes three lumens. Any one of the branches and their respective lumens or apertures may be configured to couple to the guidewire 101, couple to an agent delivery syringe and deliver the agent to the surgical site, couple to a suction device and provide suction to the surgical site, and/or couple to an irrigation device and provide irrigation to the surgical site. The delivery device, as shown in FIG. 45B, may also include a marker 515. Marker 515 is positioned near the distal end of the catheter 505, and in some embodiments marks the position of apertures 513 and 514 and/or the distal end of the catheter. Marker 515 may be radiopaque such that it can be visualized fluoroscopically or by any other suitable visualization modality. The catheter may include a plurality of markers that may be positioned at any suitable location along the length of the delivery device. Alternatively, the entire delivery device, or a portion thereof, may be made of a radiopaque material, or a material treated to become radiopaque.

In use, the delivery device may be thread over the guidewire 101 at any point during a surgery—before tissue modification, during tissue modification, after tissue modification, and/or any combination thereof. The catheter 505 is thread over the guidewire such that the catheter is positioned into a desired position within the surgical site. As shown in FIG. 45A, the delivery device may be coupled to the proximal end of the guidewire and delivered to the surgical site by way of an interlaminar window. Alternatively, the delivery device may be coupled to the distal end of the guidewire (in addition to or instead of the distal handle 110). In this variation, the delivery device may be delivered to the surgical site by way of a spinal foramen. Once in the desired position, the locking mechanism of branch 507 may be clamped down on the guidewire. The catheter, in some embodiments, is made from a material that is stiff enough such that the catheter will not buckle or be pushed back along the guidewire by the spinal anatomy as the catheter is inserted into position. The catheter may include a hole at the distal end of the catheter through which the agent may be delivered. Alternatively (or additionally) the catheter may include holes or fenestrations along a portion of the length of the catheter. The catheter, in some variations, may be thin and flexible and ribbon shaped. For example, in variations in which the delivery device has an elongated ribbon shape that is long and flat with a width greater than the thickness, the device includes a first major surface (e.g., a front) and a second major surface (a back), and has edges (minor surfaces) between the first and second major surfaces. The first major surface may be referred to as the anterior or front surface and the second major surface may be referred to as the posterior or back surface. The anterior surface of the catheter may be positioned such that it faces toward the back of the patient, i.e. toward the facet joint, for example. The catheter may have holes for the agent along only the anterior surface, or may have holes on both the anterior surface and the posterior surface.

In an alternative variation (not shown), the syringe (coupled to a catheter, or independently) may be fed over the guidewire directly, rather than coupling to a connector. In this variation, the syringe may have a lumen disposed along the length of the catheter through which the guidewire may be fed. The guidewire may be used to guide the syringe (or other suitable agent receptacle) into the correct position within the surgical site. The syringe or delivery device may include a grommet or o-ring to seal the space between the guidewire and the syringe to prevent any leakage of the agent to be delivered.

In another alternative variation, similar to the variation of FIGS. 40A and 40B, the guidewire may be coupled to the end of the delivery device. The proximal shaped end of the guidewire may be coupled to the distal end of the catheter (or other portion of the delivery device) and may be used to pull the catheter into location. In this variation, the catheter may have a guidewire coupler at the distal end of the catheter and a hole or a plurality of holes on the catheter proximal to the guidewire coupler. In another alternative variation, the catheter or other portion of the delivery device may include a rapid exchange lumen. In this variation, the catheter includes a lumen that runs substantially along the length of the catheter, fluidically connecting ng an injection port (into which the agent is delivered, via a syringe for example) to the holes through which the agent is delivered to the surgical site. The catheter includes a second "rapid exchange" lumen that is sized and configured to receive the guidewire. This lumen does not run the length of the catheter but functions to couple the catheter to the guidewire.

Figure 46A:
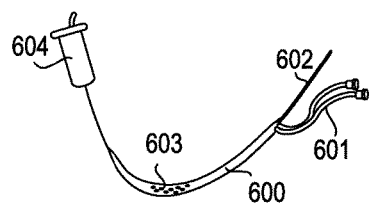
Figure 46B:
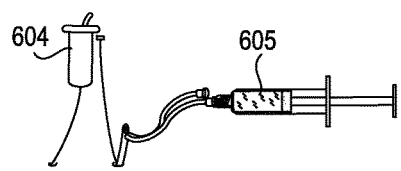

As shown in FIGS. 46A and 46B, the delivery device may include a ribbon 600 and at least one port 601 fluidically coupled to the ribbon. As shown, the ribbon 600 includes at least one lumen along the length of the ribbon through which the guidewire 602 may run. As described above, the ribbon 600 may be coupled to the guidewire by being fed over the guidewire (as shown) or may include a guidewire coupler at its distal end and be coupled to the guidewire in an end-to-end configuration. The port(s) 601 may be fluidically connected to the same lumen through which the guidewire runs, or may be connected to an additional lumen. That lumen is also fluidically connected to holes 603 in the ribbon through which the agent may flow to the desired surgical location. As shown in FIG. 46B, in use, the surgeon or other user may grasp the distal handle 604 (coupled to the distal end of the guidewire 602) and the proximal end of the guidewire (which may be coupled to a proximal handle or other device) in one hand, while delivering an agent through a syringe 605 into port 601 with a second hand. Alternatively, a second user may operate the syringe. As the agent is delivered through the delivery device the user may pull up (i.e. away from the patient) on the distal and proximal ends of the guidewire to position the ribbon directly against the tissue to be treated.

As described above, in this variation, in which the delivery device has an elongated ribbon shape, the device includes a first major surface (e.g., a front, shown) and a second major surface (a back, not shown). The first major surface may be referred to as the anterior or front surface and the second major surface may be referred to as the posterior or back surface. The anterior surface of the catheter may be positioned such that it faces toward the back of the patient, i.e. toward the facet joint, for example.

Figure 47:
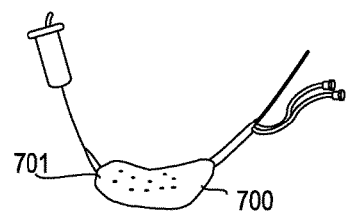

In some embodiments, as shown in FIG. 47, the delivery device, similar in most respects to the delivery devices described above, may also include a balloon 700. The balloon may be a low-pressure, high-volume balloon. The balloon may contain the agent and may function to deliver the agent through holes 701 upon inflation.

Figure 48:
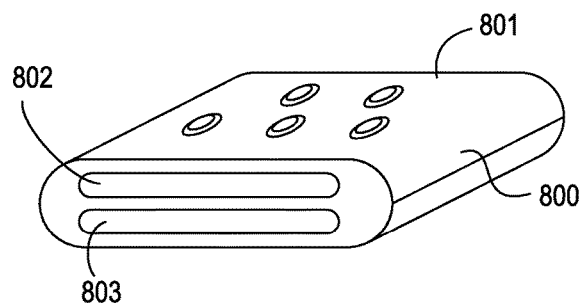

In some embodiments, as shown in FIG. 48, the delivery device may include a two sided applicator. In this embodiment, the applicator 800, as shown in cross section in FIG. 48, has an elongated ribbon shape having a first major surface (e.g., a front, shown as 801) and a second major surface (a back, not shown). The delivery device includes two lumens: a front lumen 802 and a back lumen 803 that fluidically couple front holes 804 and back holes (not shown) to a front injection port and a back injection port, respectively. The holes are located toward the middle or distal end of the delivery device and the injection ports are location at the proximal end of the delivery device which remains outside of the patient. When the delivery device is positioned within the surgical site, the anterior surface of the device may be positioned such that it faces toward the back of the patient, i.e. toward the facet joint, for example; and the posterior surface of the device may be positioned such that it faces toward the front of the patient, i.e. toward the nerves and other non-target tissue. Different agents with different functions may be injected into the different lumens and delivered to different anatomy having different requirements. For example, a hemostatic agent may be delivered to the surgical site and tissue removal area while an analgesic may be delivered to a nerve on the opposite side of the device. Other possible agents are listed in FIG. 48.

Figure 49:
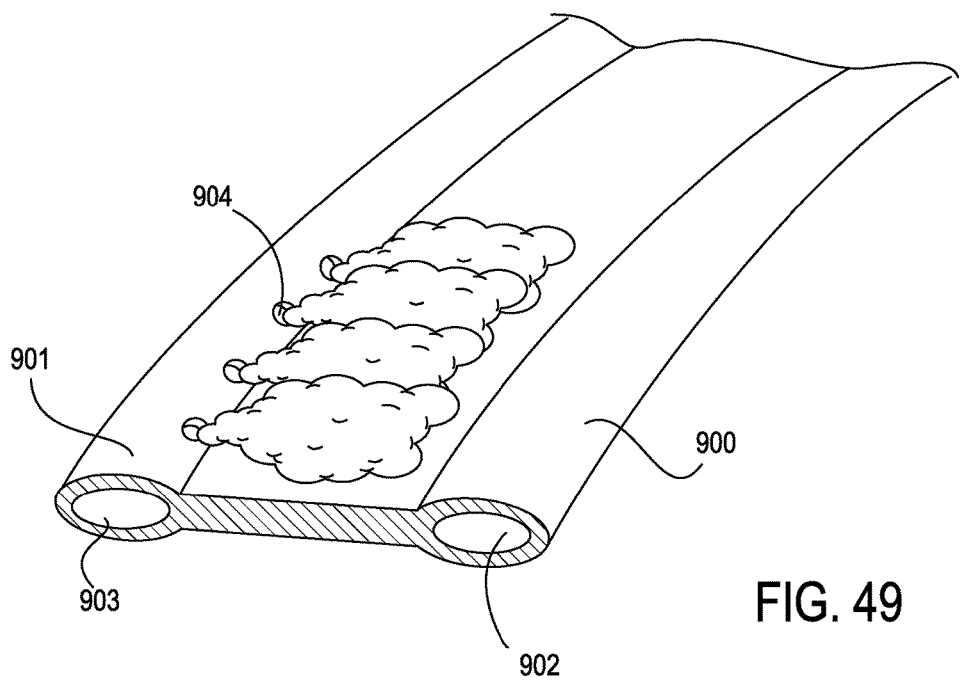

As shown in FIG. 49, a ribbon shaped delivery device may include larger edges 900, 901 along at least a portion of the length of the ribbon. The injected material seems more likely to remain at the target site, as shown in FIG. 49 as the edges may function to act as a barrier and keep the injected agent toward the center of the delivery device. In some embodiments, as shown the edges 900 and 901 may include lumens 902 and 903. The lumens may couple injection ports to the holes through which the agent is delivered. For example, lumen 903 is fluidically connected to holes 904. The holes connected to lumen 902 may be located on the top side of edge 900 or may be located on the opposite side of the device from holes 904.

In some alternative embodiments, a tissue modification device, as described above, or a neural localization device may further include agent injection ports and/or holes to deliver the agents. For example, the tissue modification device may deliver hemostatic agent or analgesics to the surgical site while the tissue modification device is also modifying and/or removing target tissue.

In some alternative embodiments, a delivery device, a tissue modification device, and or a neural localization device may be configured to deliver energy to the surgical site, such that the bleeding may be stopped or prevented with cautery rather than by delivering a chemical agent to the surgical site. For example, the device may be configured to deliver heat and/or electricity (such as a bipolar or monopolar signal) to the surgical site. For example, the bleeding could be stopped or prevented with electrocauterization and/or ligation, which is the process of destroying tissue to stop or prevent bleeding using heat conduction from a metal probe or electrode heated by electric current. Alternatively, the tissue could be ablated (i.e. heated) using high frequency alternating current, such as radiofrequency waves, to stop or prevent bleeding.

Figure 50:
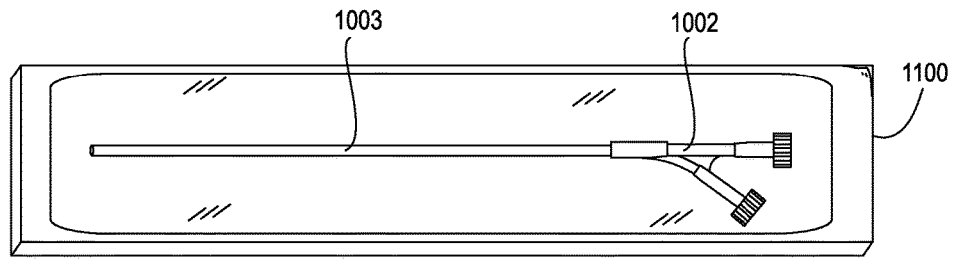
FIG. 50 illustrates a first embodiment of a kit including a connector, a catheter, and a syringe.

As shown in FIG. 50, the delivery device may be packaged and provided to a user in a kit 1100. In some embodiments, the kit includes connector 1002 and a catheter 1003. As described above, the connector 1002 may include two branches, as shown, or alternatively, the connector may include a single branch or more than two branches. As described above, the catheter may be sized and configured (for example, having a suitable length) to be fed through a METRX tube (Medtronic) or other minimally invasive surgical access device. The outer diameter of the catheter 1003 may be about 1 mm to 10 mm. In one specific embodiment, the catheter is a 14 gauge catheter. Kit 1100 may further include syringe. Syringe may include a hemostatic delivery agent, or may be filled upon removal from the kit by the user. The components of the kit are preferably packaged in a single unit. The package and each of the components are preferably sterilized and packaged in sterilized packaging. Alternatively, the components along with the packaging may be sterilized once assembled. In some embodiments, the kit 1100 may further comprise a guidewire, a guidewire delivery probe, a neural localization device, and/or a tissue modification device.

Figure 51A:
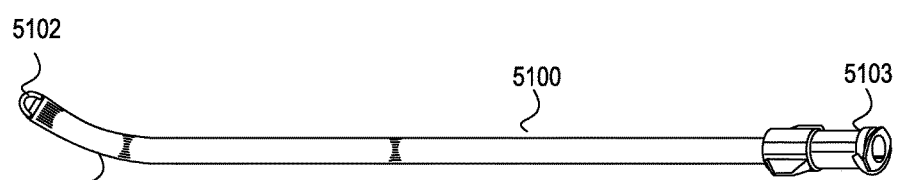
FIGS. 51A-51C illustrate an embodiment of a probe delivery device.
Figure 51B:
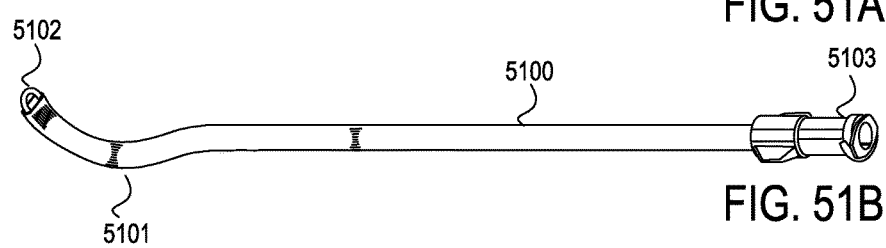
Figure 51C:
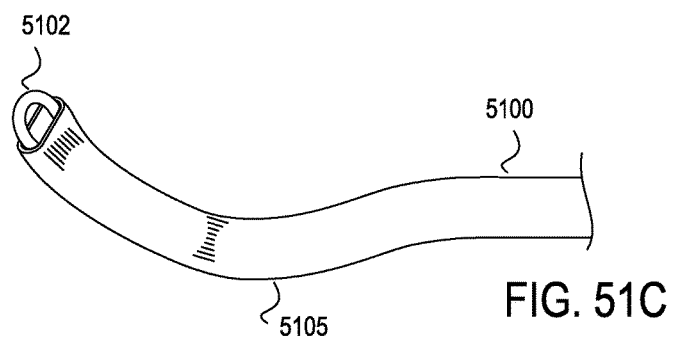

In further alternative configurations, a probe or cannula may be configured to deliver an agent to the surgical site. As described above with respect to the access probes, for example, in FIGS. 5A and 5B, a probe or cannula configured to deliver an agent to the surgical site may be positioned within the spine of a patient in a similar fashion. For example, the distal end of the probe may be advanced through and interlaminar window or laminotomy and advanced toward or through a neural foramen. The distal end of the probe delivery device may then be places in the surgical site adjacent to the target tissue. As described above, the probe may include an outer cannula and an inner cannula, slideable disposed within the outer cannula. Alternatively, as shown in FIGS. 51A to 51C, the delivery device probe 5100 may only include a single outer cannula. As shown, the distal end portion of the probe may be curved 5101 such that it may better access the desired tissue within the spine. Furthermore, the distal end of the delivery device may have an atraumatic end S 102 such that the probe may be advanced within the spine without damaging tissue such as never or vascular tissue. In some embodiments, the atraumatic tip may include a curved tip, as shown. In some embodiment, an extrusion may be molded around the distal tip of the catheter. Alternatively, the atraumatic tip may be a cap pressed into or welded to the end of the probe. In some embodiments, the distal end portion of the probe may be molded as two halves ("clam shell") that are then welded or snapped together. In this embodiment, the end may be closed and the probe may have apertures on the top and or bottom portion of the probe through which to deliver the agent. In some embodiments, as shown in FIGS. 51A and 51B, the delivery device may further include a connector S103 toward the proximal end of the cannula. The connector may a luer connector to receive a catheter and/or a syringe. In some embodiments, the delivery device may include a syringe or plunger suitable to deliver the agent through the device. The probe 5100 may be metal, plastic, or any other suitable material. In some embodiments, the material is rigid and/or has column strength such that the probe may be advanced into the spine without buckling.

In some alternative embodiments, the probe or delivery device of FIG. 5A to 5B or 51A to 51C may be configured to include an electrode or electrodes toward the distal end of the probe. In some embodiments, the electrode may be configured to deliver electricity. In some embodiments, the electricity may be used to stimulate nerve to determine the position of the nerve with respect to the probe. Alternatively, the energy may be used to ablate or cauterize the tissue adjacent to the electrode of the probe. In some embodiments, the entire metal tip of the probe may be electrified, however the majority of the tip may be insulated (with PEBAX for example) such that only a portion of the metal probe tip is exposed and able to delivery energy.

Although much of the description and accompanying figures generally focuses on surgical procedures in spine, in alternative embodiments, devices, systems and methods of the present invention may be used in any of a number of other anatomical locations in a patient's body. For example, in some embodiments, the flexible tissue modification devices of the present invention may be used in minimally invasive procedures in the shoulder, elbow, wrist, hand, hip, knee, foot, ankle, other joints, or other anatomical locations in the body. Similarly, although some embodiments may be used to remove or otherwise modify ligamentum flavum and/or bone in a spine to treat spinal stenosis, in alternative embodiments, other tissues may be modified to treat any of a number of other conditions. For example, in various embodiments, treated tissues may include but are not limited to ligament, tendon, bone, tumor, cyst, cartilage, scar, osteophyte, inflammatory tissue and the like. Non-target tissues may include neural tissue and/or neurovascular tissue in some embodiments or any of a number of other tissues and/or structures in other embodiments. In one alternative embodiment, for example, a flexible tissue modification device may be used to incise a transverse carpal ligament in a wrist while inhibiting damage to the median nerve, to perform a minimally invasive carpal tunnel release procedure. Thus, various embodiments described herein may be used to modify any of a number of different tissues, in any of a number of anatomical locations in the body, to treat any of a number of different conditions.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. Other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method for treating target tissue in a patient's spine, the method comprising:
    advancing a wire into the patient from a first location, through a neural foramen, and out of the patient from a second location;
    connecting a tissue modification device to the wire;
    positioning the tissue modification device through the neural foramen using the wire;
    modifying target tissue in the spine by moving the tissue modification device against the target tissue;
    delivering an agent to modified target tissue, wherein the agent is configured to inhibit blood flow from the modified target tissue wherein the step of delivering an agent to the modified target tissue comprises delivering an agent to the modified target tissue through a delivery device; and
    positioning the delivery device using the wire by threading the delivery device over the wire.

2. The method of claim 1, wherein the delivery device is a cannula having an atraumatic tip.

3. The method of claim 1, further comprising the step of providing suction and irrigation to the modified target tissue through the delivery device.

4. The method of claim 1, wherein the step of positioning the delivery device comprises connecting the distal end of the delivery device to the proximal end of the wire.

5. The method of claim 1, wherein the step of positioning the delivery device comprises positioning the delivery device through the neural foramen.

6. The method of claim 1, wherein the step of positioning the delivery device comprises positioning a catheter of the delivery device, wherein the catheter comprises a distal end and a proximal end, wherein the proximal end includes a connector.

7. The method of claim 6, wherein the step of positioning the delivery device comprises positioning the distal end of the catheter adjacent to the modified target tissue while the connector remains outside of the patient.

8. The method of claim 6, wherein the step of positioning the delivery device comprises removably locking the delivery device onto the wire with the connector.

9. The method of claim 1, wherein the agent is at least one of a haemostatic agent, a tissue sealant, a vasoconstrictor, a corticosteroid, a local anesthetic, an analgesic, and any combination thereof.

* * * * *